US006824770B1

(12) United States Patent
Falck-Pedersen

(10) Patent No.: US 6,824,770 B1
(45) Date of Patent: Nov. 30, 2004

(54) ADENOVIRUS GENE EXPRESSION SYSTEM

(75) Inventor: Erik S. Falck-Pedersen, New York, NY (US)

(73) Assignee: Cornell Research Foundation, Inc., Ithaca, NY (US)

(*) Notice: Subject to any disclaimer, the term of this patent is extended or adjusted under 35 U.S.C. 154(b) by 0 days.

(21) Appl. No.: 08/653,114

(22) Filed: May 24, 1996

Related U.S. Application Data

(63) Continuation of application No. 08/166,925, filed on Dec. 14, 1993, now abandoned.

(51) Int. Cl.[7] .............................................. A01N 63/00
(52) U.S. Cl. ...................... 424/93.2; 435/69.1; 435/456; 435/320.1; 435/325; 424/93.1; 536/23.1; 536/24.1; 514/44
(58) Field of Search ............................. 424/93.1, 93.2; 435/325, 320.1, 69.1, 456; 514/44; 536/23.1, 24.1

(56) References Cited

U.S. PATENT DOCUMENTS

| | | | |
|---|---|---|---|
| 4,740,461 A | * 4/1988 | Kaufman | .................. 435/69.1 |
| 4,745,051 A | 5/1988 | Smith et al. | |
| 4,963,481 A | 10/1990 | deVilliers | |
| 5,075,224 A | 12/1991 | Seeburg et al. | |
| 5,082,783 A | 1/1992 | Ernst et al. | |
| 5,223,408 A | 6/1993 | Goeddel et al. | |
| 5,242,822 A | 9/1993 | Marullo et al. | |
| 5,244,805 A | 9/1993 | Miller | |
| 5,731,172 A | * 3/1998 | Saito et al. | .............. 435/91.42 |

FOREIGN PATENT DOCUMENTS

WO          9107497     *   5/1991

OTHER PUBLICATIONS

Keating et al (1990) Exp Hematol 18:99–102.*
Huang et al (1990) Nucleic Acids Research 18:937–947.*
Schneider et al (J.Gen. Virol.(1989) 70: 417–427.*
Fang et al (Hepatology (1989) 10(5): 781–787).*
Fields (In Fundamental Virology, Raven Press, New York, 1990, p. 795).*
French et. al.; Circulation 90, 1991, 5: abstract.*
Cladaras et. al.; 1985; Virology 140: abstract.*
Bernard N. Fields, M.D. et al., Fundamental Virology, pp. 780.*
Choi et al., A generic intron increases gene expression in transgenic mice, Molecular and Cellular Biology 11: 3070–3074, Jun. 1991.*
Buchman and Berg, Comparison of intron–dependent and intron independent gene expression, Molecular and Cellular Biology 8: 4395–4405, Oct. 1988.*

Ishibashi et al., Hypercholesterolemia in low density lipoprotein receptor knockout mice and its reversal by adenovirus–mediated gene delivery, Journal of Clinical Investigation 92: 883–893, Aug. 1993.*
Li et al., Comparison of the expression of a mutant dihydrofolate reductase under control of different internal promoters in retroviral vectors, Human Gene Therapy 3: (Abstract Only), Aug. 1992.*
Pfarr et al., Differential effects of polyadenylation regions on gene expression in mammalian cells, DNA 5: 115–122, Apr. 1986.*
French et al., (Circulation 90(5): 2414–2424, 1944).*
Cladaras et. al.; (Virology 140(1): 44–45, 1985).*
Bernard N. Fields, M.D. et al., Fundamental Virology, 1990, pp. 780.*
Ginsberg, 1984, p. 1, lines 11–13.
Grand, 1987, *Biochem. J.*, vol. 241, pp. 25–38, p. 1, lines 21–22.
Nevins, 1987, *Microbiol. Rev.*, vol. 51, pp. 419–430, p. 1, lines 23–24.
Ginsberg, et al., 1989, *Proc Natl Acad Sci USA*, vol. 86, pp. 3823–3827 p. 1, lines 25–26.
Anderson, et al., 1985, *Cell*, vol. 43, pp. 215–222, p. 1, lines 27–28.
Burgert, et al., 1985, *Cell*, vol. .41, pp. 987–997, p. 1, lines 28–29.
Burgert, et al., 1987, *EMBO J.*, vol. 6, pp. 2019–2026, p. 1, line 29.
Carlin et al., 1989, *Cell*, vol. 57, pp. 135–144, p. 1, lines 29–30.
Gooding and Wold, 1990, *Crit. Rev. Immunol.*, vol. 10, pp. 53–71, p. 1, lines 30–31.
Gooding, et al., 1988, *Cell*, vol. 53, pp. 341–346, p. 1, lines 31–32.
Horton, et al., 1990, *J. Virol.*, vol. 64, pp. 1250–1255, p. 1, lines 32–33.
Tollefson, et al., 1991, *J. Virol.*, vol. 65, pp. 3095–3105, p. 1, lines33–34.
Wold and Gooding, 1989, *Mol. Biol. Med.*, vol. 6, pp. 433–452, p. 1, lines 34–35.
Wold and Gooding, 1991, *Virology*, vol. 184, pp. 1–8, p. 1, lines 35–36.

(List continued on next page.)

Primary Examiner—Dave T. Nguyen
Assistant Examiner—Richard Schnizer
(74) Attorney, Agent, or Firm—Leydig, Voit & Mayer, Ltd.

(57) ABSTRACT

The invention is directed to an adenoviral vector comprising (a) at least one insertion site for cloning a heterologous gene, and, in an orientation opposite to the direction of transcription of the adenoviral region into which it is inserted, (b) a heterologous promoter positioned upstream from the insertion site, (c) a eukaryotic splice acceptor and splice donor site positioned between the promoter and the insertion site; and (c) a polyadenylation sequence positioned downstream of the insertion site. The invention also provides a host cell infected with such a vector, a method of producing a selected protein, and a method of delivering a heterologous gene to an animal heart.

9 Claims, 28 Drawing Sheets

OTHER PUBLICATIONS

Berkner, et al., 1984, *Nuc. Acids Res.*, vol. 12, pp. 1925–1941, p. 1, lines 39–p.2, lline 1 and p. 2, lines 24–25 and p. 3, lines 7–8.

Chanda, et al., 1990, *Virology*, vol. 175, pp. 535–547, p. 2, lines 1–2 and p. 2, line 25.

Haj–Ahmad, et al., 1986, *J. Virol.*, vol. 57, pp. 267–274, p. 2, lines 2–3.

Saito, et al., 1985, *J. Virol.*, vol. 54, pp. 711–719, p. 2, lines 3–4.

Ghosh–Choudhury, et al., 1987, *EMBO J.* vol. 6, pp. 1733–1739 p. 2, lines 6–7.

Graham, et al., 1977, *J. Gen. Virol.*, vol. 36, pp. 59–72, p. 2, lines 12–13.

Graham, et al., 1992, in *Vaccines: New Approaches to Immunological Problems*, R. W. Ellis (Ed.), Butterworth-Heinemann, Boston, MA., pp. 363–390, p. 2, lines 16–18.

Dewar, et al., 1989, *J. Virol.*, vol. 63, pp. 129–136, p. 2, lines 25–26.

Graham, 1990, *Trends Biotechnol.*, vol. 8, pp. 85–87; p. 2, lines 26–27.

Johnson, et al., 1988, *Virology*, vol. 164, pp. 1–14, p. 2, lines 27–28.

Lubeck, et al., 1989, *Proc. Natl. Acad. Sci. USA*, vol. 86, pp. 6763–6767, p. 2, lines 28–29.

McDermott, et al., 1989, *Virology*, vol. 169, pp. 244–247, p. 2, lines 29–30.

Morin, et al., 1987, *Proc. Natl. Acad. Sci. USA*, vol. 84, pp. 4626–4630, p. 2, lines 30–31.

Prevec, et al., 1989, *J. Gen. Virol.*, vol. 70, pp. 429–434, p. 2, lines 31–32.

Prevec, et al., 1990 *J. Inf. Dis.,*, vol. 161, pp. 27–30, p. 2, lines 32–33.

Schneider, et al., 1989, *J. Gen. Virol.*, vol. 70, pp. 417–427, p. 2, lines 33–34.

Vernon, et al., 1991, *J. Gen. Virol.*, vol. 72, pp. 1243–1251, p. 2, lines 34–35.

Yuasa, et al., 1991, *J. Gen. Virol.*, vol. 72, pp. 1927–1934, p. 2, lines 35–36.

Thummel et al., 1981, *Cell*, vol. 23, pp. 825–836, p. 3, line 6.

Grunhaus, et al., 1992, *Seminars in Virology*, vol. 3, pp. 237–252, p. 3, lines 7–8.

Rosenfeld, et al., 1992, *Cell*, vol. 68, pp. 143–155, p. 3, lines 12–13.

Friedman, et al., 1986, *Mol. Cell. Biol.*, vol. 6, pp. 3791–3797, p. 3, lines 19–20.

Babiss, et al., 1986, *Mol. Cell. Biol.*, vol. 6, pp. 3798–3806, p. 3, lines 20–21.

Babich, et al., 1983, *Mol. Cell. Biol.*, vol. 3, pp. 1212–1221, p. 5, line 29.

Beltz, et al., 1979, *J. Mol. Biol.*, vol. 131, pp. 353–373, p. 5, line 30.

Schneider, et al., 1987, *Annu. Rev. Biochem.*, vol. 56, pp. 317–332, p. 5, lines 31–32.

Harrison, et al., 1977, *Virology*, vol. 77, pp. 319–329, p. 5, lines 34–35.

Jones, et al., 1979, *Cell*, vol. 17, pp. 683–689, p. 5, line 35.

Mulligan, R.C., 1993, *Science*, vol. 260, pp. 926–931, p. 6, lines 8–9.

Straub, et al., 1990, *Proc. Natl. Acad. Sci. USA*, vol. 87, pp. 9514–9518, p. 6, lines 13–14.

Yamada, et al., 1992, *Biochem. Biophys. Res. Commun.*, vol. 184, pp. 367–372, p. 6, lines 14–15.

Zhoa, et al., 1992, *Endocrinology*, vol. 130, pp. 3529–3536, p. 6, lines 15–16.

de la Pena, et al., 1992, *Biochem. J.*, vol. 284, p0p. 891–899, p. 6, lines 16–17.

Gustafson, et al., 1987, *Proc. Natl. Acad. Sci. USA*, vol. 84, pp. 3122–3126, p. 7, lines 8–9.

Rindt, et al., 1993, *J. Biol. Chem.*, vol. 268, pp. 5332–5338, p. 7, lines 16–17.

Subramanian, et al., 1991, *J. Biol. Chem.*, vol. 266, pp. 24613–24620, p. 7, lines 17–18.

Kitsis, et al., 1991, *Proc. Natl. Acad. Sci. USA*, vol. 88, pp. 4138–4142, p. 7, lines 24–26.

Lin, et al., 1990, *Circulation*, vol. 82, pp. 2217–2221, p. 7, line 26.

Ascadi, et al., 1991, *The New Biologist*, vol. 3, pp. 71–81, p. 7, lines 27–28.

Kitsis, et al., 1993, In: *Methods in Molecular Genetics*, K. W. Adolph (Ed.), Academic Press, Inc., New York, vol. 1, pp. 374–392, p. 7.

Kirshenbaum, et al., 1993, *J. Clin. Invest.*, vol. 92, pp. 381–387, p. 7, lines 35–36.

Stratford–Perricaudet, et al., 1992, *J. Clin. Invest.*, vol. 90, pp. 626–630, p. 8, lines 4–5.

* cited by examiner

FIG.2 pGEM2AdCMV

3818 BASE PAIRS    UNIQUE SITES

- 10 EcoR I
- 283
- 373 Not I
- 374 Eag I
- 400 Spe I
- 634 Bal I
- 739 Nde I
- 761 Sty I
- 761 Nco I
- 739 SnaB I
- 972 Ava I
- 965 Sac I
- 965 Ecl136 II
- 972 BsaA I
- 972 PspA I
- 972 Sma I
- 977 BamH I
- 983 Xba I
- 989 Acc I
- 989 Sal I
- 993 BspM I
- 995 Pst I
- 1004 HinD III
- 1049 Pvu II
- 1638 AlwN I
- 2115
- 2205 Bpm I
- 2340 BamH105 I
- 2487 Psp I
- 2487 BapC I
- 2598 PvhI
- 2715 Sca I
- 2715 Xmn I
- 3317 EcoN I
- 3382 Sph I
- 3450 Eco47 III
- 3543 Nde I
- 3543 NgoM I
- 3576 Nhe I

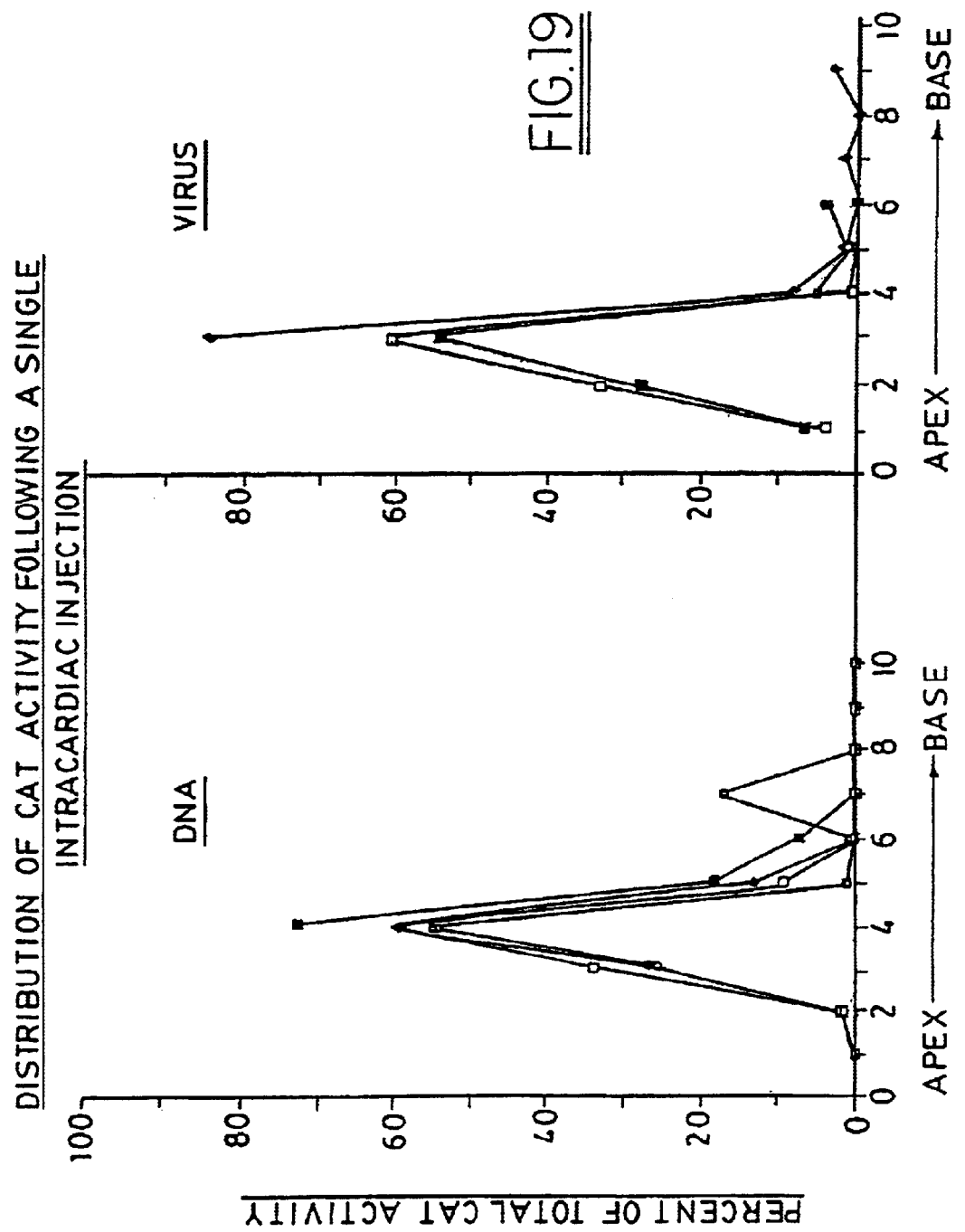

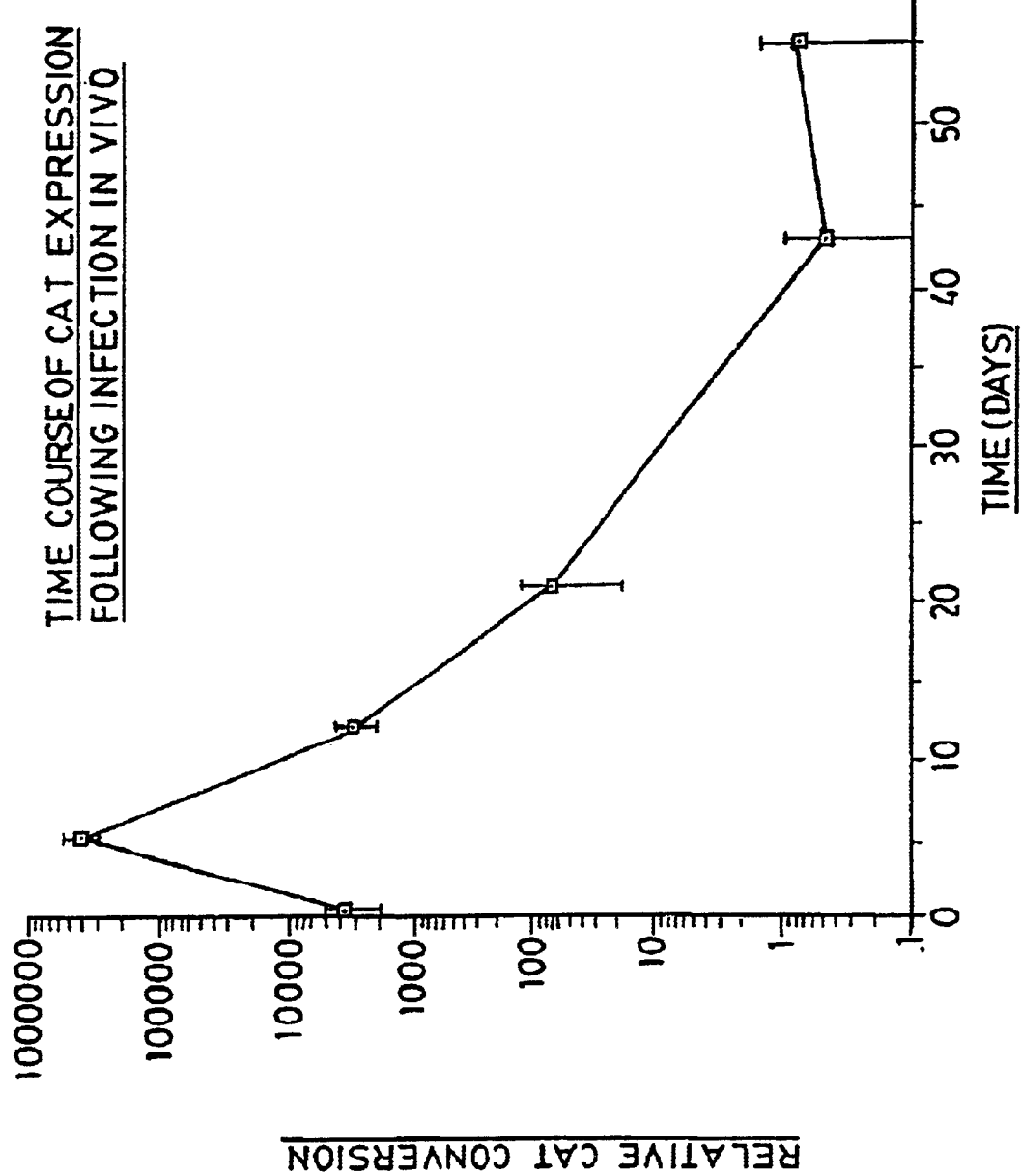

FIG. 22

```
TTCCATCATC AATAATATAC CTTATTTTGG ATTGAAGCCA ATATGATAAT GAGGGGGTGG    60
AGTTTGTGAC GTGGCGCGGG GCGTGGGAAC GGGGCGGGTG ACGTAGTAGT GTGGCGGAAG   120
TGTGATGTTG CAAGTGTGGC GGAACACATG TAAGCGACGG ATGTGGCAAA AGTGACGTTT   180
TTGGTGTGCG CCGGTGTACA CAGGAAGTGA CAATTTTCGC GCGGTTTTAG GCGGATGTTG   240
TAGTAAATTT GGGCGTAACC GAGTAAGATT TGGCCATTTT CGCGGGAAAA CTGAATAAGA   300
GGAAGTGAAA TCTGAATAAT TTTGTGTTAC TCATAGCGCG TAATATTTGT CTAGGGCCTT   360
GCGGCCGCAA GTTGACATTG ATTATTGACT AGTTATTAAT AGTAATCAAT TACGGGGTCA   420
TTAGTTCATA GCCCATATAT GGAGTTCCGA GTTACATAAC TTACGGTAAA TGGCCCGCCT   480
GGCTGACCGC CCAACGACCC CCGCCCATTG ACGTCAATAA TGACGTATGT TCCCATAGTA   540
ACGCGAATAG GGACTTTCCA TTGACGTCAA TGGGTGGAGT ATTTACGGTA AACTGCCCAC   600
TTGGCAGTAC ATCAAGTGTA TCATATGCCA AGTACGCCCC CTATTGACGT CAATGACGGT   660
AAATGGCCCG CCTGGCATTA TGCCCAGTAC ATGACCTTAT GGGACTTTCC TACTTGGCAG   720
TACATCTACG TATTAGTCAT CGCTATTACC ATGGTGATGC GGTTTTGGCA GTACATCAAT   780
GGGCGTGGAT AGCGGTTTGA CTCACGGGGA TTTCCAAGTC TCCACCCCAT TGACGTCAAT   840
GGGAGTTTGT TTTGGCACCA AAATCAACGG GACTTTCCAA AATGTCGTAA CAACTCCGCC   900
CCATTGACGC AAATGGGCGG TAGGCGTGTA CGGTGGGAGG TCTATATAAG CAGAGCTCGC   960
CCGGGGATCC TCTAGAATTC GCTGTCTGCG AGGGCCAGCT GTTGGGGTGA GTACTCCCTC  1020
TCAAAAGCGG GCATGACTTC TGCGCTAAGA TTGTCAGTTT CCAAAAACGA GGAGGATTTG  1080
ATATTCACCT GGCCCGCGGT GATGCCTTTG AGGGTGGCCG CGTCCATCTG GTCAGAAAAG  1140
ACAATCTTTT TGTTGTCAAA AGCGCTTGAG GTGTGGCAGG CTTGAGATCT GGCCATACAC  1200
TTGAGTGACA ATGACATCCA CTTTGCCTTT CTCTCCACAG GTGTCCACTC CCAGGTCCAA  1260
CTGCAGCCCC CAAGCTTGGG AATTCTCTCG GAAACGATGA AATATACAAG TTATATCTTG  1320
GCTTTTCAGC TCTGCATCGT TTTGGGTTCT CTTGGCTGTT ACTGCCAGGA CCCATATGTA  1380
AAAGAAGCAG AAAACCTTAA GAAATATTTT AATGCAGGTC ATTCAGATGT AGCGGATAAT  1440
GGAACTCTTT TCTTAGGCAT TTTGAAGAAT TGGAAAGAGG AGAGTGACAG AAAAATAATG  1500
CAGAGCCAAA TTGTCTCCTT TTACTTCAAA CTTTTTAAAA ACTTTAAAGA TGACCAGAGC  1560
ATCCAAAAGA GTGTGGAGAC CATCAAGGAA GACATGAATG TCAAGTTTTT CAATAGCAAC  1620
AAAAAGAAAC GAGATGACTT CGAAAAGCTG ACTAATTATT CGGTAACTGA CTTGAATGTC  1680
CAACGCAAAG CAATACATGA ACTCATCCAA GTGATGGCTG AACTGTCGCC AGCAGCTAAA  1740
ACAGGGAAGC GAAAAAGGAG TCAGATGCTG TTTCAAGGTC GAAGAGCATC CCAGTAATGG  1800
TTGTCCTGCG GATCCCTGGC AGTGGCGCAT AGCGATGCGC GGCAGAACCC CTTTGATTTT  1860
TAAACGGCGC AGACGGCAAG GGTGGGGGGT AAATAATCAC CCGAGAGTGT ACAAATAAAA  1920
ACATTTGCCT TTATTGAAAG TGTCTCCTAG TACATTATTT TTACATGTTT TTCAAGTGAC  1980
AAAAAGAAGT GGCGCTCCTA ATCTGCGCAC TGTGGCTGCG GGAGCTCTAG AGTCGACGGT  2040
ATCGCCCGAC ATCACCTGTG TCTATGGCCA CTGCCTTGGC TCACAAGTAC CACTAAACCC  2100
CCTTTCCTGC TCTTGCCTGT GAACAATGGT TAATTGTTCC CAAGAGAGCA TCTGTCAGTT  2160
GTTGGCAAAA TGATAGACAT TTGAAAATCT GTCTTCTGAC AAATAAAAAG CATTTATGTT  2220
CACTGCAATG ATGTTTTAAA TTATTTGTCT GTGTCATAGA AGGGTTTATG CTAAGTTTTC  2280
AAGATACAAA GAAGTGAGGC TTCAGGTCTG ACCTTGGGGA AATAAATGAA TTACACTTCA  2340
AATTGTGTTG TCAGCTAAGC AGCAGTAGCC ACAGTCTAGC TGAGGGTAAC TCCAGGGTGC  2400
GCCACAATGT GGCCTCCGAC TGTGGTTGCT TCATGCTAGT GAAAAGCGTG GCTGTGATTA  2460
AGCATAACAT GGTATGTGGC AACTGCGAGG ACAGGGCCTC TCAGATGCTG ACCTGCTCGG  2520
ACGGCAACTG TCACCTGCTG AAGACCATTC ACGTAGCCAG CCACTCTCGC AAGGCCTGGC  2580
CAGTGTTTGA GCATAACATA CTGACCCGCT GTTCCTTGCA TTTGGGTAAC AGGAGGGGGG  2640
TGTTCCTACC TTACCAATGC AATTTGAGTC ACACTAAGAT ATTGCTTGAG CCCGAGAGCA  2700
TGTCCAAGGT GAACCTGAAC GGGGTGTTTG ACATGACCAT GAAGATCTGG AAGGTGCTGA  2760
GGTACGATGA GACCCGCACC AGGTGCAGAC CCTGCGAGTG TGGCGGTAAA CATATTAGGA  2820
ACCAGCCTGT GATGCTGGAT GTGACCGAGG AGCTGAGGCC CGATCACTTG GTGCTGGCCT  2880
GCACCCGCGC TGAGTTTGGC TCTAGCGATG AAGATACAGA TTGAGGTACT GAAATGTGTG  2940
```

FIG. 22(continued)

```
GGCGTGGCTT AAGGGTGGGA AAGAATATAT AAGGTGGGGG TCTTATGTAG TTTTGTATCT   3000
GTTTTGCAGC AGCCGCCGCC GCCATGAGCA CCAACTCGTT TGATGGAAGC ATTGTGAGCT   3060
CATATTTGAC AACGCGCATG CCCCCATGGG CCGGGGTGCG TCAGAATGTG ATGGGCTCCA   3120
GCATTGATGG TCGCCCCGTC CTGCCCGCAA ACTCTACTAC CTTGACCTAC GAGACCGTGT   3180
CTGGAACGCC GTTGGAGACT GCAGCCTCCG CCGCCGCTTC AGCCGCTGCA GCCACCGCCC   3240
GCGGGATTGT GACTGACTTT GCTTTCCTGA GCCCGCTTGC AAGCAGTGCA GCTTCCCGTT   3300
CATCCGCCCG CGATGACAAG TTGACGGCTC TTTTGGCACA ATTGGATTCT TTGACCCGGG   3360
AACTTAATGT CGTTTCTCAG CAGCTGTTGG ATCTGCGCCA GCAGGTTTCT GCCCTGAAGG   3420
CTTCCTCCCC TCCCAATGCG GTTTAAAACA TAAATAAAAA ACCAGACTCT GTTTGGATTT   3480
GGATCAAGCA AGTGTCTTGC TGTCTTTATT TAGGGGTTTT GCGCGCGCGG TAGGCCCGGG   3540
ACCAGCGGTC TCGGTCGTTG AGGGTCCTGT GTATTTTTTC CAGGACGTGG TAAAGGTGAC   3600
TCTGGATGTT CAGATACATG GGCATAAGCC CGTCTCTGGG GTGGAGGTAG CACCACTGCA   3660
GAGCTTCATG CTGCGGGGTG GTGTTGTAGA TGATCCAGTC GTAGCAGGAG CGCTGGGCGT   3720
GGTGCCTAAA AATGTCTTTC AGTAGCAAGC TGATTGCCAG GGGCAGGCCC TTGGTGTAAG   3780
TGTTTACAAA GCGGTTAAGC TGGGATGGGT GCATACGTGG GGATATGAGA TGCATCTTGG   3840
ACTGTATTTT TAGGTTGGCT ATGTTCCCAG CCATATCCCT CCGGGGATTC ATGTTGTGCA   3900
GAACCACCAG CACAGTGTAT CCGGTGCACT TGGGAAATTT GTCATGTAGC TTAGAAGGAA   3960
ATGCGTGGAA GAACTTGGAG ACGCCCTTGT GACCTCCAAG ATTTTCCATG CATTCGTCCA   4020
TAATGATGGC AATGGGCCCA CGGGCGGCGG CCTGGGCGAA GATATTTCTG GGATCACTAA   4080
CGTCATAGTT GTGTTCCAGG ATGAGATCGT CATAGGCCAT TTTTACAAAG CGCGGGCGGA   4140
GGGTGCCAGA CTGCGGTATA ATGGTTCCAT CCGGCCCAGG GGCGTAGTTA CCCTCACAGA   4200
TTTGCATTTC CCACGCTTTG AGTTCAGATG GGGGGATCAT GTCTACCTGC GGGGCGATGA   4260
AGAAAACGGT TTCCGGGGTA GGGGAGATCA GCTGGGAAGA AAGCAGGTTC CTGAGCAGCT   4320
GCGACTTACC GCAGCCGGTG GGCCCGTAAA TCACACCTAT TACCGGGTGC AACTGGTAGT   4380
TAAGAGAGCT GCAGCTGCCG TCATCCCTGA GCAGGGGGGC CACTTCGTTA AGCATGTCCC   4440
TGACTCGCAT GTTTTCCCTG ACCAAATCCG CCAGAAGGCG CTCGCCGCCC AGCGATAGCA   4500
GTTCTTGCAA GGAAGCAAAG TTTTTCAACG GTTTGAGACC GTCCGCCGTA GGCATGCTTT   4560
TGAGCGTTTG ACCAAGCAGT TCCAGGCGGT CCCACAGCTC GGTCACCTGC TCTACGGCAT   4620
CTCGATCCAG CATATCTCCT CGTTTCGCGG GTTGGGGCGG CTTTCGCTGT ACGGCAGTAG   4680
TCGGTGCTCG TCCAGACGGG CCAGGGTCAT GTCTTTCCAC GGGCGCAGGG TCCTCGTCAG   4740
CGTAGTCTGG GTCACGGTGA AGGGGTGCGC TCCGGGCTGC GCGCTGGCCA GGGTGCGCTT   4800
GAGGCTGGTC CTGCTGGTGC TGAAGCGCTG CCGGTCTTCG CCCTGCGCGT CGGCCAGGTA   4860
GCATTTGACC ATGGTGTCAT AGTCCAGCCC CTCCGCGGCG TGGCCCTTGG CGCGCAGCTT   4920
GCCCTTGGAG GAGGCGCCGC ACGAGGGGCA GTGCAGACTT TGAGGGCGT AGAGCTTGGG   4980
CGCGAGAAAT ACCGATTCCG GGGAGTAGGC ATCCGCGCCG CAGGCCCCGC AGACGGTCTC   5040
GCATTCCACG AGCCAGGTGA GCTCTGGCCG TTCGGGGTCA AAAACCAGGT TTCCCCCATG   5100
CTTTTTGATG CGTTTCTTAC CTCTGGTTTC CATGAGCCGG TGTCCACGCT CGGTGACGAA   5160
AAGGCTGTCC GTGTCCCCGT ATACAGACTT GAGAGGTCGA GCGATGCCCT TGAGAGCCTT   5220
CAACCCAGTC AGCTCCTTCC GGTGGGCGCG GGGCATGACT ATCGTCGCCG CACTTATGAC   5280
TGTCTTCTTT ATCATGCAAC TCGTAGGACA GGTGCCGGCA GCGCTCTGGG TCATTTTCGG   5340
CGAGGACCGC TTTCGCTGGA GCGCGACGAT GATCGGCCTG TCGCTTGCGG TATTCGGAAT   5400
CTTGCACGCC CTCGCTCAAG CCTTCGTCAC TGGTCCCGCC ACCAAACGTT TCGGCGAGAA   5460
GCAGGCCATT ATCGCCGGCA TGGCGGCCGA CGCGCTGGGC TACGTCTTGC TGGCGTTCGC   5520
GACGCGAGGC TGGATGGCCT TCCCCATTAT GATTCTTCTC GCTTCCGGC GCATCGGGAT   5580
GCCCGCGTTG CAGGCCATGC TGTCCAGGCA GGTAGATGAC GACCATCAGG ACAGCTTCA   5640
AGGATCGCTC GCGGGTAAAA AGGCCGCGTT GCTGGCGTTT TTCCATAGGC TCCGCCCCC   5700
TGACGAGCAT CACAAAAATC GACGCTCAAG TCAGAGGTGG CGAAACCCGA CAGGACTATA   5760
AAGATACCAG GCGTTTCCCC CTGGAAGCTC CCTCGTGCGC TCTCCTGTTC CGACCCTGCC   5820
GCTTACCGGA TACCTGTCCG CCTTTCTCCC TTCGGGAAGC GTGGCGCTTT CTCAATGCTC   5880
```

FIG. 22
(continued)

```
ACGCTGTAGG TATCTCAGTT CGGTGTAGGT CGTTCGCTCC AAGCTGGGCT GTGTGCACGA 5940
ACCCCCCGTT CAGCCCGACC GCTGCGCCTT ATCCGGTAAC TATCGTCTTG AGTCCAACCC 6000
GGTAAGACAC GACTTATCGC CACTGGCAGC AGCCACTGGT AACAGGATTA GCAGAGCGAG 6060
GTATGTAGGC GGTGCTACAG AGTTCTTGAA GTGGTGGCCT AACTACGGCT ACACTAGAAG 6120
GACAGTATTT GGTATCTGCG CTCTGCTGAA GCCAGTTACC TTCGGAAAAA GAGTTGGTAG 6180
CTCTTGATCC GGCAAACAAA CCACCGCTGG TAGCGGTGGT TTTTTTGTTT GCAAGCAGCA 6240
GATTACGCGC AGAAAAAAAG GATCTCAAGA AGATCCTTTG ATCTTTTCTA CGGGGTCTGA 6300
CGCTCAGTGG AACGAAAACT CACGTTAAGG GATTTTGGTC ATGAGATTAT CAAAAAGGAT 6360
CTTCACCTAG ATCCTTTTAA ATTAAAAATG AAGTTTTAAA TCAATCTAAA GTATATATGA 6420
GTAAACTTGG TCTGACAGTT ACCAATGCTT AATCAGTGAG GCACCTATCT CAGCGATCTG 6480
TCTATTTCGT TCATCCATAG TTGCCTGACT CCCCGTCGTG TAGATAACTA CGATACGGGA 6540
GGGCTTACCA TCTGGCCCCA GTGCTGCAAT GATACCGCGA GACCCACGCT CACCGGCTCC 6600
AGATTTATCA GCAATAAACC AGCCAGCCGG AAGGGCCGAG CGCAGAAGTG GTCCTGCAAC 6660
TTTATCCGCC TCCATCCAGT CTATTAATTG TTGCCGGGAA GCTAGAGTAA GTAGTTCGCC 6720
AGTTAATAGT TTGCGCAACG TTGTTGCCAT TGCTGCAGGC ATCGTGGTGT CACGCTCGTC 6780
GTTTGGTATG GCTTCATTCA GCTCCGGTTC CCAACGATCA AGGCGAGTTA CATGATCCCC 6840
CATGTTGTGC AAAAAAGCGG TTAGCTCCTT CGGTCCTCCG ATCGTTGTCA GAAGTAAGTT 6900
GGCCGCAGTG TTATCACTCA TGGTTATGGC AGCACTGCAT AATTCTCTTA CTGTCATGCC 6960
ATCCGTAAGA TGCTTTTCTG TGACTGGTGA GTACTCAACC AAGTCATTCT GAGAATAGTG 7020
TATGCGGCGA CCGAGTTGCT CTTGCCCGGC GTCAACACGG GATAATACCG CGCCACATAG 7080
CAGAACTTTA AAAGTGCTCA TCATTGGAAA ACGTTCTTCG GGGCGAAAAC TCTCAAGGAT 7140
CTTACCGCTG TTGAGATCCA GTTCGATGTA ACCCACTCGT GCACCCAACT GATCTTCAGC 7200
ATCTTTTACT TTCACCAGCG TTTCTGGGTG AGCAAAAACA GGAAGGCAAA ATGCCGCAAA 7260
AAAGGGAATA AGGGCGACAC GGAAATGTTG AATACTCATA CTCTTCCTTT TTCAATATTA 7320
TTGAAGCATT TATCAGGGTT ATTGTCTCAT GAGCGGATAC ATATTTGAAT GTATTTAGAA 7380
AAATAAACAA ATAGGGGTTC CGCGCACATT TCCCCGAAAA GTGCCACCTG ACGTCTAAGA 7440
AACCATTATT ATCATGACAT TAACCTATAA AAATAGGCGT ATCACGAGGC CCTTTCGTCT 7500
TCAAGAA                                                          7507
```

ADENOVIRUS GENE EXPRESSION SYSTEM

This application is a continuation of application, Ser. No. 08/166,925, filed on Dec. 14, 1993 abandoned.

This invention was made with Government support under Grant Nos. R01GM1967 and R01DK43046, awarded by the National Institutes of Health. The Government has certain rights in the invention.

FIELD OF THE INVENTION

The present invention relates generally to a recombinant viral expression system. More particularly, the present invention relates to a highly efficient, recombinant adenovirus expression system capable of expressing a heterologous gene(s) in a host mammalian cell.

BACKGROUND OF THE INVENTION

The human adenovirus-5 (Ad5) genome consists of a double-stranded linear DNA molecule of 36 kilo-basepair (bp) (Ginsberg, 1984). The virus replication cycle has two phases: an early phase, during which 4 transcription units E1, E2, E3, and E4 are expressed, and a late phase occurring after the onset of viral DNA synthesis when late transcripts are expressed from the major late promoter (MLP). These late messages encode most of the viral structural proteins. E1, E2 and E4 gene products of human adenoviruses are involved in transcriptional activation, cell transformation, and viral DNA replication as well as other viral functions, and are essential for viral growth (Grand, 1987, Biochem. J., vol. 241, pp. 25–38; and Nevins, 1987, Microbiol. Rev., vol. 51, pp. 419–430). In contrast, E3 gene products are not required for viral replication in cultured cells (Ginsberg et al., 1989,), but appear to be involved in evading immune surveillance in vivo (Anderson et al., 1985, Cell, vol. 43, pp. 215–222; Burgert et al., 1985, Cell, vol. 41, pp. 987–997; Burgert et al., 1987, EMBO J., vol. 6, pp. 2019–2026; Carlin et al., 1989, Cell, vol. 57, pp. 135–144; Gooding and Wold, 1990, Crit. Rev. Immunol., vol. 10, pp. 53–71; Gooding et al., 1988, Cell, vol. 53, pp. 341–346; Horton et al., 1990, J. Virol., vol. 64, pp. 1250–1255; Tollefson et al., 1991, J. Virol., vol. 65, pp. 3095–3105; Wold and Gooding, 1989, Mol. Biol. Med., vol. 6, pp. 433–452; and Wold and Gooding, 1991, Virology, vol. 184, pp. 1–8).

E1 and E3 and a site upstream of E4 have been utilized as sites for insertion of foreign DNA sequences in the generation of recombinant adenoviruses (Berkner et al., 1984, Nuc. Acids. Res., vol. 12, pp. 1925–1941; Chanda et al., 1990, Virology, vol. 175, pp. 535–547; Haj-Ahmad et al., 1986, J. Virol., vol. 57, pp. 267–274; and Saito et al., 1985, J. Virol., vol. 54, pp. 711–719). Since the upper size limit for DNA molecules that can be packaged into adenovirus particles is approximately 105% of the wild-type genome (Ghosh-Choudhury et al., 1987, EMBO J., vol. 6, pp. 1733–1739), only about 2 kb of extra DNA can be inserted without compensating deletions of viral DNA. Although E1 is essential for virus replication in cell culture, foreign DNA can be substituted for E1 sequences when the virus is grown in 293 cells which are transformed by adenovirus-5 DNA and constitutively express E1 (Graham et al., 1977, J. Gen. Virol., vol. 36, pp. 59–72). Several vectors having 1.9 kb deleted from E3 of adenovirus-5 have been constructed without interfering with virus replication in cell culture (Graham et al., 1992, Vaccines; New Approaches to Immunological Problems, R. W. Ellis (Ed.), Butterworth-Heinemann, Boston, Mass., pp. 364–390). Such vectors allow for insertion of up to 4 kb of foreign DNA. Recombinant adenoviruses containing inserts in E3 replicate in all adenovirus-permissive cell lines and may be suitable as live recombinant viral vaccines since a number of adenovirus vectors containing E3 inserts have been shown to express foreign genes efficiently both in vitro and in vivo (Berkner, 1988: Chanda et al., 1990; Dewar et al., 1989, J. Virol., vol. 63, pp. 129–136; Graham, 1990, Trends Biotechnol., vol. 8, pp. 85–87; Graham et al., 1992; Johnson et al., 1988, Virology, vol. 164, pp. 1–14; Lubeck et al., 1989, Proc. Natl. Acad. Sci. USA, vol. 86, pp. 6763–6767; McDermott et al. 1989, Virology, vol. 169, pp. 244–247; Morin et al., 1987, Proc. Natl. Acad. Sci. USA, vol. 84, pp. 4626–4630; Prevec et al., 1989, J. Gen. Virol., vol. 70, pp. 429–434; Prevec et al., 1990, J. Inf. Dis., vol. 161, pp. 27–30; Schneider et al., 1989, J. Gen. Virol. , vol. 70, pp. 417–427; Vernon et al., 1991, J. Gen. Virol., vol. 72, pp. 1243–1251; and Yuasa et al., 1991, J. Gen. Virol., vol. 72, pp. 1927–1934).

Adenoviruses are good mammalian cell expression vectors with potential utility as live recombinant vaccines, in gene therapy, or for high level protein production in mammalian cells.

Adenovirus expression vectors have been in use for the past decade (Thummel et al., 1981, Cell, vol. 23, pp. 825–836; Berkner et al., 1984, Nucleic Acids Res., vol. 12, pp. 1925–1941; and for a review see Grunhaus et al., 1992, Seminars in Virology 3, pp. 237–252), and more recently exploited for the purpose of gene therapy (Herz et al., 1993, Proc. Natl. Acad. Sci. U.S.A., vol. 90, pp. 2812–2816; Rosenfeld et al., 1991, Science, vol. 252, pp. 431–434; and Rosenfeld et al., 1992, Cell, vol. 68, pp. 143–155). Features of adenovirus based expression vectors which make them attractive to gene therapy applications include very efficient uptake into cells which contain the appropriate adenovirus receptor and uptake pathway, and the ability to carry up to 7.5 kb of foreign DNA. Adenovirus vectors allow a reporter gene to be under the control of tissue specific promoter elements (Friedman et al., 1986, Mol. Cell. Biol., vol. 6, pp. 3791–3797; and Babiss et al., 1986, Mol. Cell. Biol., vol. 6, pp. 3798–3806) as well as a variety of viral and mammalian constitutive promoter elements (Mittal et al., 1993, Virus Research, vol. 28, pp. 67–90).

One such example of an adenovirus-based vector system is described in Mittal et al., 1993, Virus Research, vol. 28, pp. 67–90. The authors here describe a helper-independent adenovirus type 5-luciferase recombinant containing the firefly luciferase gene flanked by simian virus 40 (SV40) regulatory sequences inserted into the early region 3 (E3) of the adenovirus-5 genome. A plasmid containing the luciferase gene and SV40 regulatory sequences in the E3 region was co-transfected with a plasmid containing the adenovirus-5 dl309 genome in circular form. Upon transfection of 293 cells, virus progeny produced by in vivo recombination between the two plasmids resulted in rescue of the adenovirus type 5-luciferase recombinant (i.e., E3 insert in Adenovirus-5 genome).

Gomez-Foix et al., 1992, J. Biol. Chemistry, vol. 267, no. 35, pp. 25129–25134, discloses adenovirus-mediated transfer of the muscle glycogen phosphorylase gene into hepatocytes in culture. The preparation of a recombinant adenovirus containing the cDNA encoding rabbit muscle glycogen phosphorylase is described whereby the cytomegalovirus (CMV) early gene promoter/enhancer, pUC 18 polylinker, fragment of the SV40 genome that includes the small T-antigen intron and the polyadenylation signal, and cDNA that includes all of the protein coding region of the rabbit muscle glycogen phosphorylase, was inserted into vector pAC. The resulting plasmid was co-transfected into 293 cells with plasmid pJM17, which encodes a full-length adenovirus-5 genome. Homologous recombination between the recombinant plasmids in 293 cells generated a genome of packageable size in which the adenovirus early region 1 was replaced by the cloned chimeric gene encoding rabbit muscle glycogen phosphorylase.

Roessler et al., 1993, *J. Clin. Invest.*, discloses using a recombinant adenoviral vector for the expression of the gene for *Escherichia coli* beta-galactosidase within synovium tissue. Replication defective adenoviral vectors are deleted of sequences spanning E1A, E1B and a portion of the E3 region, impairing the ability of this virus to replicate or transform nonpermissive cells. The early enhancer/promoter of the cytomegalovirus (CMV) was inserted into this vector to drive transcription of lacZ with a SV40 polyadenylation sequence cloned downstream from this reporter.

Yang et al., *Proc. Natl. Acad. Sci. USA*, vol. 90, pp. 9480–9484, discloses the expression of cystic fibrosis transmembrane conductance regulator (CFTR) by adenovirus-mediated gene transfer. The recombinant adenoviruses were produced by homologous recombination of two vectors which contain the following relevant sequences: 5' ITR of adenovirus-5 spanning 0–1 map units; Tha I-SnaBI fragment of the immediate-early gene of cytomegalovirus; promoter from the chicken β-actin gene spanning Xho I at nucleotide (nt) −275 to Mbo I at nt +1; human CFTR cDNA containing 60 nt of 5' untranslated sequence, the entire coding sequence, and 80 nt of 3' untranslated sequence; simian virus 40 late gene polyadenylation signal; 9.2–16.1 map units of adenovirus-5; and plasmid sequences.

Herz et al., 1993, *Proc. Natl. Acad. Sci. USA*, vol. 90, pp. 2812–2816, discloses the use of adenovirus-mediated gene transfer to transiently elicit production of low density lipoprotein (LDL) receptors in mice. Recombinant adenoviruses containing: 1) cDNA encoding the human LDL receptor (AdCMV-LDLR)(CMV,cytomegalovirus); 2) β-galactosidase (AdCMV-βgal); and firefly luciferase (AdCMV-Luc), were prepared using co-transfection of the appropriate plasmids in 293 cells.

Rosenfeld et al., 1991, *Science*, vol. 252, pp. 431–434, discloses adenovirus-mediated transfer of recombinant α1-antitrypsin gene to the lung epithelium cells of the cotton rat respiratory tract in vivo. The adenoviral vector contained an adenovirus major late promoter and a recombinant human α1-antitrypsin gene.

Quantin et al., 1992, *Proc. Natl. Acad. Sci. USA*, vol. 89, pp. 2581–2584, discloses a recombinant adenovirus containing the β-galactosidase reporter gene under the control of muscle-specific regulatory sequences. This recombinant virus directed expression of the β-galactosidase in myotubes in vivo.

Problems associated with adenovirus infection, particularly those associated with repression of host cell mRNA translation and shutdown of host normal mRNA production (Babich et al., 1983, *Mol. Cell. Biol.*, vol. 3, pp. 1212–1221; Beltz et al., 1979, *J. Mol. Biol.*, vol. 131, pp. 353–373; Schneider et al., 1987, *Annu. Rev. Biochem.*, vol. 56, pp. 317–332) have been addressed by using defective adenovirus vectors which are based on mutations in the dominant regulatory region, E1 (Harrison et al., 1977, *Virology*, vol. 77, pp. 319–329; Jones et al., 1979, *Cell*, vol. 17, pp. 583–689). In addition, conventional adenovirus vector systems typically require high cell exposure (e.g., MOI's in excess of 500 PFU/cell) for expression of the desired gene, which is detrimental to the cells because of cytopathic effects from exposure. Therefore, a need exists for an adenovirus-mediated expression vector which can infect cells at low doses, yet can exhibit maximum expression of a gene in the cell.

Moreover, although adenovirus-based vectors for gene expression have been successfully employed with a number of mammalian and viral genes (for review, see Mulligan, R. C., 1993, *Science*, vol. 260, pp. 926–932), they have not apparently been used to express any member of the guanine nucleotide-binding protein coupled receptors (GPCR) family, such as the pituitary thyrotropin-releasing hormone (TRH-R)(Straub et al., 1990, *Proc. Natl. Acad. Sci U.S.A.*, vol. 87, pp. 9514–9518; Yamada et al., 1992, *Biochem. Biophys. Res. Commun.*, vol. 184, pp. 367–372; Zhao et al., 1992, *Endocrinology*, vol. 130, pp. 3529–3536; de la Pena et al., 1992, *Biochem. J.*, vol. 284, pp. 891–899). Seven transmembrane-spanning GPCRs comprise a large family of cell surface regulatory proteins (Dohlman et al., 1991, *Annu. Rev. Biochem.*, vol. 60, pp. 653–688). When studying the molecular details of receptor biology in mammalian cells, expression of wild type and mutant receptors is usually accomplished by gene transfer by one of several transfection procedures.

Assays using 1) a cell system that permits intracellular replication of the plasmid vector during transient expression studies; or 2) transfectants that stably express the receptor of interest, provide useful, but, limited receptor expression. Where transfections yield low levels of receptor expression, or where the range of cell types that can be transfected is restricted, studies of these receptors is limited. Adenovirus-mediated gene transfer could be employed as an alternative strategy to plasmid based receptor expression vectors. A significant advantage of using adenovirus-mediated gene transfer is the wide variety of cells which are susceptible to infection by adenovirus. This should permit study of TRH-R biology in a variety of mammalian cell types, including those not amenable to transfection techniques.

Furthermore, the analysis of elements involved in cardiac myocyte gene regulation would be greatly facilitated by a simple and efficient method of adenovirus-mediated gene transfer. Because there are no permanent cardiac myocyte cell lines, the majority of cardiac myocyte gene expression studies have been carried out using transient gene transfer techniques into primary cultures of fetal and neonatal cardiocytes (Gustafson et al., 1987, *Proc. Natl. Acad. Sci. U.S.A.*, vol. 84, pp. 3122–3126). Although useful, this methodology has many limitations, including relatively low efficiency as well as being restricted to fetal and neonatal stages of development since transient transfection of adult cardiac myocytes has not been reported.

As an alternative, in vitro studies of cardiac myocyte gene regulation and gene transfer have been successfully carried out in transgenic (Rindt et al., 1993, *J. Biol. Chem.*, vol. 268, pp. 5332–5338; and Subramanian et al., 1991, *J. Biol. Chem.*, vol. 266, pp. 24613–24620). However, the generation of transgenic mouse lines is both costly and extremely time consuming.

A second approach to cardiac gene transfer in vitro has relied on injecting plasmid DNA into the myocardium and measuring reporter gene expression in the cells which have successfully taken up sufficient quantities of DNA (Kitsis et al., 1991, *Proc. Natl. Acad. Sci. U.S.A.*, vol. 88, pp. 4138–4142; Lin et al., 1990, *Circulation*, vol. 82, pp. 2217–2221; and Ascadi et al., 1991, *The New Biologist*, vol. 3, pp. 71–81). The problem associated with direct DNA injection is its relative inefficiency as only approximately 0.02% of the myocytes in the adult rat heart take up and express injected DNA (Kitsis et al., 1993, in *Methods in Molecular Genetics*, ed. Adolph, K. W., Academic Press, Inc., New York, Vol. 1, pp. 374–392).

A recent report demonstrated efficient gene transfer into adult rat cardiocytes in vitro (Kirshenbaum et al., 1993, *J. Clin. Invest.*, vol. 92, pp. 381–387). In addition, recent studies using adenovirus vectors introduced intravenously into both rats and mice, indicate that the virus will infect a wide variety of tissue types, including mouse skeletal and cardiac muscle (Quantin et al., 1992, *Proc. Natl. Acad. Sci. U.S.A.*, vol. 89, pp. 2581–2584; and Strattford-Perricaudet et al., 1992, *J. Clin. Invest.*, vol. 90, pp. 626–630). However, little quantitative data is available concerning expression of adenovirus-mediated gene transfer in vivo. Therefor, a need exists for an adenovirus-mediated gene transfer vector system which would function effectively with primary cultures of cardiac myocytes and one which would also have application in vitro.

SUMMARY OF THE INVENTION

The primary object of the present invention is to provide an adenovirus-based expression system capable of expressing a heterologous gene(s) in a host mammalian cell.

The present invention provides a novel, highly efficient, recombinant adenovirus expression system for expression of a heterologous gene(s) and/or gene product(s) in a mammalian cell. The recombinant adenovirus expression system of the invention was produced via homologous recombination between the novel vector of the invention co-transfected with the large fragment of the adenovirus-5 genome in 293 cells.

In accordance with the present invention, the novel expression vector is preferably a plasmid vector. The plasmid vector of the invention can be used as a generic vector, that is, for the expression of any number of selected heterologous gene(s). The generic plasmid vector is designated pAdCMV-HS-Vector. The plasmid vector described herein can itself be transfected into a mammalian cell for the expression of any number of gene(s) and/or production of a gene product(s), depending on the heterologous gene(s) cloned into the plasmid vector. Alternatively, the plasmid vector can be converted into the recombinant adenovirus of the invention. Examples of various uses of the plasmid vector are described in the various embodiments disclosed herein.

In one embodiment of the invention, the plasmid vector includes at least one cDNA insertion site, i.e., restriction site(s) for cloning a selected heterologous gene(s). Positioned upstream of the gene insertion site(s) is a promoter which controls expression of the heterologous gene(s). The promoter is preferably the mouse cytomegalovirus (CMV) early promoter, or an effective expression promoting fragment thereof. Positioned upstream of the promoter, is the left end replication and packaging elements of the adenovirus-5 genome. A eukaryotic splice acceptor and splice donor site is positioned immediately downstream of the promoter.

Following the splicing sequence elements, is the gene insertion site(s), which is followed by the polyadenylation sequence, and the region for homologous recombination which contains a portion of the adenovirus-5 genome. The polyadenylation sequence preferably comprises the 3' processing site taken from the mouse β-globin transcription unit i.e., Globin poly(A). The order and choice of the splicing and polyadenylation elements results in optimal processing of the pre-mRNA into mRNA. The region for homologous recombination preferably is the adenovirus-5 genome nucleotide sequence 2800–5776.

The plasmid vector of the invention can be readily converted into a recombinant adenovirus for expression of a heterologous gene(s) and/or gene product(s) in a mammalian cell. Here, the plasmid vector is co-transfected with the large fragment of the adenovirus-5 genome i.e., 3.8–100 map units and/or an appropriate derivative thereof. Homologous recombination between these DNA fragments results in the production of a replication defective, recombinant adenovirus. The recombination reconstructs the adenovirus-5 genome by displacing the E1A and E1B protein coding regions with the plasmid vector cDNA.

In another embodiment of the invention, there is provided a recombinant adenovirus expression system for the receptor for thyrotropin-releasing hormone (TRH-R). The recombinant adenovirus, designated AdCMVmTRHR, circumvents difficulties encountered when using conventional transient or stable plasmid expression systems. Using this recombinant adenovirus (AdCMVmTRHR), TRH-Rs can be expressed in different mammalian cell types, including those resistant to transient transfection assay. Recombinant adenovirus, AdCMVmTRHR, was produced by homologous recombination between plasmid vector, designated pAdCMVmTRHR, i.e. the generic plasmid vector of the invention containing the gene coding TRH-R, co-transfected with the large fragment of adenovirus-5 dl309 genome. The versatility of using adenovirus mediated gene transfer and expression of TRH-Rs not only facilitates in vitro studies of TRH-R biology, but provides a valuable in vivo expression vector capable of extending TRH-R studies in animal model systems.

In a further embodiment of the present invention, infection of cultured fetal and adult rat cardiac myocytes in vitro and of adult cardiac myocytes in vivo was characterized using the recombinant adenovirus of the invention. The recombinant adenovirus, designated AdCMVCATgD, includes the chloramphenicol acetyltransferase (CAT) reporter gene driven by the cytomegalovirus (CMV) promoter. Plasmid vector pAdCMVCATgD i.e., generic plasmid vector of the present invention containing the gene encoding the bacterial CAT sequence, was co-transfected with the large fragment of the adenovirus-5 genome (3.6–100 map units). Homologous recombination between the plasmid vector and adenovirus fragment produced the recombinant adenovirus, designated AdCMVCATgD.

Virtually all fetal or adult cardiocytes expressed the CAT gene in vitro when infected with 1 plaque forming unit (pfu) of virus per cell. Using in vitro studies as a guide, recombinant virus AdCMVCATgD was introduced directly into adult rat myocardium and the expression results obtained from virus injection was compared to those obtained by direct injection of plasmid vector pAdCMVCATgD DNA. The amount of CAT activity resulting from adenovirus infection of the myocardium is orders of magnitude higher than that seen from DNA injection and is proportional to the amount of input virus. The recombinant adenovirus-mediated gene delivery system is a very effective tool for high efficiency gene transfer into the cardiovascular system.

BRIEF DESCRIPTION OF THE DRAWINGS

FIG. 2 is a graphic map showing the structure of plasmid vector pGEM2AdCMV.

FIG. 19 is a graph showing distribution of CAT activity in cells of AdCMVCATgD injected hearts.

FIG. 20B is a graph showing CAT expression over time in the left ventricle following injection of $6 \times 10^7$ pfu of AdCMVCATgD virus.

FIG. 22 is a schematic showing the nucleotide sequence of plasmid vector pAdCMV-HS-Vector, as shown in FIGS. 1(a) & 1(b).

DETAILED DESCRIPTION OF THE INVENTION

Figure 1A:
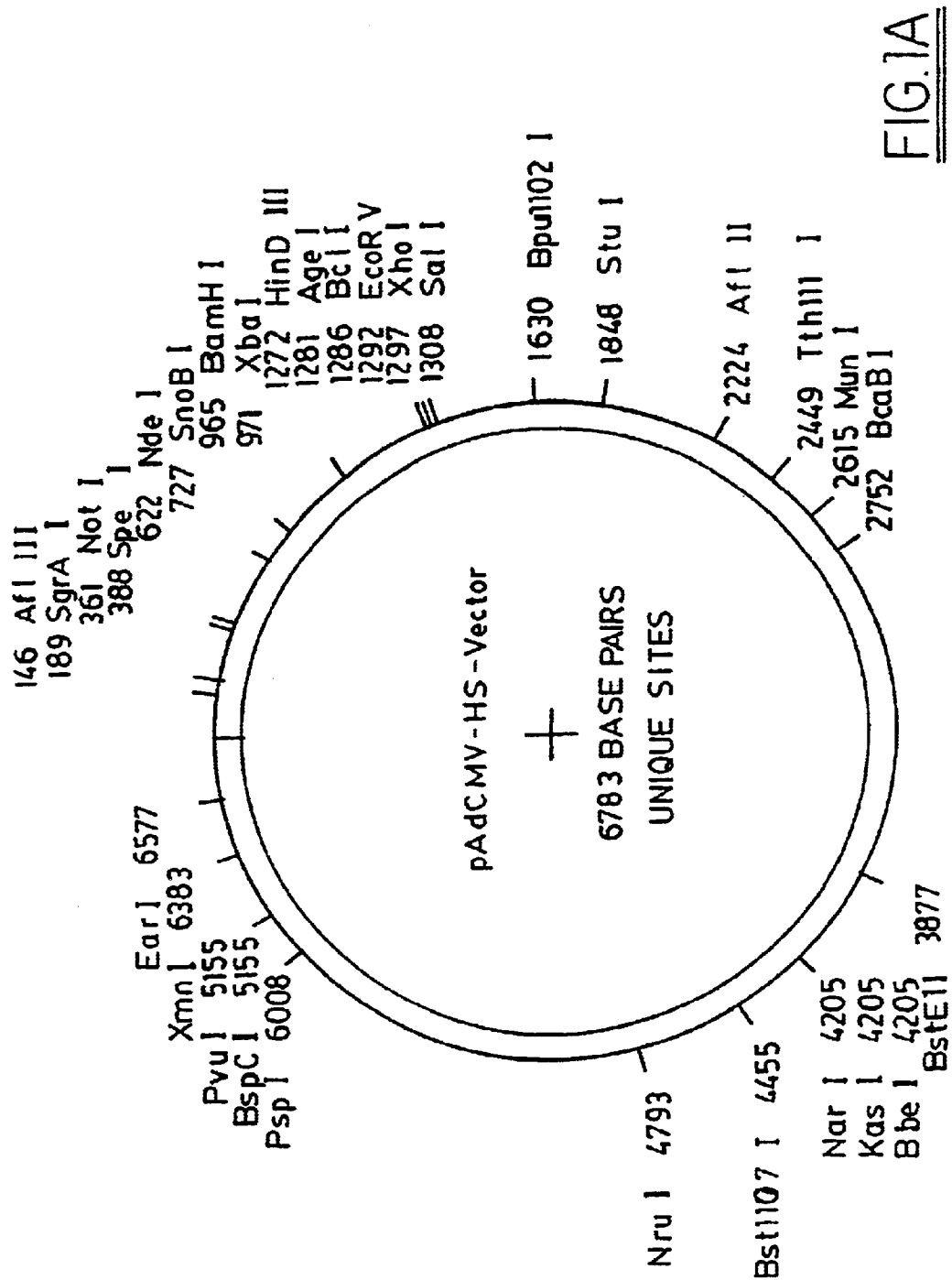
FIGS. 1(*a*) & 1(*b*) is a graphic map showing the structure of the generic plasmid vector of the invention, designated pAdCMV-HS-Vector.

As used throughout this specification, the following definitions apply for purposes of the present invention:

The term "restriction enzyme digestion" of DNA refers to catalytic cleavage of the DNA with an enzyme that acts only at certain locations in the DNA. Such enzymes are called restriction endonuclease, and the sites for which each is specific is called a restriction site. The various restriction enzymes used herein are commercially available and their reaction conditions, cofactors, and other requirements as established by the enzyme suppliers are used. Restriction enzymes commonly are designated by abbreviations composed of a capital letter followed by other letters representing the microorganism from which each restriction enzyme originally was obtained and then a number designating the particular enzyme. In general, about 1 μg of plasmid or DNA fragment is used without 1–2 units of enzyme in about 20 μl of buffer solution. Appropriate buffers and substrate amounts for particular restriction enzymes are specified by the manufacturer. Incubation of about 1 hour at 37° C. is ordinarily used, but may vary in accordance with the supplier's instructions. After incubation, protein or polypeptide is removed by extraction with phenol and chloroform, and the digested nucleic acid is recovered from the aqueous fraction by precipitation with ethanol. Digestion with a restriction enzyme may be followed with bacterial alkaline phosphatase hydrolysis of the terminal 5' phosphates to prevent the two restriction cleaved ends of a DNA fragment from circularizing or forming a closed loop that would impede insertion of another DNA fragment at the restriction site. Unless otherwise stated, digestion of plasmids is not followed by 5' terminal dephosphorylation. Procedures and reagents for dephosphorylation are conventional as described in Sections 1.56–1.61 of Sanbrook, et.al., *Molecular Cloning: A Laboratory Manual* New York: Cold Spring Harbor Laboratory Press, 1989, which disclosure is hereby incorporated by reference).

The term "recovery" or "isolation" of a given fragment of DNA from a restriction digest means separation of the digest on polyacrylamide or agarose gel by electrophoresis, identification of the fragment of interest by comparison of its mobility versus that of marker DNA fragments of known molecular weight, removal of the gel section containing the desired fragment, and separation of the gel from DNA. These procedures are generally well known. For example, see Lawn et al., 1981, *Nucleic Acids Res.*, vol. 9, pp. 6103–6114; and Goeddel et al., 1980, *Nucleic Acids Res.*, vol. 8, p. 4057, which disclosures are hereby incorporated by reference.

The term "expression" may be characterized as follows: A cell is capable of synthesizing many proteins. At any given time, many proteins which the cell is capable of synthesizing are not being synthesized. When a particular polypeptide, coded for by a given gene, is being synthesized by the cell, that gene is said to be expressed. In order to be expressed, the DNA sequence coding for that particular polypeptide must be properly located with respect to the control region of the gene. The function of the control region is to permit the expression of the gene under its control.

The term "southern blot analysis" is a method by which the presence of DNA sequences in a restriction endonuclease digest of DNA or DNA-containing composition is confirmed by hybridization to a known, labeled oligonucleotide or DNA fragment. Southern analysis typically comprises electrophoretic separation of DNA digests on agarose gels, denaturation of the DNA after electrophoretic separation, and transfer of the DNA to nitrocellulose, nylon, or another suitable membrane supports for analysis with a radiolabeled, biotinylated or enzyme-labeled probe as described in sections 9.37–9.52 of Sambrook et al., supra, which disclosure is hereby incorporated by reference.

The term "northern analysis" is a method used to identify RNA sequences that hybridize to a known probe such as an oligonucleotide, DNA fragment, cDNA or fragment thereof, or RNA fragment. The probe is labeled with a radioisotope such as $^{32}P$, or by biotinylation, or with an enzyme. The RNA to be analyzed is usually electrophoretically separated on an agarose or poly-acrylamide gel, transferred to nitrocellulose, nylon, or other suitable membrane, and hybridized with the probe, using standard techniques well known in the art, such as those described in sections 7.39–7.52 of Sambrook et al., supra, which disclosure is hereby incorporated by reference.

The term "vector" refers to an extra-chromosomal molecule of duplex DNA comprising an intact replicon that can be replicated in a cell. Generally, vectors are derived from viruses or plasmids of bacteria and yeasts. An adenovirus vector comprises an adenovirus replicon.

The term "gene" refers to those DNA sequences which transmit the information for and direct the synthesis of a single protein chain.

The term "infection" refers to the invasion by agents (e.g., viruses, bacteria, etc.) of cells where conditions are favorable for their replication and growth.

The term "heterologous gene" in reference to the adenovirus vectors hereof, refers to DNA that encodes polypeptides ordinarily not produced by the virus from which the vector is derived, but which is introduced into the cell as recombinant DNA or within viruses carrying recombinant DNA genomes.

The term "plasmid" means a bacterial vector which is used as an intermediate in the construction of a virus vector. A plasmid facilitates the transfer of exogenous genetic information, such as the combination of a novel promoter and a heterologous structural gene under the regulatory control of that promoter, to a specific site within the viral genome by homologous recombination via the DNA sequences flanking the chimeric gene. The plasmid can itself express a heterologous gene inserted therein.

"Plasmids" are designated by a lower case p preceded and/or followed by capital letters and/or numbers. The starting plasmids herein are commercially available, are publicly available on an unrestricted basis, or can be constructed form such available plasmids in accord with published procedures. In addition, other equivalent plasmids are known in the art and will be apparent to one of ordinary skill in the art.

The term "ligation" means the process of forming phosphodiester bonds between two nucleic acid fragments. To ligate the DNA fragments together, the ends of the DNA fragments must be compatible with each other. In some cases, the ends will be directly compatible after endonuclease digestion to blunt ends to make them compatible for ligation. To blunt the ends, the DNA is treated in a suitable buffer for at least 15 minutes at 15° C., with about 10 units of the Klenow fragment of DNA polymerase I or T4 DNA polymerase in the presence of the four deoxyribonucleotide triphosphates. The DNA is then purified by phenolchloroform extraction and ethanol precipitation. The DNA fragments that are to be ligated together are put in solution in about equimolar amounts. The solution will also contain ATP, ligase buffer, and a ligase such as T4 DNA ligase at about 10 units per 0.5 g of DNA. If the DNA is to be ligated into a vector, the vector is first linearized by digestion with the appropriate restriction endonuclease(s). The linearized fragment is then treated with bacterial alkaline phosphatase, or calf intestinal phosphatase to prevent self-ligation during the ligation step.

"Preparation" of DNA from cells means isolating the plasmid DNA from a culture of the host cells. Commonly used methods for DNA preparation are the large and small scale plasmid preparations described in sections 1.25–1.33 of Sambrook et al., supra, which disclosure is hereby incorporated by reference. After preparation of the DNA, it can be purified by methods well known in the art such as that described in section 1.40 of Sambrook et al., supra, which disclosure is hereby incorporated by reference.

This invention achieves significantly enhanced in vitro and in vivo expression levels of heterologous gene(s) by inserting into a host mammalian cell the adenovirus expression system or plasmid vector of the invention, containing foreign cDNA encoding the heterologous gene(s) under the transcriptional control of DNA fragments derived from the mouse cytomegalovirus (CMV) immediate early gene regulatory sequences. It is understood that the CMV immediate early promoter can be combined with enhancer elements isolated from other transcriptional units to increase expression efficiency.

The recombinant adenovirus expression system and plasmid vector include at least one cDNA insertion site(s) i.e., restriction site(s) for cloning a selected heterologous gene (s). Other important features of the adenovirus expression system and plasmid vector of the invention include a highly efficient eukaryotic splicing sequence elements located immediately downstream the promoter, and a strong polyadenylation sequence following the heterologous gene insertion site.

In an alternative embodiment of the invention, the plasmid vector can be readily converted into the recombinant adenovirus expression system of the invention for expression of a heterologous gene(s) and/or gene product(s) in a mammalian cell. To produce the recombinant adenovirus, the plasmid vector of the invention is co-transfected with the large fragment of adenovirus-5 genome in 293 cells. Homologous recombination between these DNA fragments results in the production of a replication defective, recombinant adenovirus, which includes cDNA from the plasmid vector.

Host cells useful for expression of the heterologous gene(s) includes any mammalian cell in which the recombinant adenovirus and/or plasmid vector of the invention are capable of uptake and expression. The plasmid vector of the invention can be used to transfect a mammalian host cell for production of the inserted gene product. It is understood that the plasmid vector can be introduced into the host cell(s) using conventional techniques known in the art, such as, for example, transfection. The recombinant adenovirus can be introduced into the host cell via infection using standard techniques in the art.

The plasmid vector(s) and recombinant adenovirus(es) of this invention can be prepared using standard genetic engineering technologies known to the art, as described by Maniatis et al., 1982, *Molecular Cloning: A Laboratory Manual*, Cold Springs Laboratory, Cold Springs Harbor, N.Y.; and Sambrook et al., (*Molecular Cloning: A Laboratory Manual* New York: Cold Spring Harbor Laboratory Press, 1989, which disclosures are hereby incorporated by reference.

In a preferred embodiment of the invention, the plasmid vector of the invention comprises, starting from the left end of the adenovirus at position 1, adenovirus nucleotide sequence from 1–353 containing the origin of replication and the viral packaging sequence; adenovirus nucleotide sequence from 354–2800 was deleted and replaced with the CMV-1 promoter, eukaryotic splice elements, the cDNA encoding the selected heterologous gene(s) and the Globin poly(A) site; and adenovirus nucleotide sequence from nucleotide 2800–5776,which serves as the region for homologous recombination.

To obtain efficient expression of the heterologous gene(s), a eukaryotic promoter must be present in the plasmid vector and recombinant adenovirus expression system. It is understood that any known eukaryotic promoter can be utilized in the plasmid vector and/or recombinant adenovirus expression system of the invention provided the promoter is capable of expressing the heterologous gene(s). The promoter used herein, preferably, is the mouse cytomegalovirus-1 early promoter, or an effective expression promoting fragment thereof. For an example of the CMV promoter, see U.S. Pat. No. 4,963,481 to Jean P. deVilliers, which disclosure is hereby incorporated by reference. The use of the mouse CMV promoter is of broad utility because this promoter has a very broad host range and functions with superior strength and efficiency in a wide variety of cell lines tested.

The presence and position of the splicing elements with respect to the cDNA are important to overall processing efficiency, as is the choice of splicing elements. In the present invention, a hybrid splice donor and acceptor was used which yielded a highly efficient processing activity compared to the more common splice element used in other systems i.e., the SV40 small T splice site. By inserting the cDNA downstream of the splice elements, we are coupling the splice elements to the downstream 3' processing site generating a terminal exon. Use of a demonstrably efficient poly(A) site maximizes efficiency of the expression system. This allows efficient conversion of pre-mRNA into mRNA and allows the system to take full advantage of the high level of expression generated by the CMV promoter.

Any of the conventional cloning methods for insertion of the gene and/or gene fragment(s) into the plasmid vector can be used to ligate the promoter and the other control elements into specific sites within the plasmid vector. Accordingly, heterologous gene sequence(s) containing those regions coding for the gene(s) can be ligated into the plasmid vector at a specific restriction site in relation to the promotor and control elements so that when either the recombinant adenovirus or plasmid vector is introduced into the mammalian cell, the foreign genetic sequence can be expressed (i.e., transcribed and translated) by the host cell.

Another important feature of the adenovirus expression system and plasmid vector of the invention, is the ability to express more than one heterologous gene, simultaneously. Using the expression systems of the invention, it is possible to express at least two heterologous genes at the same time. The second heterologous gene, is preferably inserted into the Not1 restriction site in the plasmid vector. However, it is understood that other restriction sites positioned between the packaging sequence and the promoter are available for insertion of the second gene.

As previously mentioned, the plasmid vector can be introduced into an appropriate host cell (i.e., mammalian cells) by transfection, and the recombinant adenovirus can be introduced by infection. Stable transformants can be selected based upon the expression of one or more appropriate gene markers either present or inserted into the adenovirus plasmid, such as, for example, G418 resistance in eukaryotic host systems. Expression of such marker genes should indicate that the recombinant DNA molecule is integrated and functional. It is understood that any known gene marker in the art can be utilized herein. Such gene markers can be derived from cloning vectors, which usually contain a marker function.

The plasmid vector and recombinant adenovirus containing the heterologous gene(s) can be identified by three approaches: (1) DNA-DNA hybridization using probes comprising sequences that are homologous to the gene(s); (2) presence or absence of "marker" gene function and (3) expression of inserted sequences based on physical, immunological or functional properties. Once a recombinant which expresses the gene is identified, the gene product should be analyzed. One goal of the invention is to use the plasmid vector and recombinant adenovirus expression system for gene expression and/or gene transfer in mammalian cells. Once the recombinant virus or plasmid is identified, it is cultured under conditions which facilitate growth of the cells and expression of the gene as will be apparent to one skilled in the art. Thereafter, the gene product can be isolated and purified by standard methods including chromatography (e.g., ion exchange, affinity, and sizing column chromatography), centrifugation, differential solubility, or by any other standard techniques.

The protein(s) encoded by the heterologous gene(s) inserted into the plasmid vector and recombinant adenovirus expression system can comprise any known protein, including; growth hormone, human growth hormone (HGH), des-N-methionyl human growth hormone, bovine growth hormone, parathyroid hormone, thyroxine, insulin A-chain, insulin B-chain, proinsulin, relaxin A-chain, relaxin B-chain, prorelaxin, follicle stimulating hormone (FSH), thyroid stimulating hormone (TSH), leutinizing hormone (LH), glycoprotein hormone receptors, calcitonin, glucagon, factor VIII, an antibody, lung surfactant, urokinase, streptokinase, human tissue-type plasminogen activator (t-PA), bombesin, factor IX, thrombin, hemopoietic growth factor, tumor necrosis factor-alpha and -beta, enkephalinase, human serum albumin, mullerian-inhibiting substance, mouse gonadotropin-associated peptide, β-lactamase, tissue factor protein, inhibin, activin, vascular endothelial growth factor, integrin receptors, thrombopoietin, protein A or D, rheumatoid factors, NGF-β platelet-growth factor, transforming growth factor; TGF-alpha and TGF-beta insulin-like growth factor-I and -II, insulin-like growth factor binding proteins, CD-4, DNase, latency associated peptide erythropoietin, osteoinductive factors, interferon, alpha, -beta, and -gamma, colony stimulating factors (CSFs), M-CSF, GM-CSF, and G-CSF, interleukins (ILs), IL-1, IL-2, IL-3, IL-4, IL-6, IL-7, superoxide dismutase; viral antigens; HIV envelope proteins GP120 and GP140, immuno globulins, and fragments of the above listed proteins.

The following Examples are provided to further illustrate the present invention.

EXAMPLE I

Construction of pGEM2AdCMV

Plasmid pBstSK+ (0–353) contains adenovirus-5 sequence from nt 0–353 inserted into pBstSK+ vector at the EcoRI site and the SstII site (which has been lost by blunt end ligation). These sequences are required viral elements which include the origin for DNA replication and the viral packaging sequence. The CMV enhancer/promoter was taken from the plasmid CDM8 (INVITROGEN) by digestion with HindIII and HincII. NotI linkers were added to the HincII site followed by digestion with NotI and SstI. Isolation of the resulting 592 bp fragment (CDM8 numbers 1533–2192) and insertion into pBstSK+ 0–353 vector at the NotI and SstI sites gave the plasmid pBstSK+ 0–353-CMV. The EcoRI-SstI fragment was isolated and inserted into the EcoRI-SstI sites of pGEM 2 vector to generate pGEM2AdCMV, as shown in FIG. 2. This construct has a polylinker from SstI to HindIII available for cloning.

EXAMPLE II

Construction of pMLSISCATgD

Figure 3:
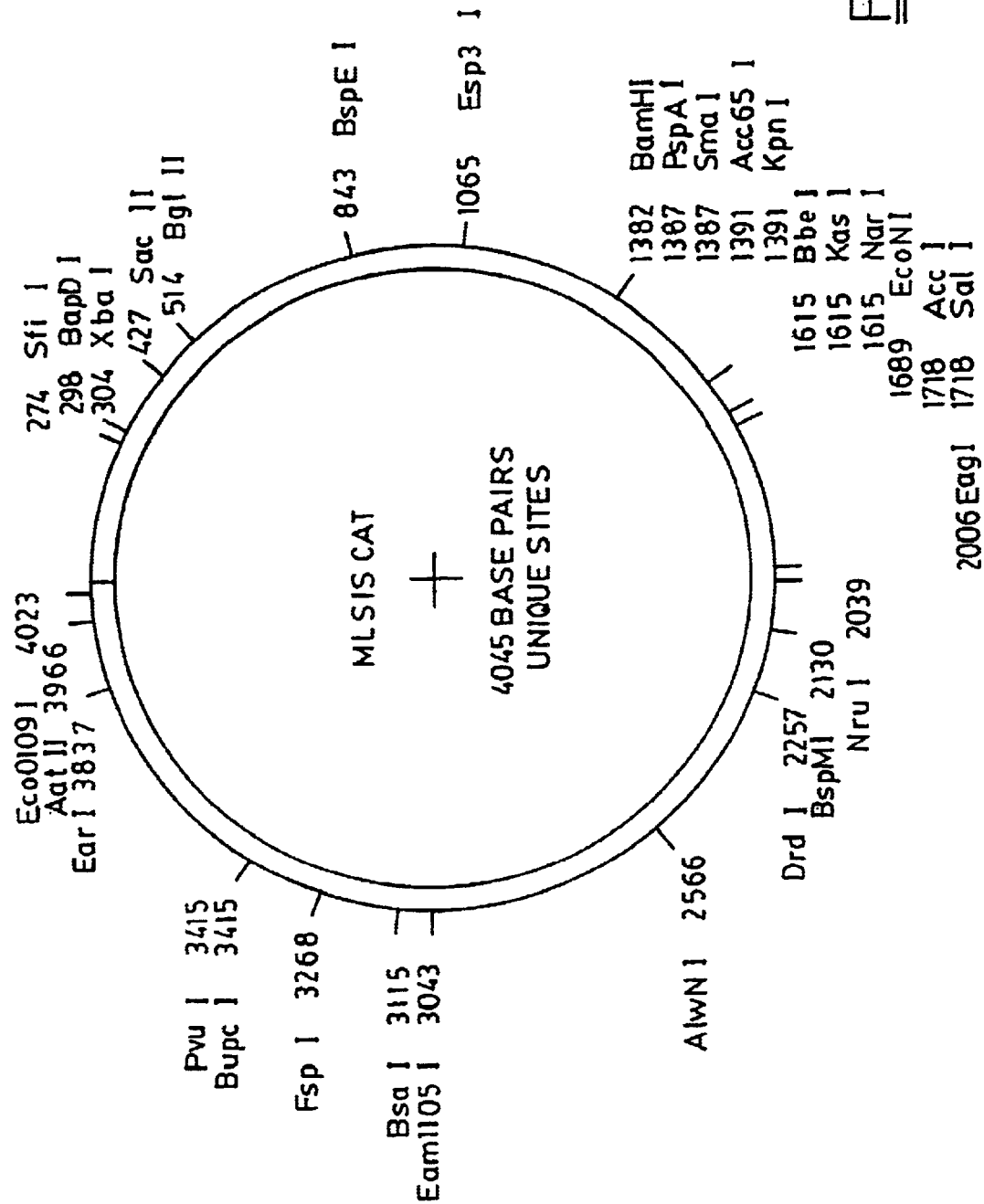
FIG. 3 is a graphic map showing the structure of plasmid vector ML SIS CAT.
Figure 4:
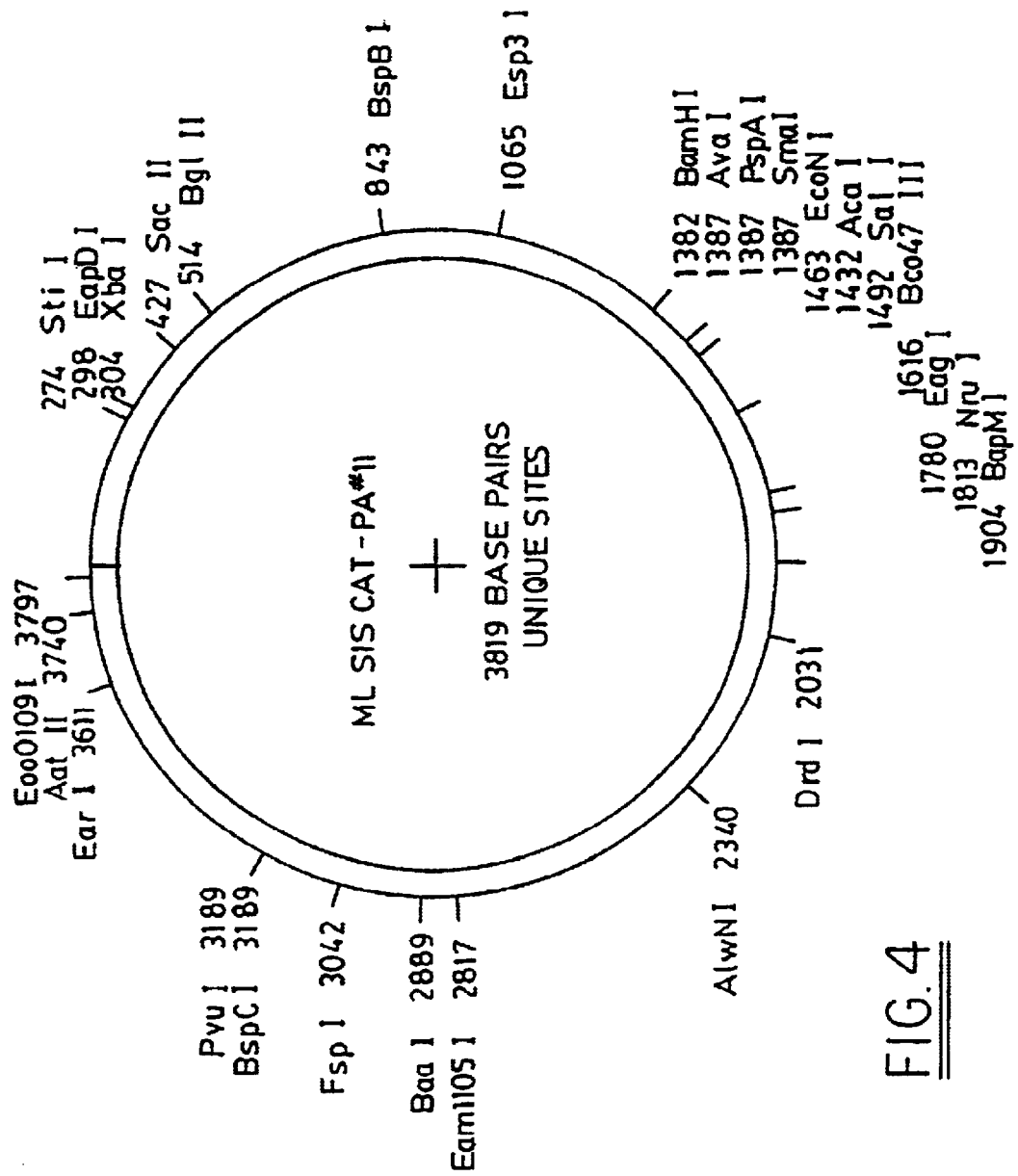
FIG. 4 is a graphic map showing the structure of plasmid vector ML SIS CAT-PA #11.
Figure 5:
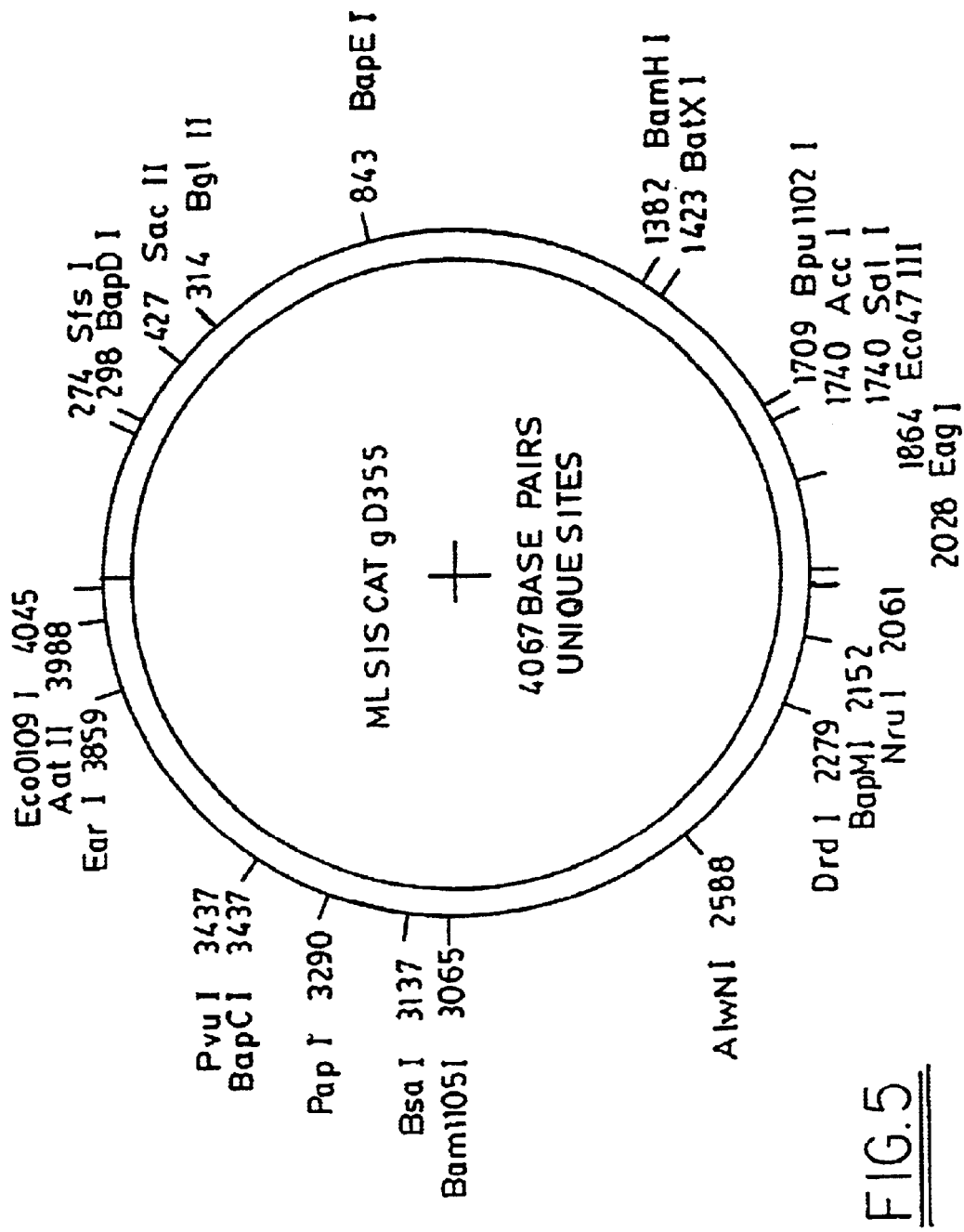
FIG. 5 is a graphic map showing the structure of plasmid vector ML SIS CAT gD355.

The SV40 poly A site was deleted from vector pMLSIS-CAT (FIG. 3)(Huang et al., 1990, NAR, vol. 18, pp. 937–947, which disclosure is hereby incorporated by reference) by NarI-KpnI digestion and blunt end circularization of the plasmid to make pMLSISCAT(-pA). The mouse β-major globin poly A site was isolated by NarI-SalI digestion of pMLgDø. This fragment was blunt end inserted into the BamHI site of pMLSISCAT(-pA) (FIG. 4) to create pMLSISCATgD (FIG. 5).

EXAMPLE III

Figure 11:
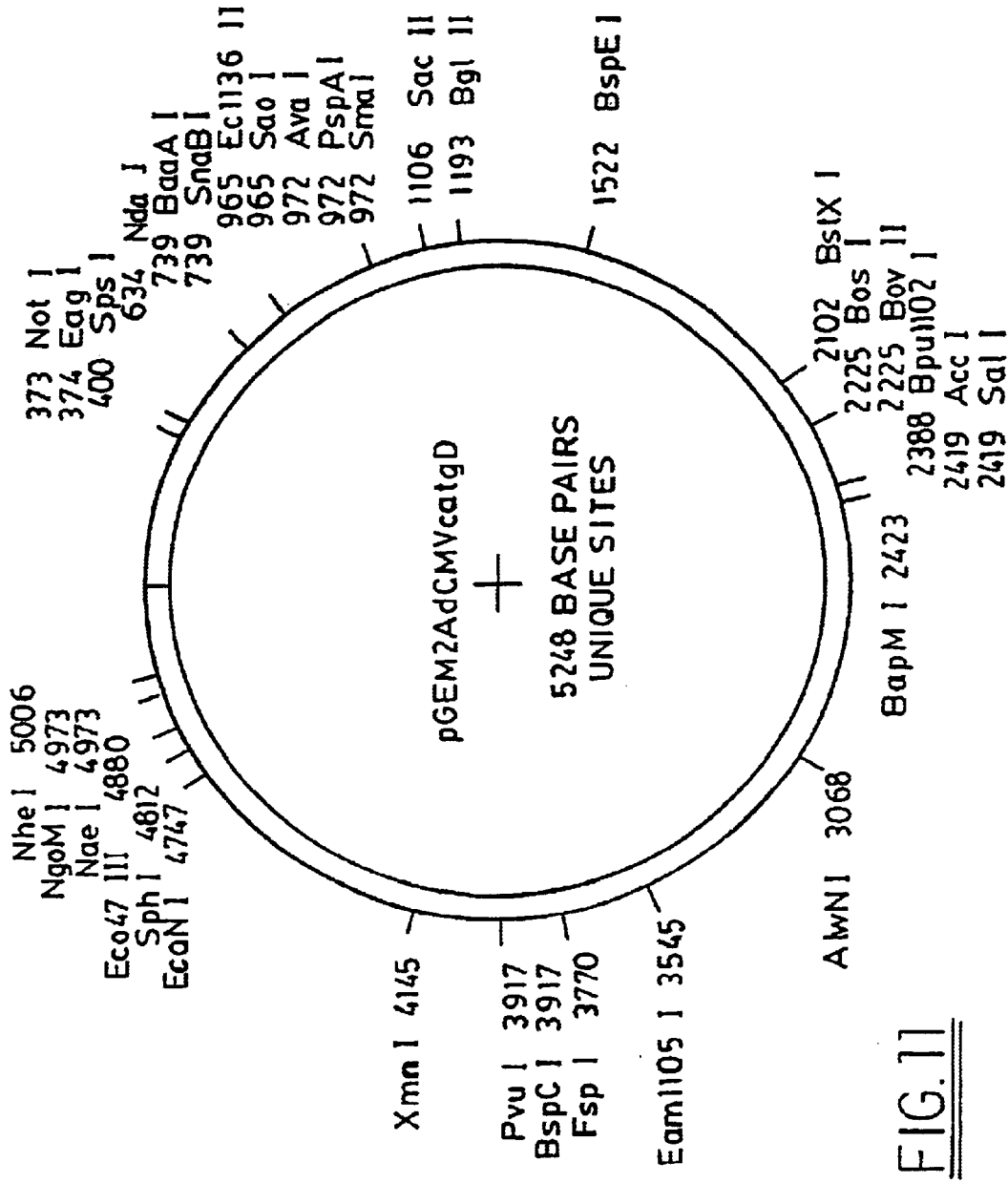
FIG. 11 is a graphic map showing the structure of plasmid vector pGEM2AdCMVcatgD.
Figure 12:
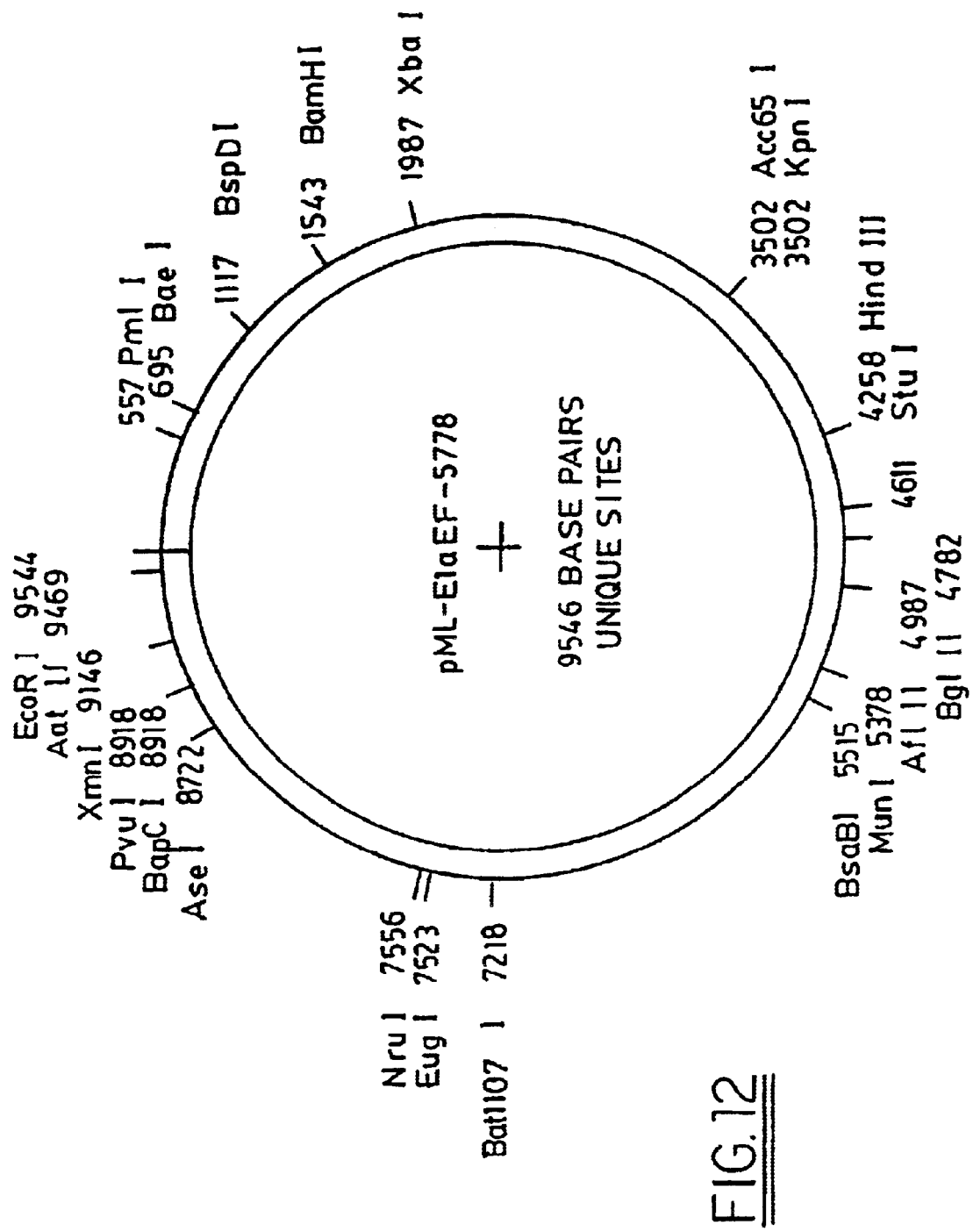
FIG. 12 is a graphic map showing the structure of plasmid vector pML-E1aEF-5778.

Construction of pAdCMVCatD pGEM2AdCMV (FIG. 2) was digested with XbaI; pMLSISCATgD (FIG. 5) was digested with XbaI and the fragment containing the splicing elements, the coding sequence for CAT and the globin poly(A) site was isolated and inserted into the XbaI site of pGEM2AdCMV to create pGEM2AdCMVCatgD (FIG. 11). pGEM2AdCMVCatgD was digested with PvuI and SalI and the coding plasmid was isolated and inserted into vector pMLP6gEF also cut with PvuI and SalI. The plasmid was constructed into an intact replication defective adenovirus by co-transfecting the plasmid vector with the 3.6–100 m.u. large fragment of adenovirus in 293 cells.

EXAMPLE IV

Construction of pAdCMVdHCatgD

Figure 6:
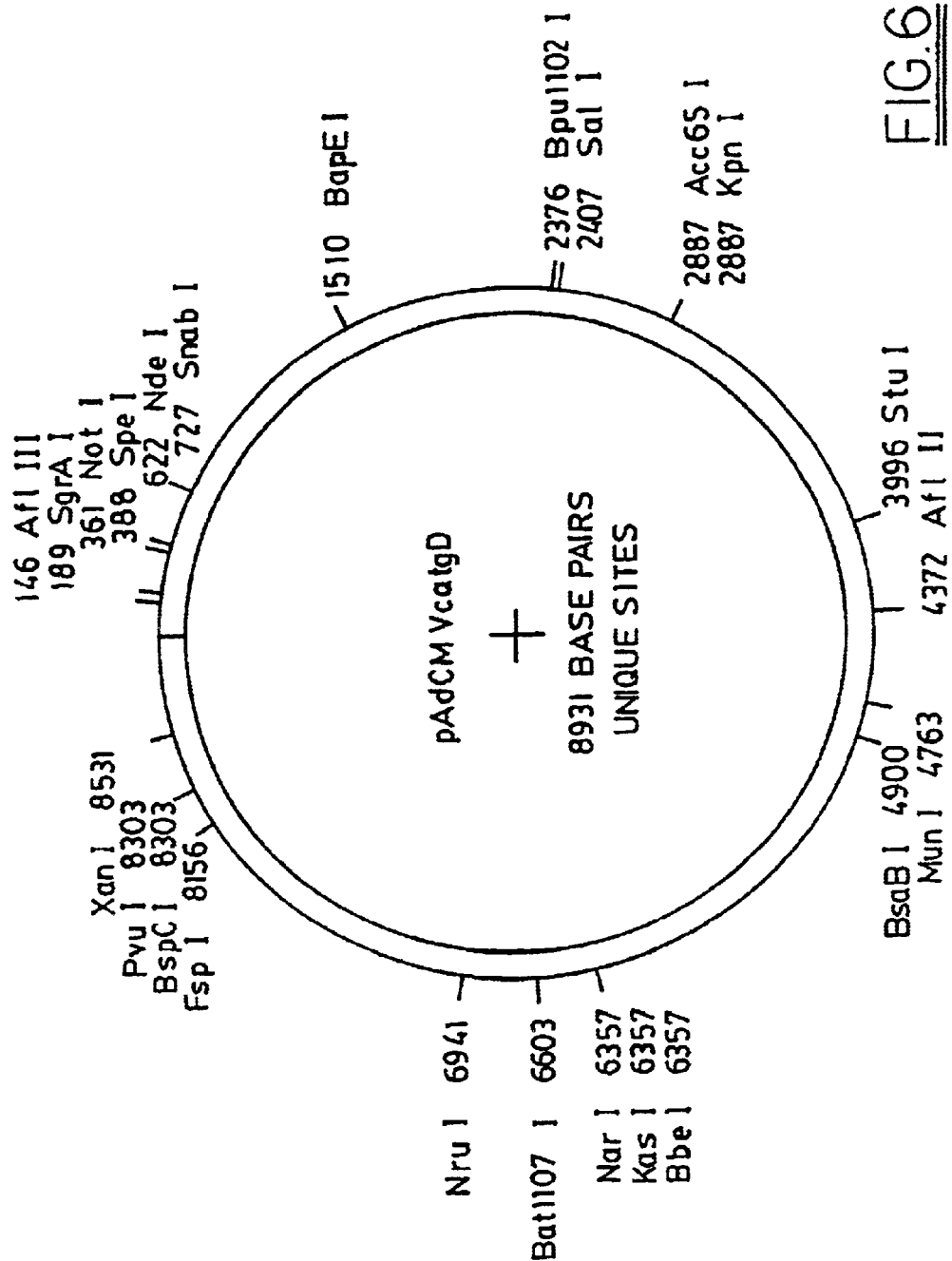
FIG. 6 is a graphic map showing the structure of plasmid vector pAdCMVCATgD.
Figure 7:
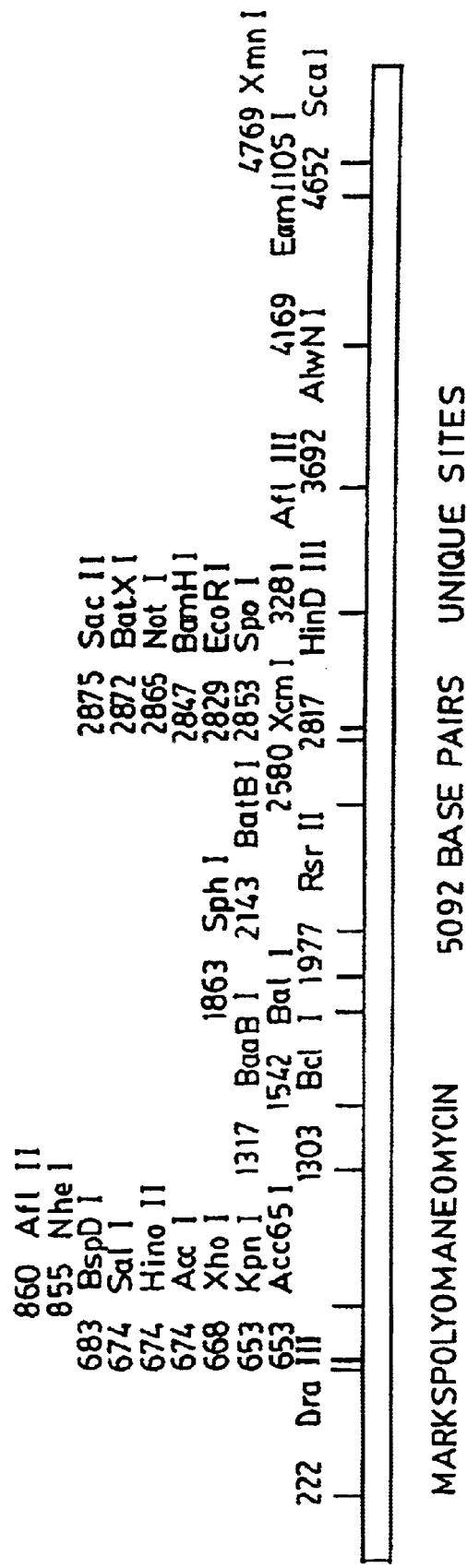
FIG. 7 is a graphic map showing the structure of plasmid vector pPYNeo.
Figure 8:
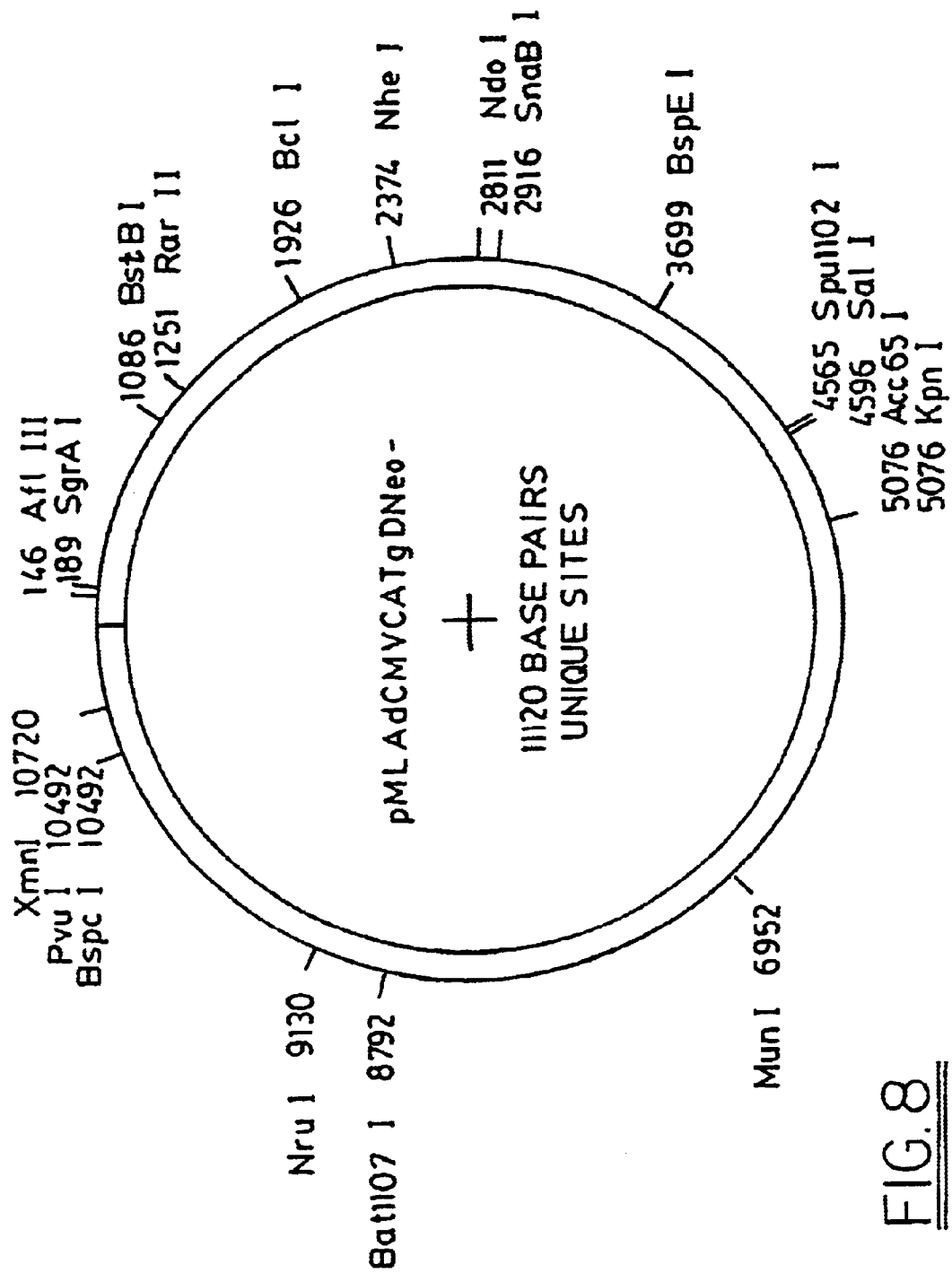
FIG. 8 is a graphic map showing the structure of plasmid vector pMLAdCMVCATgDNeo-.

One of the three HindIII restriction sites in pAdCMV-CatgD (FIG. 6) was deleted by partial HindIII digestion and filling by Klenow large fragment of DNA polymerase followed by plasmid circularization and ligation. This allowed removal of the CAT sequence and the poly(A) site by HindIII digestion, with the retention of promoter and splicing sequences. A 1100 bp of E1B sequence was deleted.

EXAMPLE V

Construction of pAdCMVCatgDNeo(−)

The unique restriction site NotI located at position 361 can be used to insert any additional gene of interest. As a test construct a NotI fragment from pPYNeo was isolated which contained the Neomycin resistance gene driven by the polyoma promoter and using the SV40 splicing and polyadenylation elements. This strategy resulted in the introduction of the Neo gene into the vector in two orientations relative to the direction of CAT gene expression (+) and (−). Both of these constructs were used in virus constructions, however, only the AdCMVCatDNeo(−) virus has been isolated to date.

EXAMPLE VI

Construction of pAdCMVTRHrE3

Figure 9:
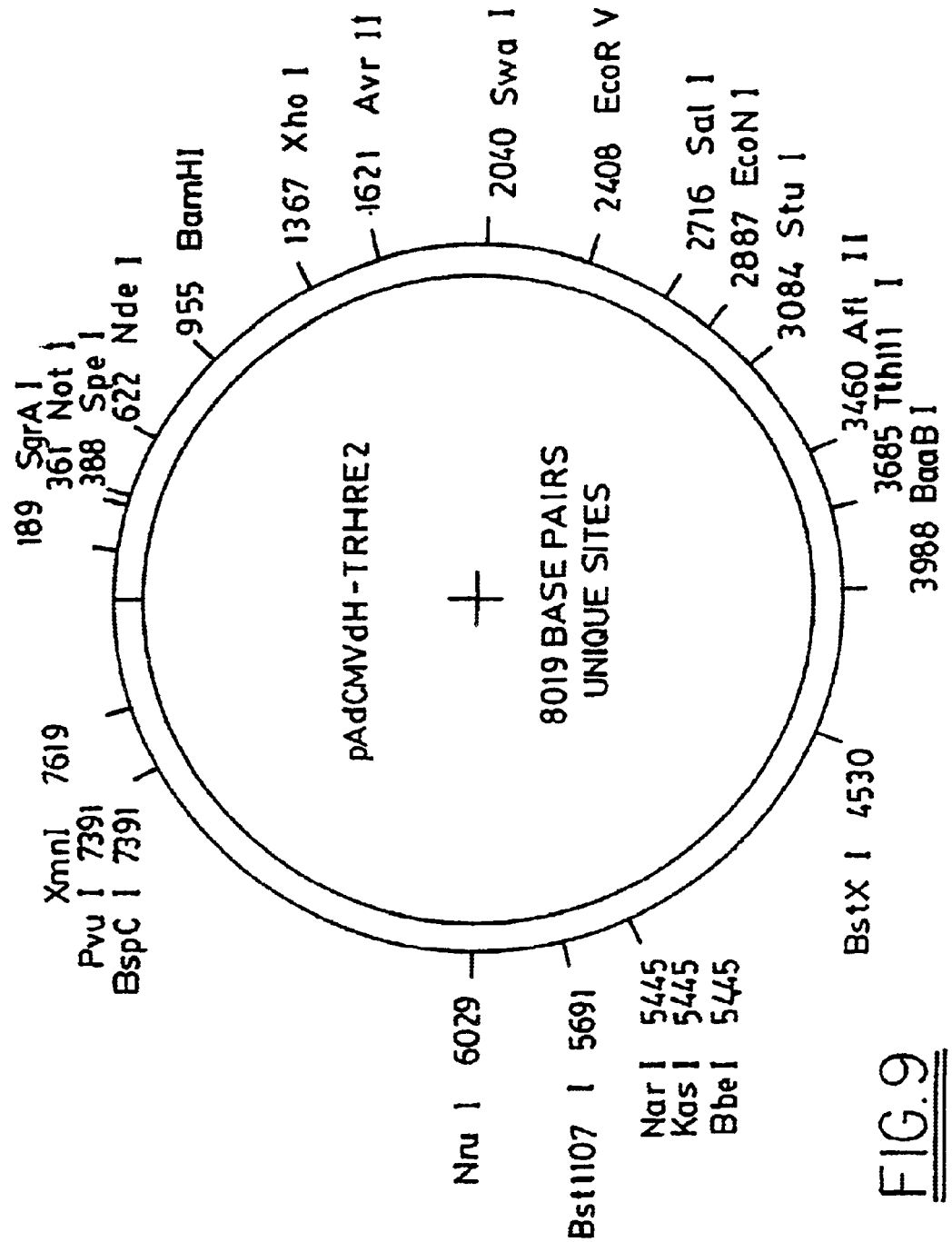
FIG. 9 is a graphic map showing the structure of plasmid vector pAdCMVdH-TRHRE2.
Figure 10:
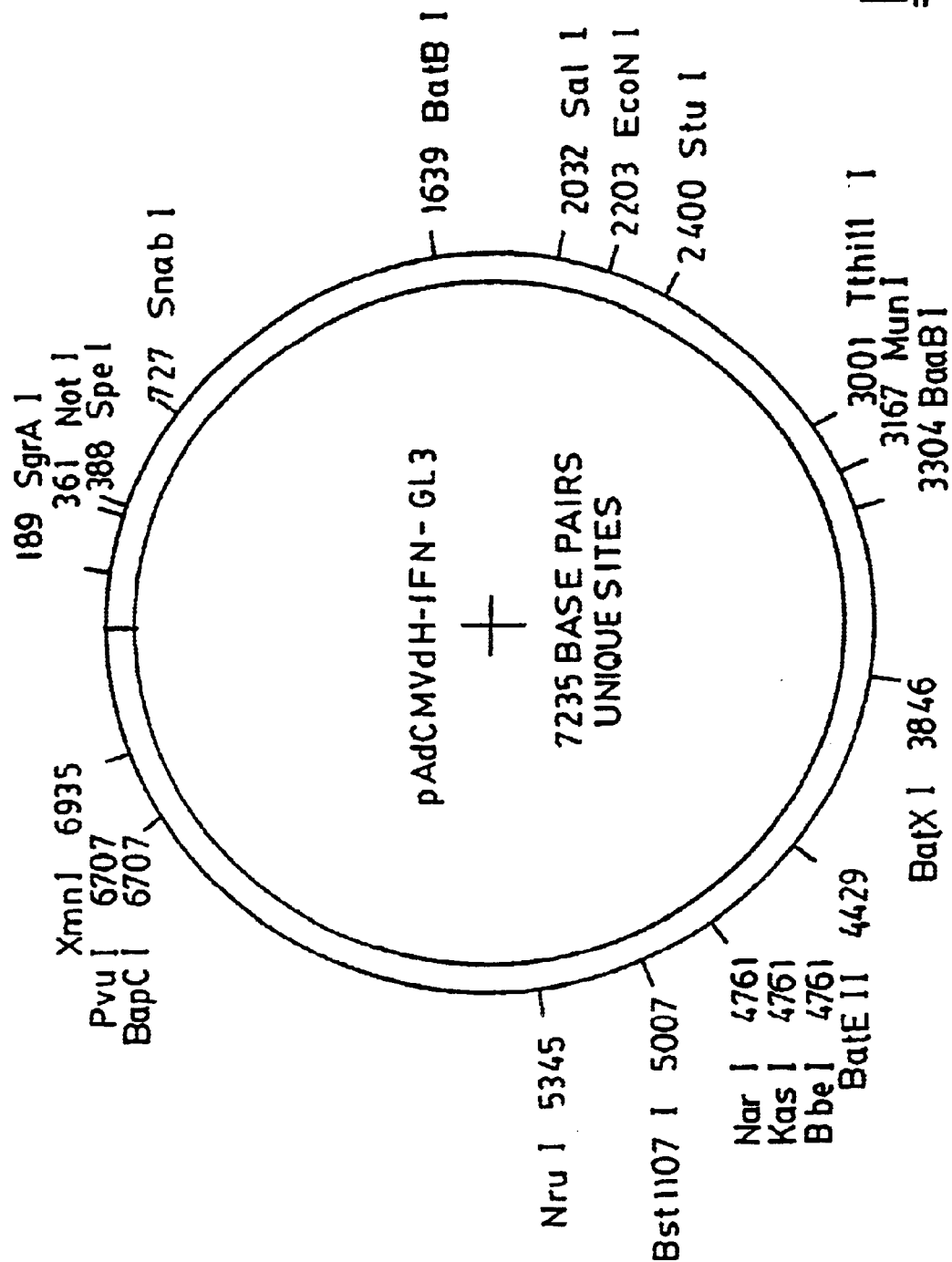
FIG. 10 is a graphic map showing the structure of plasmid vector pAdCMVdH-IFN-GL3.

Using vector pAdCMVdHCatgD (FIG. 6), cDNA for thyrotropin releasing hormone receptor (which contains the adenovirus E2 poly(A) site) was inserted directly into the HindIII digested vector to construct vector pAdCMVTRHrE3 (FIG. 9).

EXAMPLE VII

Construction of pAdCMV-Gamma Interferon L3

The cDNA for gamma interferon (with the added poly(A) site from adenovirus major late L3) was inserted into the pAdCMVdHCatgD (FIG. 6) HindIII digested vector to construct vector pAdCMVdH-IFN-GL3.

EXAMPLE VIII

Figure 1B:
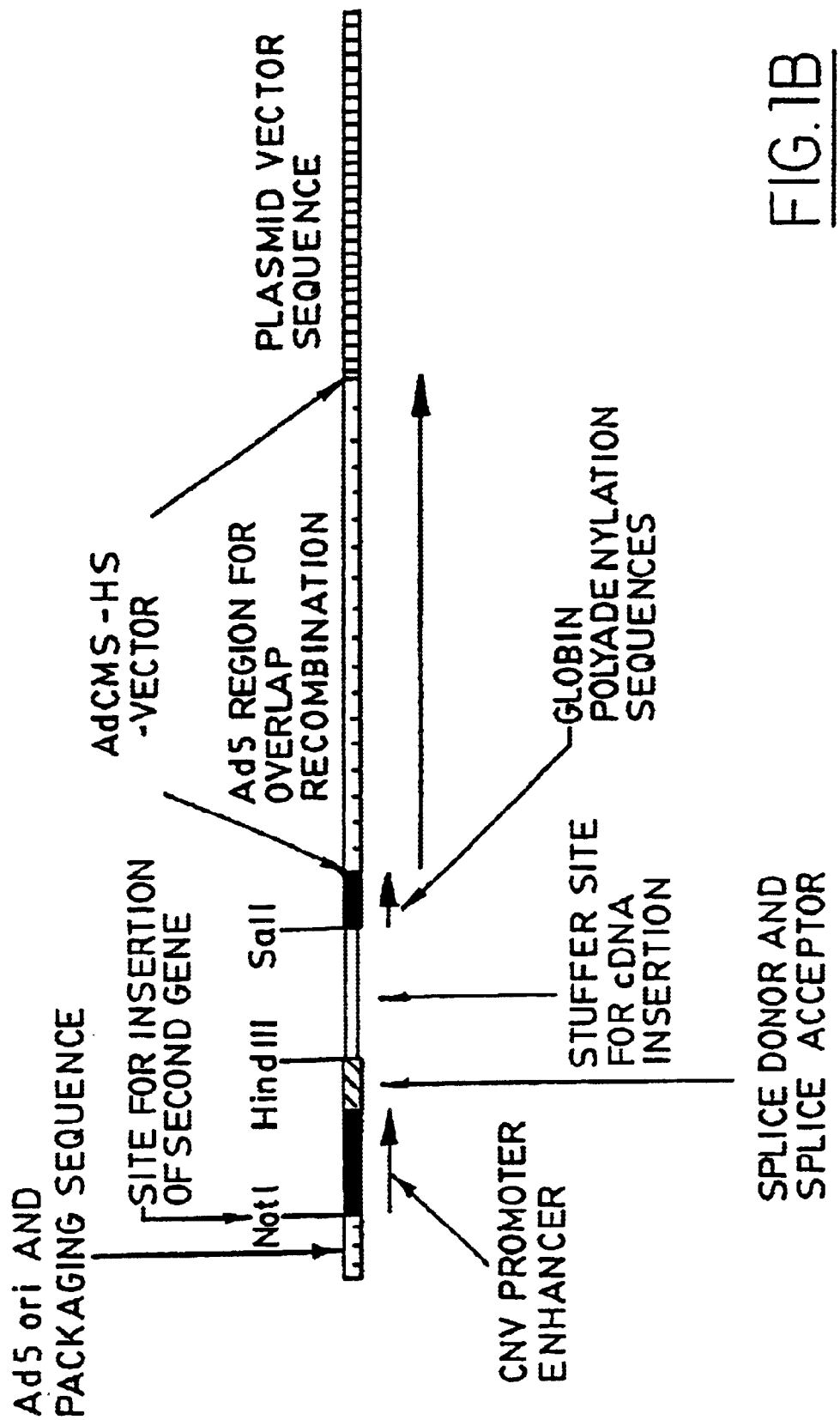

Construction of pAdCMV-HS-Vector pAdCMV-HS-Vector (FIGS. 1(a) & 1(b)) has the globin poly(A) site inserted downstream of the L3 poly(A) site of pAdCMV-gamma interferon. Digestion with HindIII and SalI released the Interferon cDNA and the L3 poly(A) site leaving the Adenovirus 0–353 sequence, the CMV promoter, the splice acceptor and donor, and the globin poly(A) site and adenovirus sequence from 2800–5776. With reference to FIG. 22, there is shown the nucleotide sequence of pAdCMV-HS-Vector.

EXAMPLE IX

Expression of Thyrothopin-releasing Hormone (TRH) Receptors

1. Materials:

Dulbecco's modified Eagle's medium, modified Eagle's medium, Ham's F10 medium and horse and fetal bovine serums were purchased from GIBCO. Nu-serum was obtained from Collaborative Research. TRH, methylTRH and PMA were obtained from SIGMA. myo-[$^3$H] inositol was obtained from Amersham. [$^3$H] methylTRH was obtained from Du Pont-New England Nuclear. The expression vector pCDM8 was obtained from INVITROGEN.

2. Construction of AdCMVmTRHR:

The parent plasmid, pAdCMVmTRHR, was constructed by inserting a 1.2 kb EcoRI-NotI fragment containing the protein-coding region of the mouse TRH-R cDNA, nucleotides 233–1462 of plasmid pBSmTRHR (Straub et al., 1990, Proc. Natl. Acad. Sci. U.S.A., vol. 87, pp. 9514–9518, which disclosure is hereby incorporated by reference), into plasmid pGEM2-L3-114 at the EcoRl-BamHl site. After digesting with EcoRI and using the Klenow fragment of DNA polymerase I to make blunt DNA ends, HindIII linkers were ligated and a 1.4 kb HindIII fragment containing mouse TRH-R cDNA and the adenovirus E2 poly(A) signal sequence was isolated and inserted into the HindIII site of the pAdCMV-HS-Vector (i.e., expression plasmid of the present invention) which contains the left end replication and packaging elements of adenovirus, the cytomegalovirus-1 promoter and splicing elements from plasmid pML-SIS Cat (Huang et al., 1990, Nucleic Acids Res., vol. 18, pp. 937–947, which disclosure is hereby incorporated by reference). Following verification of the plasmid by restriction site mapping and transient transfection of pAdCMVmTRHR into COS-1 cells to demonstrate TRH-R expression, the virus AdCMVmTRHR was constructed by overlap recombination as described by Tantravahi et al., 1993, Mol. Cell. Biol., vol. 13, pp. 578–587, which disclosure is hereby incorporated by reference. All transfections were carried out in human embryonic kidney cells transformed with the E1 region of adenovirus type 5 according to the procedure of Graham et al., 1977, J. Gen. Virol., vol. 36, pp. 59–72, which disclosure is hereby incorporated by reference. Following plaque purification, virus was grown in 293 cells in suspension cultures as described by Antravahi et al., 1993, Mol. Cell. Biol., vol. 13, pp. 578–587, which disclosure is hereby incorporated by reference. The entire sequence coding for the adenovirus E1a gene was removed as well as the 5' 1.8 kb of the E1b gene. Co-transfection of pAdCMVmTRHR with the large fragment of adenovirus (3.8–100 map units) into 293 cells resulted in production of recombinant virus AdCMVmTRHR.

3. Infection with AdCMVmTRHR:

Cells were seeded in wells (3.8 cm$^2$) pretreated with poly-L-lysine and were incubated in medium supplemented with serum in a humidified atmosphere of 5% $CO_2$. After a minimum of 4 hours, the medium was aspirated and replaced with 0.3 ml of medium without serum, AdCMVmTRHR (300 particles/cell) was added and the cells were incubated at 37° C. After 1 hour, 0.7 to 1.0 ml medium containing serum was added and the incubation continued for 3 to 72 hours. Infection with AdCMVmTRHR was performed in an identical manner for all cell types except that the incubation mediums were different. The mediums were: Dulbecco's modified Eagle's medium supplemented with 5% Nu-Serum for human cervical cancer HeLa cells, monkey kidney Cos-1 and CV-1 cells, and rat glioma C6 cells; Ham's F-10 medium with 15% horse serum and 2.5% fetal bovine serum for rat pituitary tumor GHY cells; Delbecco's modified Eagle's medium with 10% Nu-Serum for mouse pituitary tumor AtT-20 cells; and modified Eagle's medium with 10% fetal bovine serum for human epidermoid KB cells. None of these cell lines express TRH-Rs. Cells were studied 16 to 24 hours after infection with 300 AdCMVmTRHR particles per cell which yielded maximal TRH-R expression.

4. Transfection with pAdCMVmTRHR or pCDM8mTRHR:

pCDM8mTRHR is an expression vector in which TRH-R DNA transcription is controlled by a cytomegalovirus-1 promoter and which contains the SV-40 sequence for plasmid replication in COS-1 cells (Straub et al., 1990, *Proc. Natl. Acad. Sci. U.S.A.*, vol. 87, pp. 9514–9518, which disclosure is hereby incorporated by reference). One of two DEAE dextran methods (Cullen, B. R., 1987, *Methods. Enzymol.*, vol. 152, pp. 684–704, which disclosure is hereby incorporated by reference) that yielded the higher level of expression was used depending on the cell type. For HeLa, CV1 and COS-1 cells, a protocol that included incubation with pAdCMVmTRHR or pCDM8mTRHR and DEAE dextran at 37° C., incubation with 0.08 mM chloroquine for 2.5 hours and addition of dimethylsulfoxide (10%) for 2.5 minutes was used (Straub et al., 1990, *Proc. Natl. Acad. Sci. U.S.A.*, vol. 87, pp. 9514–9518, which disclosure is hereby incorporated by reference). For GHY, AtT-20 and C6 cells, incubation with plasmid and DEAE dextran was for 0.5 hours at 4° C. and no chloroquine or dimethylsulfoxide was added (Fujimoto et al., *Endocrinology*, vol. 130, pp. 1879–1884, which disclosure is hereby incorporated by reference). Cells were studied 48 to 72 hours after transfection, which are times of maximum TRH-R expression.

5. Measurement of TRH-R Number:

Binding of 0.1 to 7.5 nM [$^3$H]methylTRH, an analog of higher affinity and potency than TRH (Vale et al., 1971, *Endocrinology*, vol. 89, pp. 1485–1488, which disclosure is hereby incorporated reference), to intact cells was measured as described by Gershengorn, M. C., 1978, *J.Clin. Invest.*, vol. 62, pp. 937–943, which disclosure is hereby incorporated by reference. Binding isotherms were fitted and dissociation constants ($K_d$s) and receptor numbers (one-to-one stoichiometry of methylTRH and receptor) were obtained with the INPLOT program (Graphpad). Receptor number was calculated using the following equation: fractional occupancy=$1/[1+(K_d/L)]$. Receptor number is given assuming that all cells in the population are expressing equal numbers of TRH-Rs. This appears to be the case with infections using 300 AdCMVmTRHR particles per cell (not shown).

6. Measurement of TRH Response:

Infected or transfected cells were labelled for 24 hours with [$^3$H]myo-inositol, stimulated with TRH or methylTRH in a balanced salt solution containing 10 mM LiCl and [$^3$H]IPs were measured as described by Imai et al., 1987, *Methods. Enzymol.*, vol. 141, pp. 100–101, which disclosure is hereby incorporated by reference.

7. Measurement of Desensitization and Inhibition by PMA:

Cells were incubated in medium with serum containing myo-[$^3$H]inositol (1 µCi/ml) for 24 hours prior to infection and studied 16 to 24 hours after infection. The desensitization protocol was as described by Perlmand et al., 1991, *Endocrinology*, vol. 129, pp. 2679–2686, which disclosure is hereby incorporated by reference, except all incubations were at 37° C. Stimulation by TRH was in cells incubating in medium with serum containing myo-[$^3$H] inositol to prevent depletion of $^3$H-labelled phosphoinositide substrate. The rate of IP formation was determined by linear regression analysis of the amount of [$^3$H]IPs, expressed as % of $^3$H-labelled phosphoinositides, per minute during a 30 minute incubation. The desensitized rate is measured after 60 minutes of stimulation by 1 µM TRH by adding LiCl to a final concentration of 10 mM. The initial rate of TRH-stimulated IP formation is measured by adding TRH and LiCl simultaneously (at 60 minutes in parallel with the desensitized cells). In experiments with PMA, PMA was dissolved in dimethylsulfoxide and was added 60 minutes prior to TRH and LiCl to a final concentration of 0.1 µM.

8. Internalization of TRH-Rs:

Internalization was measured as specifically bound [$^3$H] methylTRH that was resistant to acid wash (Hinkle et al., 1982, *J.Biol. Chem.*, vol. 257, pp. 5462–5470; and Nussenzveig et al., 1993, *J.Biol. Chem.*, vol. 268, pp. 2389–2392, which disclosures are hereby incorporated by reference). Specific acid resistant binding was calculated by subtracting the nonspecifically bound from the [$^3$H]methylTRH remaining after acid/salt elution.

Results

Figure 13:
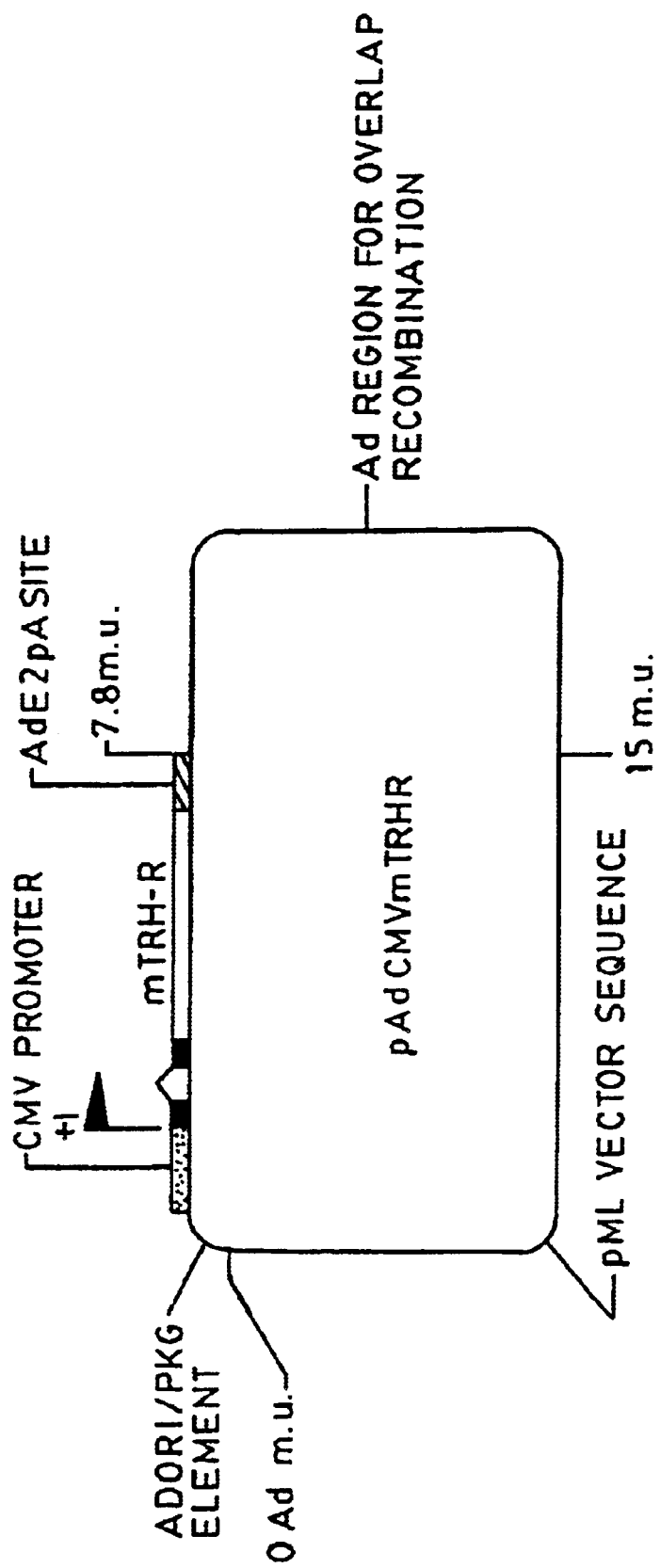
FIG. 13 is a graphic map of plasmid vector pAdCMVmTRHR used for the construction of recombinant adenovirus AdCMVmTRHR.

A highly efficient, replication defective recombinant adenovirus, AdCMVmTRHR, was constructed which contains the coding sequence of the mouse TRH-R under the control of the cytomegalovirus-1 promoter and RNA processing elements inserted at the E1 region of a parent adenovirus-5 genome, dl309 or a derived derivative (Jones et al., 1979, *Cell*, vol. 17, pp. 683–689, which disclosure is hereby incorporated by reference). The strategy employed for the construction of AdCMVmTRHR (FIG. 13) was similar to that used in the construction of the plasmid vector constructs of the invention (FIGS. 1(a) & 1(b)). With reference to FIG. 13, there is shown plasmid vector pAdCMVmTRHR, which was used to produce recombinant adenovirus AdCMVmTRHR. Turning to FIG. 13, the left end of the adenovirus starts at position 1. The adenovirus sequence from nucleotide 1–353 contains the origin of replication and the viral packaging sequence. The adenovirus sequence from 354–2800 is deleted and replaced with the CMV-1 promoter, splice elements, the protein coding region of the mouse TRH-R cDNA sequence and the E2 poly(A) site. The left end adenovirus sequence from nucleotides 2800–5776 serve as the region for homologous recombination.

Figure 14:
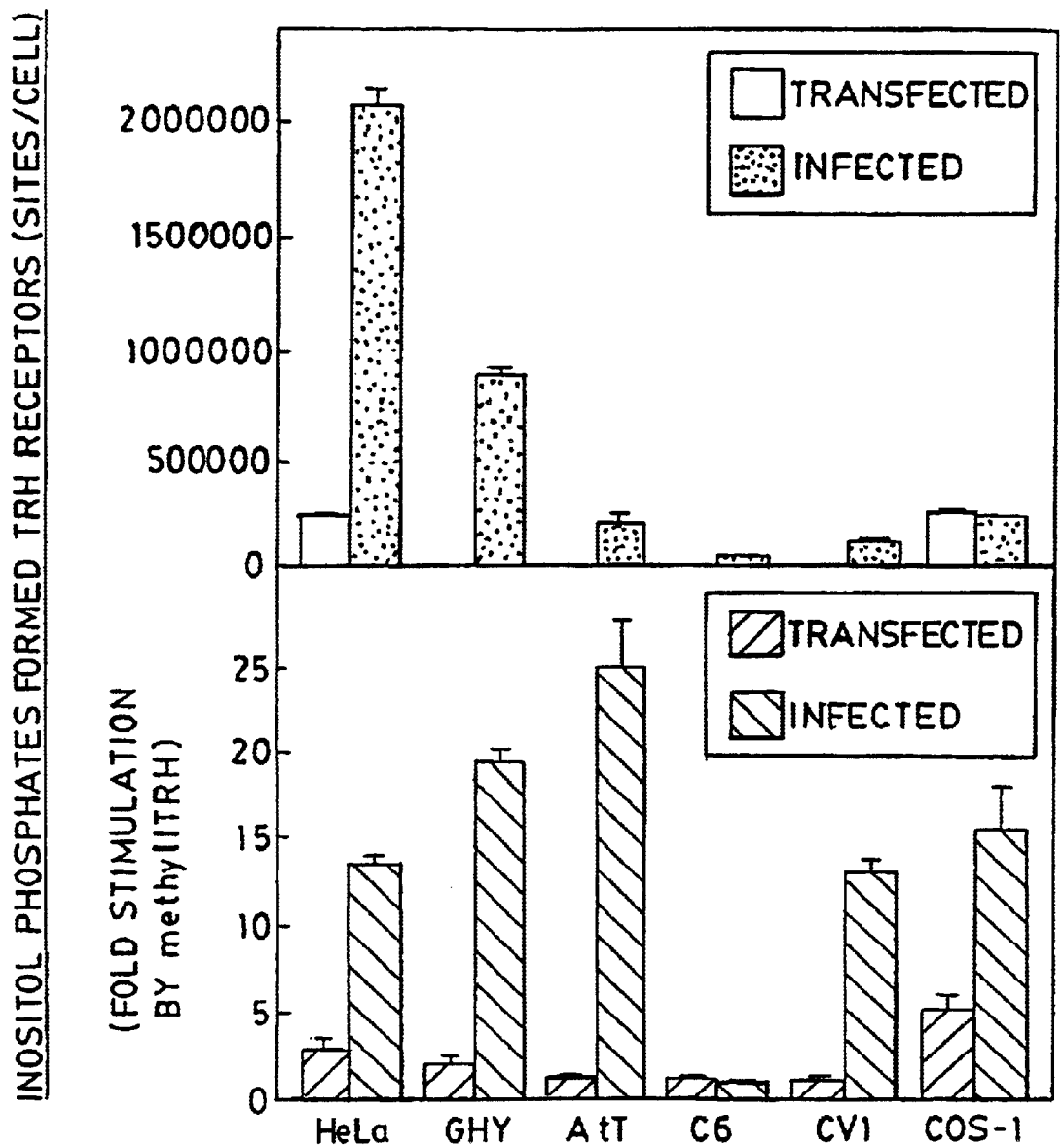
FIG. 14 is a graph showing a comparison of infection with AdCMVmTRHR and transfection with pAdCMVmTRHR on expression of TRH-Rs and methylTRH responsiveness in six mammalian cell lines.

The novelty of AdCMVmTRHR as a vector for expression of TRH-Rs and its advantage over transfection are illustrated in FIG. 14. With reference to FIG. 14, the levels of TRH-R expression (upper panel) and methylTRH stimulation of [$^3$H]IP formation (lower panel) were measured as previously described. The data in the (upper panel) are presented as number of receptors per cell assuming that all cells express equal numbers of TRH-Rs. The bars in both panels represent the mean ±SD of triplicate determinations in a representative experiment that was performed 3 times. In these experiments the plasmid vector used for virus construction, and expression of TRH-Rs after infection with AdCMVmTRHR and after transfection with pAdCMVmTRHR, were compared in HeLa cells, rat pituitary tumor GHY cells, mouse pituitary tumor AtT-20 cells, rat glioma C6 cells and monkey kidney CV1 and COS-1 cells. These cell lines were chosen because they represent a wide variety of cell types which do not express TRH-Rs. That is, HeLa cells were studied because they are readily infected with adenovirus. GHY cells were studied because they are a subclone of the cells in which endogenous TRH-Rs have been most well-studied. COS-1 cells were studied because they are a commonly used, transformed cell line that permits high levels of expression during transient assays.

TRH-Rs expressed on the surface of these cells after infection with AdCMVmTRHR bound methylTRH with the same affinity as native TRH-Rs on mouse pituitary cells (Gershengorn et al., 1978, *J. Clin. Invest.*, vol. 62, pp. 937–943, which disclosure is hereby incorporated by reference) or TRH-Rs stably (Fujimoto et al., 1992, *Endocrinology*, vol. 130, pp. 1879–1884, which disclosure is hereby incorporated by reference) or transiently (Straub et al., 1990, *Proc. Natl. Acad. Sci. USA*, vol. 87, pp. 9514–9518; and Perlman et al., 1992, *J. Biol. Chem.*, vol. 267, pp. 24413–24417, which disclosures are hereby incorporated by reference) expressed on several different cell types including COS-1 and HeLa cells after transfection. The dissociation constant for methylTRH binding was 1.09±0.26 nM (data not shown). An important finding was that there was a higher level of TRH-R expression in every cell type except COS-1 cells when gene transfer was mediated by AdCMVmTRHR infection compared to transfection with pAdCMVmTRHR (FIG. 14, upper panel) or with plasmid, pCDM8mTRHR (Straub et al., 1990, *Proc. Natl. Acad. Sci. USA*, vol. 87, pp. 9514–9518, which disclosure is hereby incorporated by reference), that can replicate efficiently in COS-1 cells (data not shown). Under the conditions studied, there were marked differences among the various cell types in the levels of expression of TRH-Rs after infection by AdCMVmTRHR. Although the optimal conditions for AdCMVmTRHR-mediated TRH-R expression in each cell type has not been determined, these differences may be related to intrinsic characteristics of the different cell types rather than differences in conditions needed for optimal infection. For example, there may be cell-specific differences in efficiencies of adenovirus infection, perhaps related to the number of adenovirus receptors, of expression of exogenous genes in general or of TRH-R specifically, or in turnover of TRH-Rs. Infection by AdCMVmTRHR led to higher levels of TRH-R expression in a wider range of cell types than transient transfection.

A proximal step after TRH-R activation is stimulation of the formation of IP second messengers (Gershengorn et al., 1986, *Annu. Rev. Physiol.*, vol. 48, pp. 515–526; and Drummong, A. H., 1986, *J. Exp. Biol.*, vol. 124, pp. 337–358, which disclosure is hereby incorporated by reference). Therefore, ethylTRH stimulation of IP formation was measured as a response to TRH-R activation. Uninfected HeLa, CHY, AtT, C6, CV1 and COS-1 cells did not respond to methylTRH. In parallel with the number of TRH-Rs, there was a greater stimulation of IP formation by methylTRH in all cell types after infection by AdCMVmTRHR than after transfection. However, there was no correlation between the magnitude of the methylTRH response and the number of TRH-Rs when comparing different cell types. For example, methylTRH stimulation of IP formation was greater in AtT-20 cells which expressed TRH-Rs at a lower number than in HeLa cells with a greater number of TRH-Rs. One explanation for this observation may be that there are differences in post-receptor components of the signal transduction cascades within these different cell types. Another finding was that the magnitude of response to methylTRH in COS-1 cells was greater after infection than after transfection even though the total number of receptors was similar. This may be because all COS-1 cells expressed a maximally effective number of TRH-Rs after AdCMVmTRHR infection, whereas only a fraction of the transfected cells were expressing maximally effective numbers of TRH-Rs because infection is more efficient than transfection.

Figure 15:
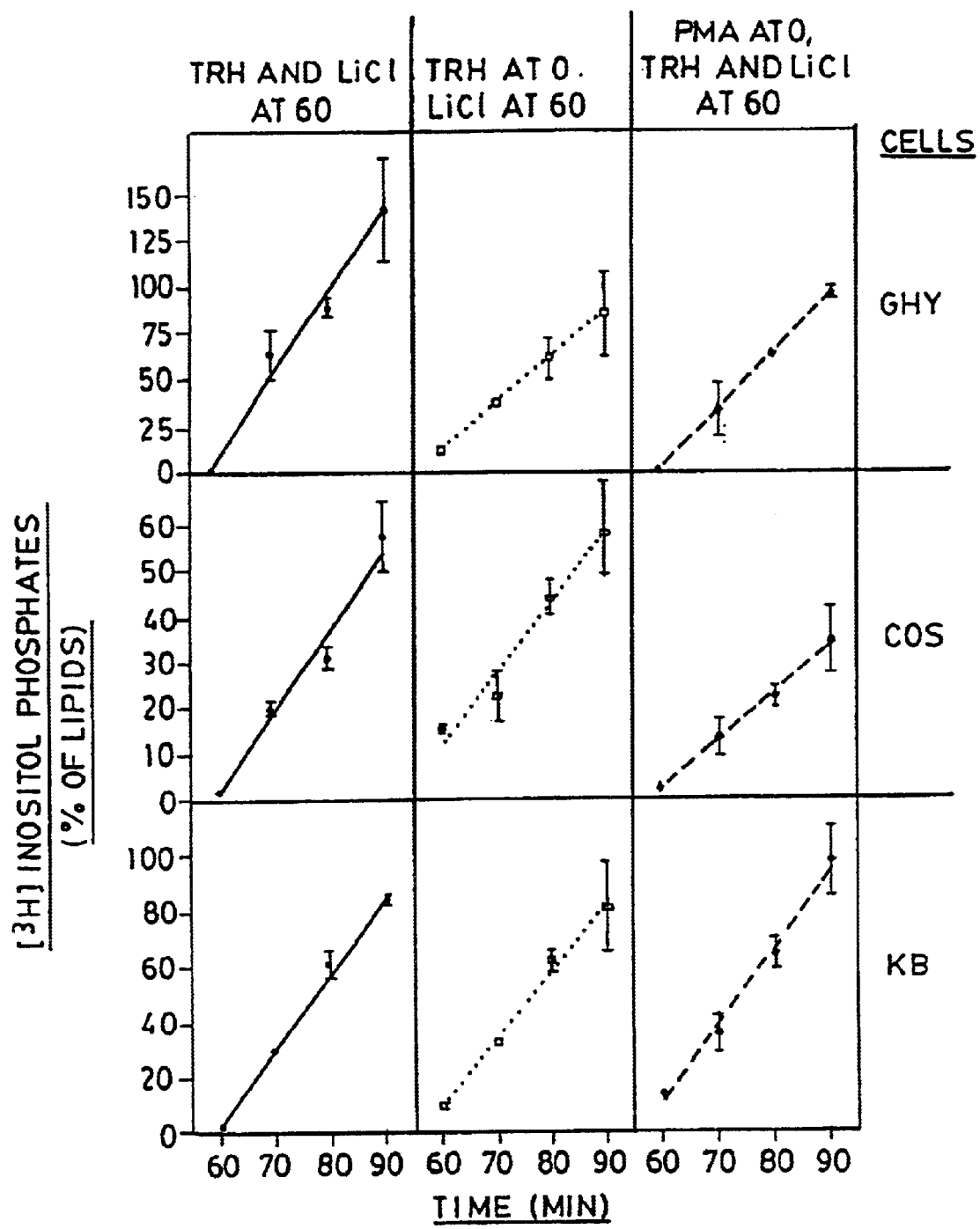
FIG. 15 is a graph showing TRH-induced desensitization and PMA-induced inhibition of the TRH response in AdCMVmTRHR-infected GHY, COS-1 and KB cells.

In rat $GH_3$ pituitary cells naturally expressing TRH-Rs, the TRH response is rapidly desensitized (Perlman et al., 1991, *Endocrinology*, vol. 129, pp. 2679–2686, which disclosure is hereby incorporated by reference). This effect occurs prior to any decrease in the number of TRH-Rs ("down-regulation") (Gershengorn, M. C., 1978, *J. Clin. Invest.*, vol. 62, pp. 937–943; and Hinkle et al., 1975, *Biochemistry*, vol. 14, pp. 3845–3851, which disclosures are hereby incorporated by reference. This response to TRH is also blunted in $GH_3$ cells preincubated with phorbol esters, such as PMA, which activate protein kinase C (Drummong, A. H., 1986, *J. Exp. Biol.*, vol. 124, pp. 337–358, which disclosure is hereby incorporated by reference). Evidence, however, is presented that these two effects are distinct and suggested that TRH-induced desensitization is not mediated primarily by protein kinase C (Perlman et al., 1991, *Endocrinology*, vol. 129, pp. 2679–2686, which disclosure is hereby incorporate by reference). Although the molecular mechanisms of TRH-induced desensitization and of PMA-induced inhibition of the TRH response have not been elucidated, it is likely that they are mediated by receptor phosphorylation (Lefkowitz et al., 1992, *Cold Spring Harbor Symp. Quant. Biol.*, vol. 57, pp. 127–134, which disclosure is hereby incorporate by reference). Because different cell types contain different complements of protein kinases, it was possible that TRH-induced desensitization and PMA-induced inhibition of the TRH response are cell type specific. AdCMVmTRHR infection was used to express TRH-Rs in several different cell types. FIG. 15 illustrates that TRH-induced desensitization and PMA inhibition of the TRH response do not occur in all cell types. With reference to FIG. 15, GHY, COS-1 (COS) and KB cells were infected with 300 AdCMVmTRHR particles per cell and TRH-induced desensitization and PMA-induced inhibition of the TRH response was measured as previously described. The data represent the mean SD of triplicate determinations in a representative experiment that was performed two or three times. TRH-induced desensitization and PMA-induced inhibition of the TRH response were observed in both pituitary cell types studied. In AdCMVmTRHR-infected GHY cells, the response to TRH is decreased by 49±5.2% after 60 minutes of TRH stimulation and PMA inhibits the response by 25±4.6%. Similar observations were made in AdCMVmTRHR-infected AtT-20 cells in which TRH-induced desensitization led to IP formation at a rate decreased by 41±4.7% compared to control and PMA decreased the TRH response by 37±4.0%. These effects are indistinguishable from those measured with endogenous TRH-Rs in $GH_3$ cells (Perlman et al., 1991, *Endocrinology*, vol. 129, pp. 2679–2686, which disclosure is hereby incorporated by reference). In contrast, in AdCMVvTRHR-infected COS-1 cells, the response to TRH did not desensitize whereas PMA inhibited the TRH response by 37±8.0%. In AdCMVmTRHR-infected KB cells, which expressed 1.16±0.02×10$^6$ TRH-Rs per cell, there was no TRH-induced desensitization (0±10%) and PMA did not inhibit the TRH response (0±10%). Thus, in a limited survey of cell lines, TRH-induced desensitization and PMA-induced inhibition of the TRH response were found only in two rodent pituitary-derived cell types, PMA-induced inhibition of TRH responsiveness but not TRH-induced desensitization was observed in monkey kidney-derived cells, and neither TRH-induced desensitization nor PMA-induced inhibition of TRH responsiveness were found in human epidermoid-derived cells. These findings support our previous suggestion that TRH-induced desensitization is not mediated by protein kinase C as TRH-induced desensitization does not occur but PMA inhibits the TRH response in COS-1 cells.

Figure 16:
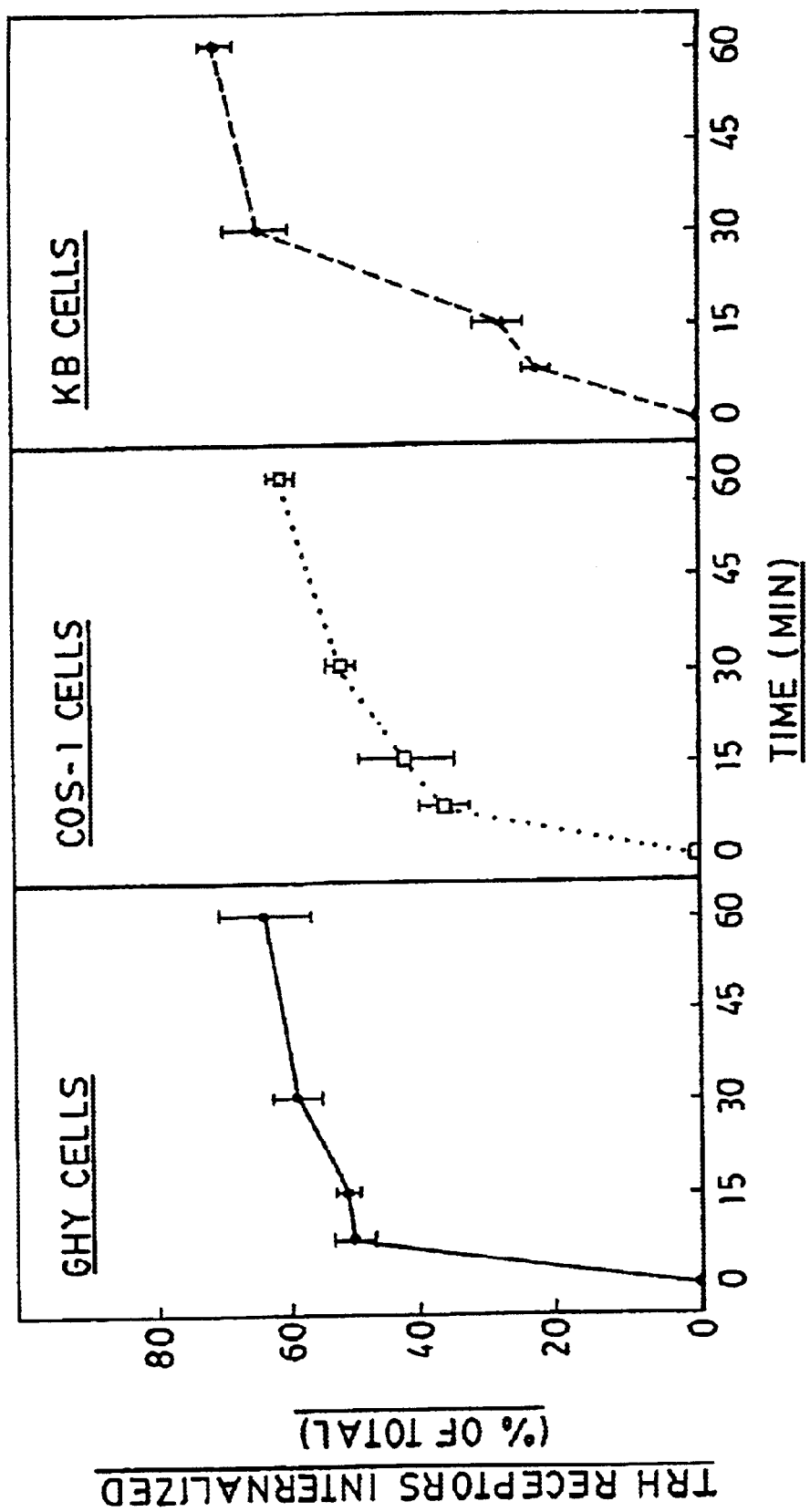
FIG. 16 is a graph showing methylTRH-stimulated TRH-R internalization in AdCMVmTRHR-infected GHY, COS-1 and KB cells.

Rapid internalization is another process that many GPCRs, including TRH-Rs (Nussenzveig et al., 1993, *J. Biol. Chem.*, vol. 268, pp. 2389–2392; and Hinkle, P. M., 1989, *Ann. N. Y. Acad. Sci.*, vol. 553, pp. 176–187, which disclosures are hereby incorporated by reference), undergo after binding (Dohlman et al., 1991, *Annu. Rev. Biochem.*, vol. 60, pp. 653–688, which disclosure is hereby incorporated by reference). To determine whether TRH-R internalization is cell type specific, we measured internalization of bound methylTRH in three AdCMVvTRHR-infected cell lines which displayed differences in TRH-induced desensitization or PMA-induced inhibition of the TRH response, or both. Internalization in cell lines that do and do not exhibit rapid desensitization induced by TRH was measured because it has been controversial whether these two processes are related. FIG. 16 illustrates that internalization of methylTRH-bound TRH-Rs was faster in AdCMVmTRHR-infected GHY cells than in COS-1 cells and KB cells but that the fraction of receptors internalized after 60 minutes was similar in all three cell types. After 60 minutes, 64±7.0%, $62\pm2.1\%$, and 71±2.6% of TRH-Rs were internalized in AdCMVmTRHR-infected GHY, COA-1 and KB cells, respectively. With reference to FIG. 16, internalization of TRH-Rs was measured as previously described. The data represent mean ±SD of triplicate determinations in a representative experiment performed twice. In these three cell lines, agonist-induced internalization of TRH-Rs exhibited small kinetic differences but the extent of internalization after 60 minutes, the time at which measured desensitization were similar.

A number of aspects of GPCR biology may vary when receptors are expressed in different cell types. For example, the same GPCR may activate different signal transduction pathways when expressed in different cell types (Milligan et al., 1993, *Trends Pharmacal. Sci.*, vol. 553, pp. 176–187, which disclosure is hereby incorporated by reference). Agonist-induced desensitization, which is a process that commonly accompanies activation of GPCRs, appears to be mediated by a conserved set of intracellular regulatory proteins including protein kinases and arrestin-like proteins (Lefkowitz et al. 1993, *Adv. Second Messenger Phosphoprotein Res.*, vol. 28, pp. 1–9; and Lefkowitz, R. J., 1993, *Cell*, vol. 74, pp. 409–412, which disclosures are hereby incorporated by reference). The data demonstrated that desensitization of TRH-Rs may occur in some cell types (GHY and AtT-20 cells) but not in others (COS-1 and KB cells). Although we have been able to show TRH-induced desensitization only in cell lines derived from the pituitary gland, it can not be concluded that TRH-R desensitization occurs only in pituitary-derived cells because only a small number of cell lines were studied. In contrast to desensitization, agonist-induced TRH-R internalization occurred in GHY, COS-1 and KB cells. This finding supports previous conclusions (Kobilka, B., 1992, *Annu. Rev. Neurosci.*, vol. 15, pp. 87–114, which disclosure is hereby incorporated by reference) that the mechanisms that mediate desensitization and internalization are distinct.

In summary, a replication defective adenovirus, AdCMVmTRHR, was constructed in accordance with the present invention and used for the high efficiency expression of TRH-Rs. Using this virus, we have been able to express TRH-Rs in a variety of mammalian cell types and study several aspects of TRH-R biology in different cell environments. We found that desensitization of the TRH response is cell type specific which occurred only in pituitary-derived cells in a limited survey of cell types whereas agonist-induced TRH-R internalization is found more generally. It was concluded that adenovirus mediated gene transfer is an excellent method for expression of TRH-Rs and suggest that this approach could be extended for expression of other cell regulatory proteins in many cell types. The versatility of adenovirus-mediated gene transfer and expression of TRH-Rs not only facilitates in vitro studies of TRH-R biology, but should also provide a valuable in vivo expression vector capable of extending TRH-R studies to animal model systems.

EXAMPLE X;

Quantitative Determination of Adenovirus-mediated Gene Delivery to Rat Cardiac Myocytes in vitro and in vivo 1, Isolation and Culture of Rat Cardiac Myocytes:

Primary fetal cardiac myocytes were prepared from fetal day 20 Sprague-Dawley rats (Taconic Farms) by modification of the protocol of de Carvalho et al., 1992, *Circ. Res.*, vol. 70, pp. 733–742, which disclosure is hereby incorporated by reference. Cardiac cells were preplated for 1 hour in order to remove fibroblasts. 1.8×10$^6$ cells were then plated per 25 mm tissue culture dishes (Corning) in heart medium (Hank's salt solution supplemented with MEM Vitamin Stock, MEM amino acids, MEM non-essential amino acids, L-Glutamine (2 mM), 1% Glycine, 2% Hypoxanthine, 1% Penn-Strep, NaHCO$_3$) with 10% fetal bovine serum (Hyclone). Primary adult cardiac myocytes were prepared from the hearts of 200 g female Sprague-Dawley rats (Taconic Farms) according to the protocol of White et al. 1993, *Biophys. J.*, vol. 65, pp. 196–204, which disclosure is hereby incorporated by reference. 2.4×10$^5$ cells were plated in heart medium per 60 mm dish coated with 20 ug/ml of laminin (Boehringer Mannheim). Cells were maintained in culture at 37° C., 5% CO$_2$. Cell culture medium was changed every other day for the duration of the assay.

2. Virus Production:

Virus plaquing and the preparation of viral stocks were performed on 293 monolayer cells as described by Tantravahi et al., 1993, *Mol. Cell. Biol.*, vol. 13, pp. 578–587, which disclosure is hereby incorporated by reference.

3. Infection of Cardiac Myocytes:

Forty eight hours after plating, fetal myocytes were infected with AdCMVCATgD at 0.01, 0.1, 1, 10 pfu/cell. The adult cells were infected with the same doses immediately after plating. AdCMVCATgD (10$^{10}$ pfu/ml) was diluted in heart media without added serum. One ml of media+virus was added to each 60 mm dish. The dishes were incubated for 90 minutes at 37° C., swirling gently every 15 minutes after which 1 ml of heart media (supplemented with a final concentration of 10% fetal bovine serum) was added to each dish.

4. Immunohistochemistry:

Cells were fixed on coverslips in 3.7% formaldehyde in phosphate buffered saline (8M NaCl, 0.2M KCl, 1.44M NaHPO$_4$, KH$_2$PO$_4$, pH 7.4) (PBS) for 10 minutes at room temperature. Coverslips were then washed in PBS. Cells were blocked in 10% normal goat Serum (NGS) (Jackson Immunolabs) for 2 hours at 37° C. The coverslips were then incubated for 2 hours at 37° C. with a commercially available unconjugated rabbit polyclonal antibody which recognizes CAT (5 Prime-3 Prime) at a 1:1000 dilution in PBS containing 0.1% Triton, 1% NGS. Following three 5 minutes washes in PBS, the coverslips were incubated for 1 hour at 37° C. with a peroxidase conjugated goat anti-rabbit antibody (BioRad) at a 1:200 dilution in PBS containing 0.1% Triton, 1% NGS. After three 5 minutes washes in PBS, the peroxidase reaction was developed using Vectastain DAB (Vector) according to manufacturer's instructions. For tissue sections, five days post-injection, hearts were removed and the distal ¼ of the heart was placed in 3.7% formaldehyde at 4° C. overnight. The samples were embedded in a paraffin (Paraplast) according to the protocol of Ausbel et al., 1989, *Current Protocols in Molecular Biology*, Wiley, New York, which disclosure is hereby incorporated by reference. 4–10μ tissue sections were cut and placed on slides coated with 0.05% w/v poly-L-Lysine (Sigma) and dried overnight at room temperature. The sections were then ethanol dehydrated, and deparaffinized in xylenes. After rehydration, sections were placed in 0.1% Triton in phosphate buffered saline (PBS) for 5 minutes. The endogenous peroxidase activity was blocked by placing the sections in 0.3% hydrogen peroxide in methanol for 30 minutes. The antibody staining procedure was carried out as previously described. Following the peroxidase developing reaction the slides were washed in distilled water (dH$_2$O) and the heart sections were counterstained with hematoxylin for 12 seconds. The slides were then washed in dH$_2$O and mounted with gelvatol (Airvol, Air Products and Chemicals, Inc.).

5. CAT Assays from Myocytes:

At each time point, infected cardiac myocytes were harvested according to the protocol of Ausbel et al., 1989, *Current Protocols in Molecular Biology*, Wiley, New York, which disclosure is hereby incorporated by reference. The amount of protein in the supernatant was measured by Bradford assay using bovine serum albumin (BSA) as the standard (BioRad). CAT assays were performed on 10 μg of total protein. When the amount of CAT activity was greater than 70% and out of the linear range, supernatants were diluted in 0.1 mg/ml BSA. CAT assays were done by TLC according to the method of Kitsis et al., 1993, in *Methods in Molecular Genetics*, ed. Adolph, K. W., Academic Press, Inc., New York, Vol. 1, pp. 374–392, which disclosure is hereby incorporated by reference, incubating for 2 hours at 37° C.

6. DNA and Virus Infections in vivo:

10 μg of CMV CAT plasmid DNA in 50 μl PBS was injected into the apex of the left ventricle of 200 g female Sprague Dawley rats as described by Kitsis et. al., 1993, in *Methods in Molecular Genetics*, ed. Adolph, K. W., Academic Press, Inc., New York, vol. 1, pp. 374–392, which disclosure is hereby incorporated by reference. For the adenovirus injections, 6×10$^6$ to 6×10$^8$ pfu in 50 μl PBS were injected, 2×10$^9$ pfu were injected undiluted in a volume of 50 μl.

7. CAT Assays on Tissue:

At indicated times following injection, hearts were removed, rinsed in PBS and weighed. For the spatial distribution experiment the hearts were then sectioned into seven roughly equivalent slices. Each slice was then homogenized using a Tissumizer (Tekmar) in a volume of 0.5 mls buffer (1M Gly gly pH 7.8, 150 mM MgSO$_4$, 500 mM EGTA pH 8.0, 1M DTT) for 20 sec. For the dosage, and time course experiments the hearts were homogenized the same way but in a volume equal to 0.5 g wet tissue weight per ml of buffer. The homogenates were centrifuged for 25 minutes at 4640 xg. Supernatants were then removed, heated at 65° C., and clarified in a microfuge for 5 minutes. Supernatant volumes were measured and CAT assays were done on 5% of the lysate or on dilutions of lysate in 0.1 mg/ml BSA. Assays were done as above for 2 hours at 37° C.

Results

Figure 17:
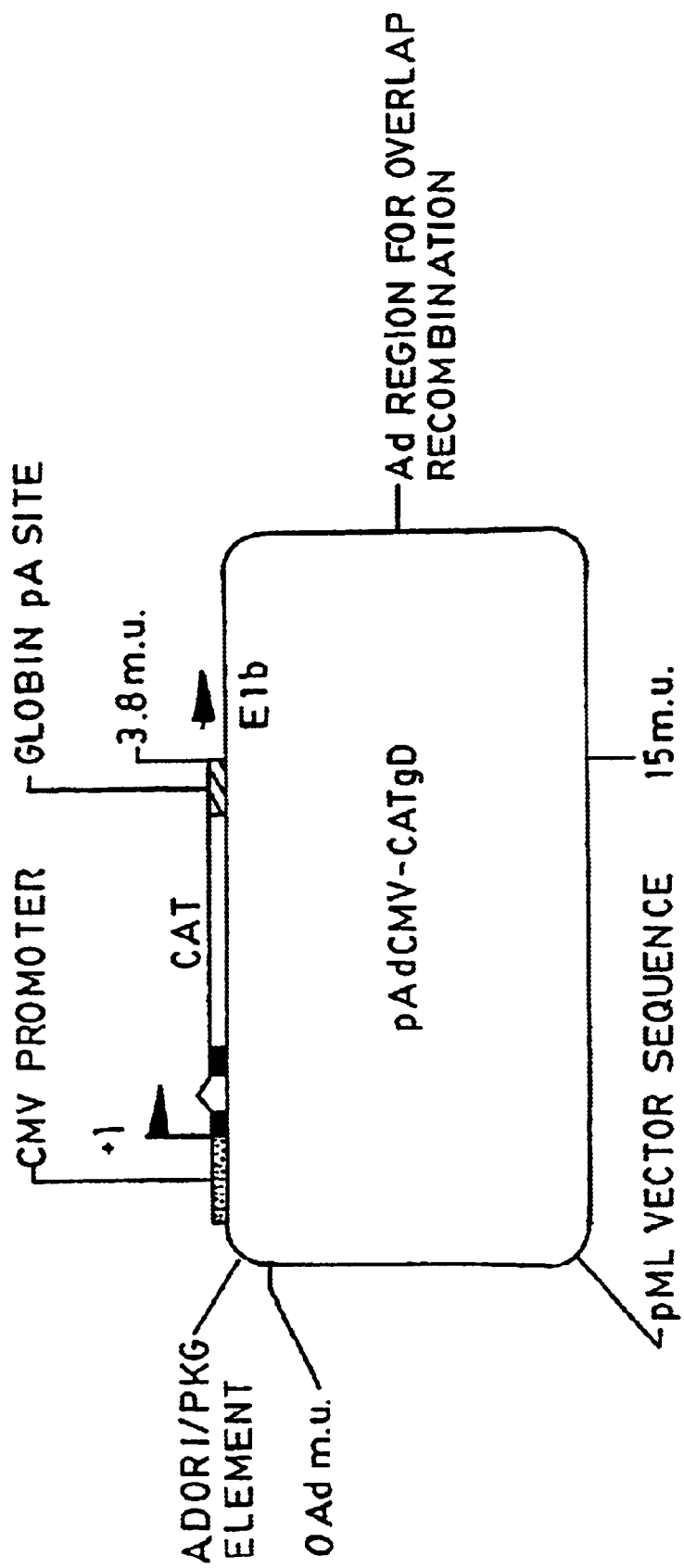
FIG. 17 is a graphic map of plasmid vector pAdCMV-CATgD used in construction of recombinant adenovirus AdCMVCATgD.

The replication defective recombinant adenovirus, AdCMVCATgD, comprising a strong eukaryotic promoter (CMV-1) and splicing elements, has proven to be a very sensitive vector for gene expression studies in human cell lines. With reference to FIG. 17, there is shown the plasmid vector, pAdCMVCATgD, which was used to produce recombinant adenovirus AdCMVCATgD. Turning to FIG. 17, the left end of adenovirus (0–1 map units (m.u.)) contains the origin of replication as well as the viral packaging sequence. The adenovirus sequence from 1.0–3.8 m.u.'s was deleted and replaced with the sequence elements for the CMV-1 promoter, the bacterial CAT sequence and the mouse β$^{maj}$ globin poly(A) site. Adenovirus sequences from 3.8–15.0 m.u.'s provides DNA sequence for homologous recombination.

Figure 18A:
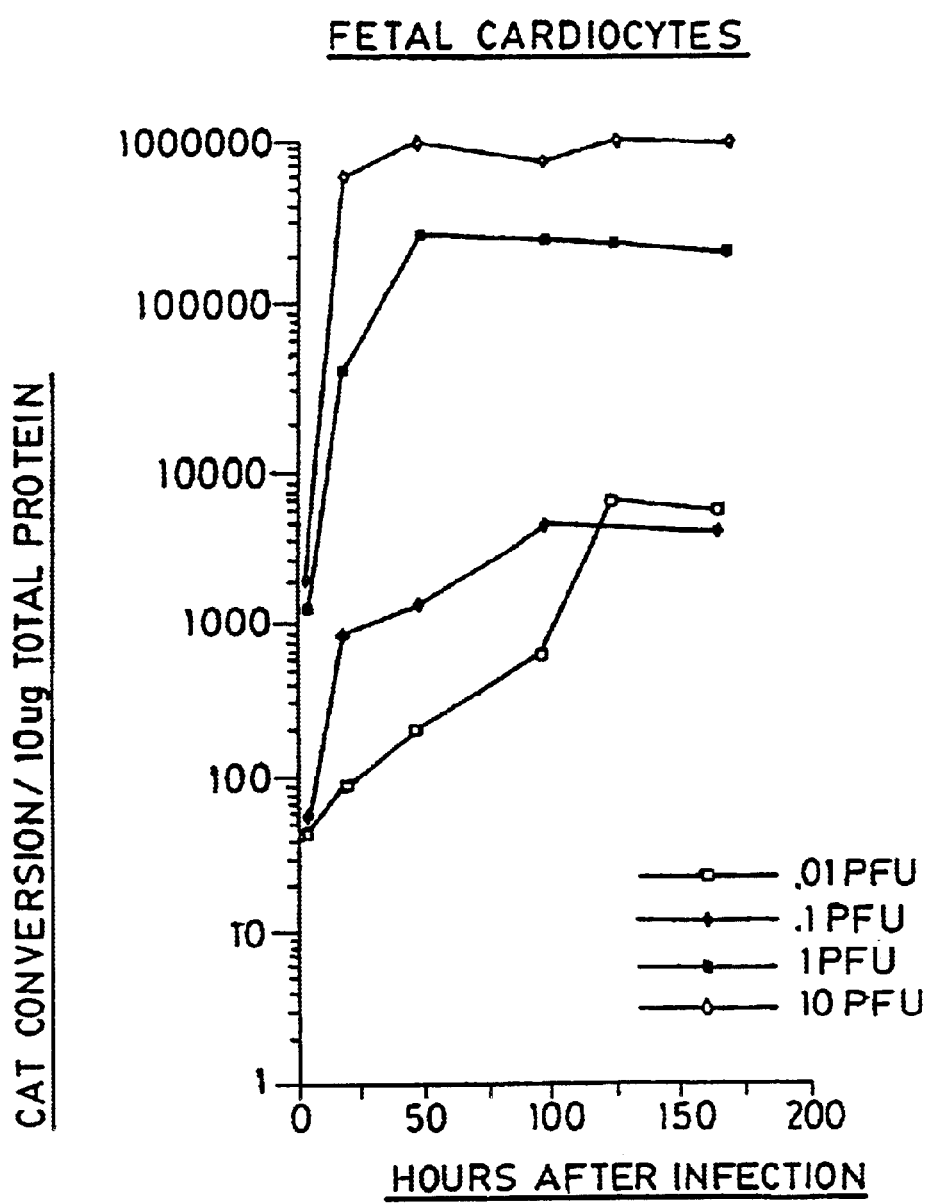
FIG. 18(a) is a graph showing dosage and time dependent expression of adenovirus in fetal cardiocytes.
Figure 18B:
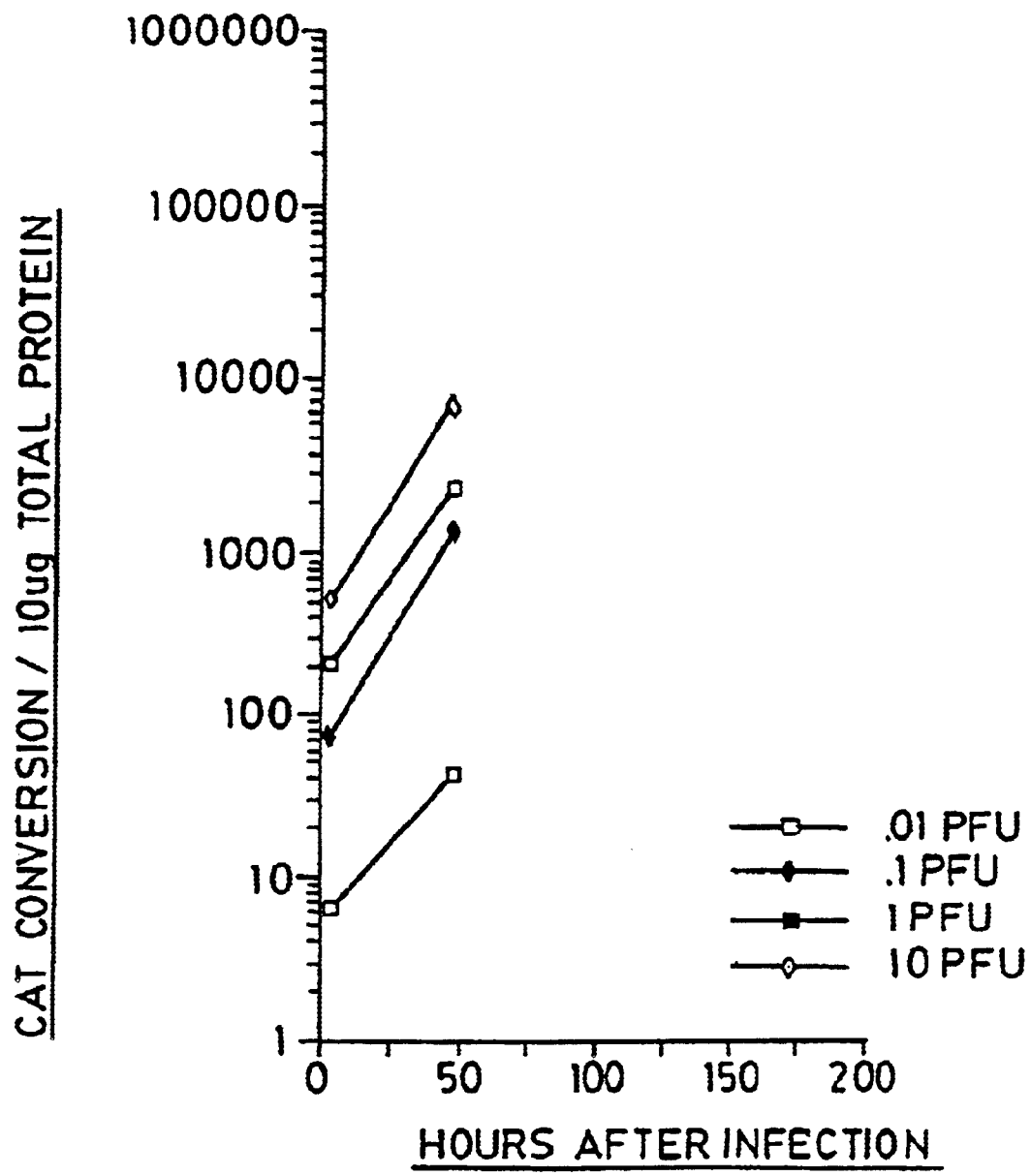
FIG. 18(b) is a graph showing dosage and time dependent CAT expression following infection by AdCMVCATgD in adult cardiocytes.

Recombinant adenovirus, AdCMVCATgD, was used to characterize adenovirus mediated gene transfer into cardiac myocytes in vitro and in vivo. FIG. 18(a) shows the dose response and time course of AdCMVCATgD infection into primary fetal rat cardiocytes. With reference to FIGS. 18(a) & 18(b), relative CAT activity refers to the percent of acetylated chloramphenicol/total chloramphenicol relative to 10 μg total protein multiplied by the dilution factor of the cell lysate in order to keep the assays within the linear range. The duration of study in adult cells was shortened due to reduced cell viability regardless of the presence of adenovirus. In these studies, infection was assessed both by quantitating CAT reporter gene expression and by determining the percentage of cells expressing the CAT reporter gene by immunostaining. Because of the extremely high levels of CAT activity obtained, dilutions of cell extracts were made to maintain assays in the linear range of the CAT assay.

CAT activity was easily detected at the earliest measured time point (4 hours), was near maximal by 48 hours, and was maintained at stable levels through the remainder of the experiment (a total of 167 hours). A dose-dependent increase was maintained over a range of hour logs of virus input throughout much of the time course. The same basic extent and level of infection and expression was found in adult cardiocytes (FIG. 16(b)) when infected under similar conditions. However, the duration of study was shortened to 48 hours due to the difficulty in maintaining healthy differentiated adult cardiac myocytes in culture, independent of virus infection. Based on these assays, the sensitivity of the AdCMVCATgD CAT assay, and the levels of activity resulting from these infections, it was redacted that CAT expression could be reliably detected in as few as 10 infected cells.

At each dose of virus, the percentage of fetal cells which were expressing CAT was determined by immunostaining coverslips of infected fetal cardiocytes 18 and 48 hours post infection. Mock-infected cells show no staining, but cells infected with increasing doses of virus show a proportional increase in the number of cells infected, with 1 pfu/cell (100 particles) resulting in virtually 100% of the cells being stained (data not shown). The virus infection included both myocytes and the small proportion of nonmyocyte fibroblasts (<5%) which remained in the culture following initial myocyte purification (data not shown). Similar results were obtained with adult cardiac myocytes. At an infection of 1 pfu or greater, 100% of the rod-shaped adult myocytes stained positive with an anti-CAT antibody. This was true at both 4 and 48 hours. Myocytes which were rounded up also stained positive for CAT, and sarcomeric myosin heavy chain, and excluded trypan blue (data not shown).

Adenovirus mediated gene transfer offers advantages to transient transfection assays when using cultured myocytes. The quantitative advantages of using AdCMVCATgD in vitro was examined to determine whether it could be extended to in vivo studies. $6 \times 10^7$ pfu of AdCMVCATgD virus were injected into adult rat hearts in a volume of 50 $\mu$l. A parallel injection of 10 $\mu$g of the plasmid pAdCMV-CATgD was carried out for quantitative comparison. Five days following injection of virus or DNA, hearts were sliced into approximately seven 1.5 mm sections perpendicular to the long axis of the heart. The amount of CAT activity was quantitated in each section. When either plasmid DNA or AdCMVCATgD is injected into rat heart, expression of the reporter gene is localized predominantly to the vicinity of the injection site (FIG. 19). With reference to FIG. 19, total CAT activity from DNA injected hearts in relative units= 2799+/−1353. Total CAT activity for adenovirus injected hearts in relative units=117,501+/−15,944. The fold difference in activity was calculated based on 75 ng of CAT DNA in $6 \times 10^7$ pfu of virus. Each line corresponds to a different animal.

Although the virus infection proved to be at least 5000 fold more efficient than the plasmid DNA injection on the basis of input DNA, the distribution of CAT activity from both DNA and virus administration is essentially identical. The highest level of expression was observed at the area of injection with a gradient of CAT activity extending towards the base of the heart.

Figure 20A:
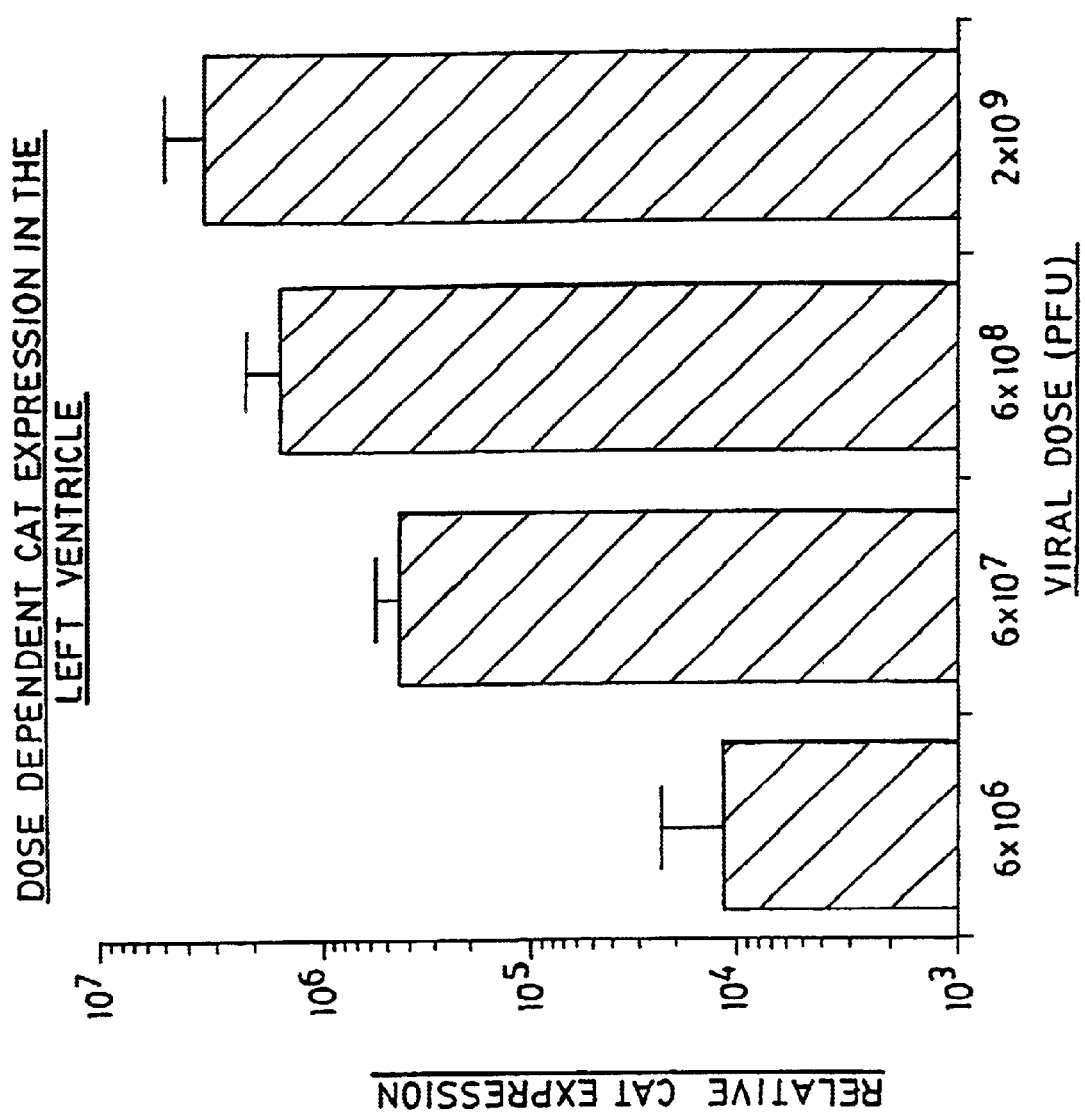
FIG. 20A is a graph showing CAT expression in the left ventricle 5 days following intracardiac injection of four doses of adenovirus [AdCMVCATgD; $6 \times 10^6$, (n=4); $6 \times 10^7$, (n=4); $6 \times 10B$, (n=3); and $2 \times 10^9$, (n=2)].
Figure 21A:
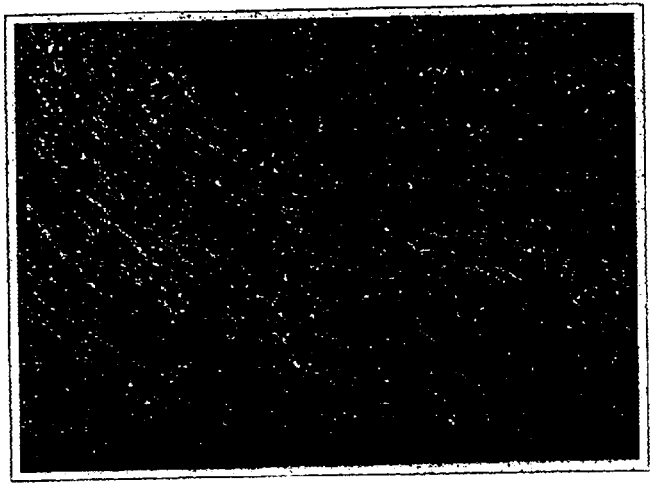
FIG. 21 (a–f) is an immunohistochemical staining for CAT protein in adenovirus infected hearts.
Figure 21B:
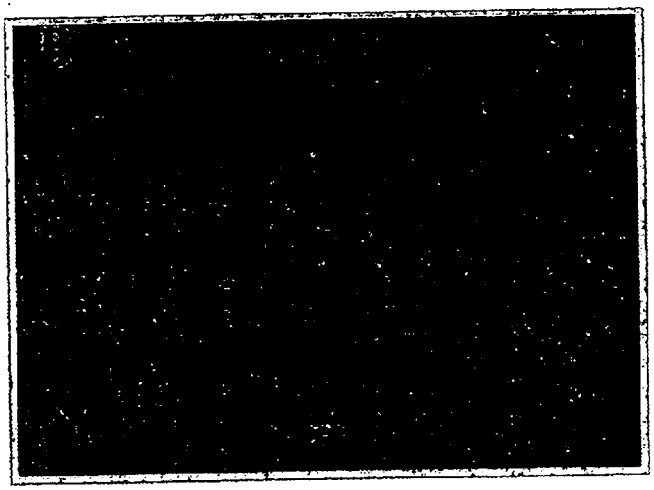
Figure 21C:
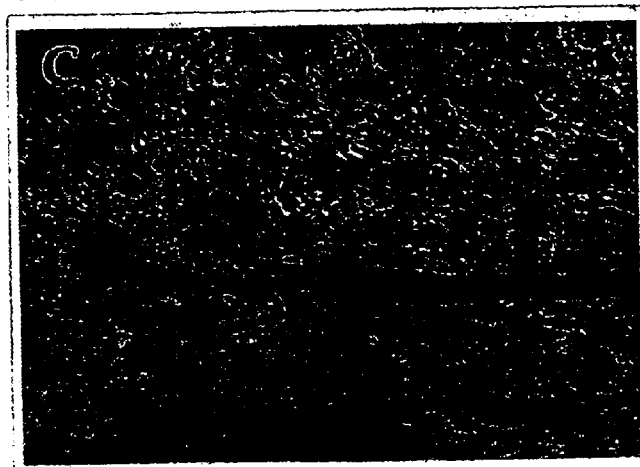
Figure 21D:
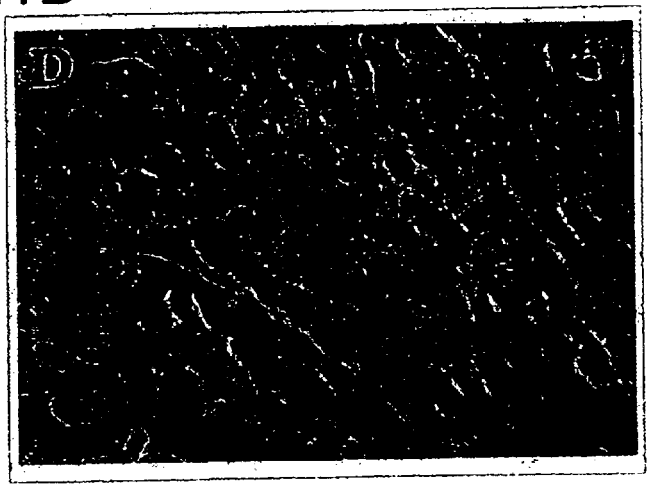
Figure 21E:
Figure 21F:
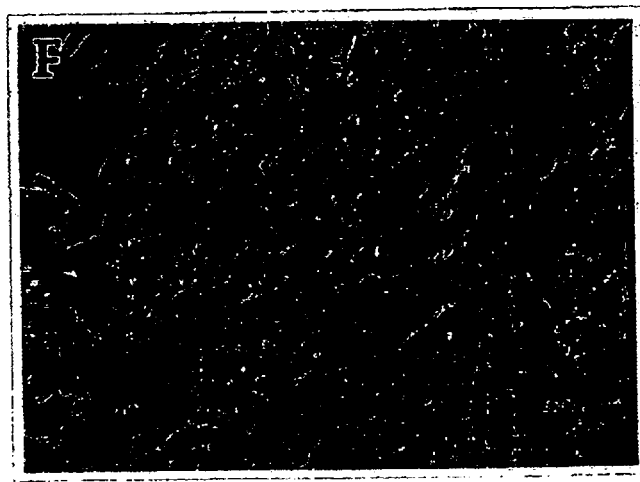

Given the high levels of CAT activity that were obtained from virus injection, the dose responsiveness of a range of virus from $6 \times 10^6$ pfu up to $2 \times 10^9$ pfu/injection was examined. Five days following injection, hearts were homogenized and assayed for CAT activity (FIG. 20($a$)). Increasing CAT activity correlated with increasing virus, although not in an entirely linear fashion. With reference to FIG. 20($b$), there is shown the duration of CAT activity following a single injection of $6 \times 10^7$ pfu of AdCMVCATgD. Animals were sacrificed and CAT activity in the left ventricle was measured 15 hours, 5 days, 12 days, 21 days, 43 days, and 55 days following injection. n=4, except for the 43 and 55 day time points, where n=2. CAT activity can be detected as early as 15 hours post infection, reaching maximal levels approximately 5 days post injection. Although CAT activity is still easily detectable 43 and 55 days following injection, expression levels are 5–6 logs lower relative to peak activity. To determine the number and type of cells in the heart which express CAT, tissue sections were stained with an anti-CAT antibody. As shown in FIG. 21, a very high proportion of cells in many regions of the myocardium are expressing CAT antigen at all doses of virus. Three doses of viral input are shown. A,B=$6 \times 10^6$; C,D=$6 \times 10^7$; E,F=$2 \times 10^9$. Photographs of tissue sections were taken under Differential Interference Contrast (DIC) microscopy). A,C,E; Bar=1 mm, B,D,F; Bar =0.05 mm. CAT positive cells are stained brown for peroxidase reaction. All sections are counterstained with hematoxylin. In many regions, virtually 100% of myocytes stain positive. Positive cells include both myocytes and nonmyocytes, although it appears that the proportion of myocytes infected exceeds that of non-myocytes. A substantial number of inflammatory cells were seen (See FIGS. 21($d$) & 21($e$)). The nature of this inflammatory response is currently under investigation but does not appear to correlate with the amount of introduced virus. The intensity of peroxidase staining appeared to increase with increasing viral dose. It appears that the lowest dose of virus ($6 \times 10^6$) resulted in a lower intensity of CAT antigen/cell as well as reduced number of infected cells. At higher doses of virus, both an increased number of cells and an increased amount of CAT/cell were obtained.

Cardiac myocytes appear to be ideally suited for the use of adenovirus mediated gene transfer. Transient transfection of fetal cardiocytes under optimized conditions traditionally results in 10–20% of the cells being transfected. Adenovirus can infect virtually 100% of cells and does not require the use of damaging treatments such as electroporation which generally kills a large number of the cells in the culture. Clearly, fetal cardiocytes possess viral receptors in numbers do not present a limitation to use of adenovirus vectors in rat cardiocytes. With adenovirus infection, there is no apparent effect on cell viability or morphology at the pfu ratios tested here. In addition, adenovirus infections also provide an efficient means of gene transfer into adult cells which has not been possible using conventional transfection strategies (Kirshenbaum et al., 1993, *J. Clin. Invest.*, vol., 92, pp. 381–387, which disclosure is hereby incorporated by reference). A recent report of adenovirus infection of adult rat cardiocytes (Kirshenbaum et al., 1993, *J. Clin. Invest.*, vol. 92, pp. 381–387, which disclosure is hereby incorporated by reference) reported 90% infection at a dose of $10^3$ pfu/cell. Based on the results of the present invention, it is not necessary to use such a high dose of virus. Because of the efficient CAT expression system, the viral dose required for infection of virtually all cells is in the vicinity of 1 pfu/cell (100 particles). In addition, due to the ability to accurately and reproducibly assay the reporter gene activity within the first 24 hours of infection, studies on primary cell cultures can be accomplished at times when host expression functions may not have been grossly altered, which may not be the case with more conventional transfection techniques.

As shown in FIG. 21, in many regions of the heart, virtually 100% of the myocytes were infected. One question that arises is whether genes introduced by adenovirus can produce enough protein to functionally modify the phenotype or physiology of a target organ or animal. We estimate that at least 150 $\mu$g of CAT protein can be expressed in a single rat heart following administration of $2 \times 10^9$ pfu of virus, suggesting that the quantity of a foreign gene product is not likely to be a limitation.

When tissue sections were stained with an anti-CAT antibody, both the number of positive cells as well as the amount of CAT protein per cell increased with increasing virus dose. This was most apparent at the two lowest doses of virus ($6 \times 10^6$ and $6 \times 10^7$ pfu). This difference was not as apparent among the three highest doses of virus, probably because of the non- quantitative nature of the peroxidase stain. The adult rat heart has been estimated to have $2 \times 10^7$ myocytes, which represent about 80% of the cells in the intact heart. If adenovirus infection in vivo is as efficient as it is in vitro, then the three highest doses of virus would theoretically result in infection of all myocytes in the heart. It is difficult to estimate the total number of positive cells because of the unknown sensitivity of the antibody in a paraffin and the variation in the staining intensity. However, we can demonstrate many regions in any one heart that appear to be 100% positive, and other regions with somewhat less CAT antigen, as well as some regions that do not show any apparent staining. Visual inspection suggests that a vastly greater number of cells is infected than when plasmid DNA is introduced by injection (Kitsis et al., 1991, *Proc. Natl. Acad. Sci. USA*, vol. 88, pp. 4138–4142, which disclosure is hereby incorporated by reference).

One of the issues currently under debate concerning the use of adenovirus as a gene transfer vector is duration of expression of introduced genes. The results obtained in accordance with the present invention and those of Lemarchand et. al., 1993, *Circ. Res.*, vol. 72, pp. 1132–1138, which disclosure is hereby incorporated by reference, demonstrate a rather transient pattern of expression. It may be that in order to generate long-term expression it will be necessary to introduce the virus into neonates, as has been suggested by Strattford-Perricaudet et al., 1992, *J. Clin. Invest.*, vol. 90, pp. 626–630, which disclosure is hereby incorporated by reference. Studies are currently underway to examine the effect of various routes of infection, tissue distribution and immune response to this virus in vivo. However, it is apparent that adenovirus mediated gene transfer in the heart is extremely efficient and should be a very useful tool for the introduction of genes into cardiac myocytes.

It should be understood, that the foregoing embodiments are provided for purpose of illustration only and, not limitation, and that all such modifications or changes which occur to persons skilled in the art are deemed to be within the spirit and scope of the present invention.

SEQUENCE LISTING (1) GENERAL INFORMATION:

(iii) NUMBER OF SEQUENCES: 1

(2) INFORMATION FOR SEQ ID NO:1:

(i) SEQUENCE CHARACTERISTICS:
        (A) LENGTH: 6783 base pairs
        (B) TYPE: cDNA
        (C) STRANDEDNESS: double
        (D) TOPOLOGY: linear (ii) MOLECULE TYPE: cDNA (genomic)

(xi) SEQUENCE DESCRIPTION: SEQ ID NO:1:

```
TTCCATCATC AATAATATAC CTTATTTTGG ATTGAAGCCA ATATGATAAT GAGGGGGTGG      60

AGTTTGTGAC GTGGCGCGGG GCGTGGGAAC GGGGCGGGTG ACGTAGTAGT GTGGCGGAAG     120

TGTGATGTTG CAAGTGTGGC GGAACACATG TAAGCGACGG ATGTGGCAAA AGTGACGTTT     180

TTGGTGTGCG CCGGTGTACA CAGGAAGTGA CAATTTTCGC GCGGTTTTAG GCGGATGTTG     240

TAGTAAATTT GGGCGTAACC GAGTAAGATT TGGCCATTTT CGCGGGAAAA CTGAATAAGA     300

GGAAGTGAAA TCTGAATAAT TTTGTGTTAC TCATAGCGCG TAATATTTGT CTAGGGCCTT     360

GCGGCCGCAA GTTGACATTG ATTATTGACT AGTTATTAAT AGTAATCAAT TACGGGGTCA     420

TTAGTTCATA GCCCATATAT GGAGTTCCGA GTTACATAAC TTACGGTAAA TGGCCCGCCT     480

GGCTGACCGC CCAACGACCC CCGCCCATTG ACGTCAATAA TGACGTATGT TCCCATAGTA     540

ACGCGAATAG GGACTTTCCA TTGACGTCAA TGGGTGGAGT ATTTACGGTA AACTGCCCAC     600

TTGGCAGTAC ATCAAGTGTA TCATATGCCA AGTACGCCCC CTATTGACGT CAATGACGGT     660

AAATGGCCCG CCTGGCATTA TGCCCAGTAC ATGACCTTAT GGGACTTTCC TACTTGGCAG     720

TACATCTACG TATTAGTCAT CGCTATTACC ATGGTGATGC GGTTTTGGCA GTACATCAAT     780

GGGCGTGGAT AGCGGTTTGA CTCACGGGGA TTTCCAAGTC TCCACCCCAT TGACGTCAAT     840

GGGAGTTTGT TTTGGCACCA AAATCAACGG GACTTTCCAA AATGTCGTAA CAACTCCGCC     900

CCATTGACGC AAAGGGTCGG TAGGCGTGTA CGGTGGGAGG TCTATATAAG CAGAGCTCGC     960

CCGGGGATCC TCTAGAATTC GCTGTCTGCG AGGGCCAGCT GTTGGGGTGA GTACTCCCTC    1020

TCAAAAGCGG GCATGACTTC TGCGCTAAGA TTGTCAGTTT CCAAAAACGA GGAGGATTTG    1080
```

-continued

```
ATATTCACCT GGCCCGCGGT GATGCCTTTG AGGGTGGCCG CGTCCATCTG GTCAGAAAAG    1140

ACAATCTTTT TGTTGTCAAA AGCGCTTGAG GTGTGGCAGG CTTGAGATCT GGCCATACAC    1200

TTGAGTGACA ATGACATCCA CTTTGCCTTT CTCTCCACAG GTGTCCACTC CCAGGTCCAA    1260

CTGCAGCCCC CAAGCTTGGT ACCGGTGATC AGATATCTCG AGGTACCGTC GACGGTATCG    1320

CCCGACATCA CCTGTGTCTA TGGCCACTGC CTTGGCTCAC AAGTACCACT AAACCCCCTT    1380

TCCTGCTCTT GCCTGTGAAC AATGGTTAAT TGTTCCCAAG AGAGCATCTG TCAGTTGTTG    1440

GCAAAATGAT AGACATTTGA AAATCTGTCT TCTGACAAAT AAAAAGCATT TATGTTCACT    1500

GCAATGATGT TTTAAATTAT TTGTCTGTGT CATAGAAGGG TTTATGCTAA GTTTTCAAGA    1560

TACAAAGAAG TGAGGCTTCA GGTCTGACCT TGGGGAAATA AATGAATTAC ACTTCAAATT    1620

GTGTTGTCAG CTAAGCAGCA GTAGCCACAG TCTAGCTGAG GGTAACTCCA GGGTGCGCCA    1680

CAATGTGGCC TCCGACTGTG GTTGCTTCAT GCTAGTGAAA AGCGTGGCTG TGATTAAGCA    1740

TAACATGGTA TGTGGCAACT GCGAGGACAG GGCCTCTCAG ATGCTGACCT GCTCGGACGG    1800

CAACTGTCAC CTGCTGAAGA CCATTCACGT AGCCAGCCAC TCTCGCAAGG CCTGGCCAGT    1860

GTTTGAGCAT AACATACTGA CCCGCTGTTC CTTGCATTTG GGTAACAGGA GGGGGGTGTT    1920

CCTACCTTAC CAATGCAATT TGAGTCACAC TAAGATATTG CTTGAGCCCG AGAGCATGTC    1980

CAAGGTGAAC CTGAACGGGG TGTTTGACAT GACCATGAAG ATCTGGAAGG TGCTGAGGTA    2040

CGATGAGACC CGCACCAGGT GCAGACCCTG CGAGTGTGGC GGTAAACATA TTAGGAACCA    2100

GCCTGTGATG CTGGATGTGA CCGAGGAGCT GAGGCCCGAT CACTTGGTGC TGGCCTGCAC    2160

CCGCGCTGAG TTTGGCTCTA GCTATGAAGA TACAGATTGA GGTACTGAAA TGTGTGGGCG    2220

TGGCTTAAGG GTGGGAAAGA ATATATAAGG TGGGGGTCTT ATGTAGTTTT GTATCTGTTT    2280

TGCAGCAGCC GCCGCCGCCA TGAGCACCAA CTCGTTTGAT GGAAGCATTG TGAGCTCATA    2340

TTTGACAACG CGCATGCCCC CATGGGCCGG GGTGCGTCAG AATGTGATGG GCTCCAGCAT    2400

TGATGGTCGC CCCGTCCTGC CCGCAAACTC TACTACCTTG ACCTACGAGA CCGTGTCTGG    2460

AACGCCGTTG GAGACTGCAG CCTCCGCCGC CGCTTCAGCC GCTGCAGCCA CCGCCCGCGG    2520

GATTGTGACT GACTTTGCTT TCCTGAGCCC GCTTGCAAGC AGTGCAGCTT CCCGTTCATC    2580

CGCCCGCGAT GACAAGTTGA CGGCTCTTTT GGCACAATTG GATTCTTTGA CCCGGGAACT    2640

TAATGTCGTT TCTCAGCAGC TGTTGGATCT GCGCCAGCAG GTTTCTGCCC TGAAGGCTTC    2700

CTCCCCTCCC AATGCGGTTT AAAACATAAA TAAAAAACCA GACTCTGTTT GGATTTGGAT    2760

CAAGCAAGTG TCTTGCTGTC TTTATTTAGG GGTTTTGCGC GCGCGGTAGG CCCGGGACCA    2820

GCGGTCTCGG TCGTTGAGGG TCCTGTGTAT TTTTTCCAGG ACGTGGTAAA GGTGACTCTG    2880

GATGTTCAGA TACATGGGCA TAAGCCCGTC TCTGGGGTGG AGGTAGCACC ACTGCAGAGC    2940

TTCATGCTGC GGGGTGGTGT TGTAGATGAT CCAGTCGTAG CAGGAGCGCT GGGCGTGGTG    3000

CCTAAAAATG TCTTTCAGTA GCAAGCTGAT TGCCAGGGGC AGGCCCTTGG TGTAAGTGTT    3060

TACAAAGCGG TTAAGCTGGG ATGGGTGCAT ACGTGGGGAT ATGAGATGCA TCTTGGACTG    3120

TATTTTTAGG TTGGCTATGT TCCCAGCCAT ATCCCTCCGG GGATTCATGT TGTGCAGAAC    3180

CACCAGCACA GTGTATCCGG TGCACTTGGG AAATTTGTCA TGTAGCTTAG AAGGAAATGC    3240

GTGGAAGAAC TTGGAGACGC CCTTGTGACC TCCAAGATTT TCCATGCATT CGTCCATAAT    3300

GATGGCAATG GGCCCACGGG CGGCGGCCTG GGCGAAGATA TTTCTGGGAT CACTAACGTC    3360

ATAGTTGTGT TCCAGGATGA GATCGTCATA GGCCATTTTT ACAAAGCGCG GCGGAGGGT    3420

GCCAGACTGC GGTATAATGG TTCCATCCGG CCCAGGGGCG TAGTTACCCT CACAGATTTG    3480
```

```
CATTTCCCAC GCTTTGAGTT CAGATGGGGG GATCATGTCT ACCTGCGGGG CGATGAAGAA    3540

AACGGTTTCC GGGGTAGGGG AGATCAGCTG GGAAGAAAGC AGGTTCCTGA GCAGCTGCGA    3600

CTTACCGCAG CCGGTGGGCC CGTAAATCAC ACCTATTACC GGGTGCAACT GGTAGTTAAG    3660

AGAGCTGCAG CTGCCGTCAT CCCTGAGCAG GGGGGCCACT TCGTTAAGCA TGTCCCTGAC    3720

TCGCATGTTT TCCCTGACCA AATCCGCCAG AAGGCGCTCG CCGCCCAGCG ATAGCAGTTC    3780

TTGCAAGGAA GCAAAGTTTT TCAACGGTTT GAGACCGTCC GCCGTAGGCA TGCTTTTGAG    3840

CGTTTGACCA AGCAGTTCCA GGCGGTCCCA CAGCTCGGTC ACCTGCTCTA CGGCATCTCG    3900

ATCCAGCATA TCTCCTCGTT TCGCGGGTTG GGGCGGCTTT CGCTGTACGG CAGTAGTCGG    3960

TGCTCGTCCA GACGGGCCAG GGTCATGTCT TTCCACGGGC GCAGGGTCCT CGTCAGCGTA    4020

GTCTGGGTCA CGGTGAAGGG GTGCGCTCCG GGCTGCGCGC TGGCCAGGGT GCGCTTGAGG    4080

CTGGTCCTGC TGGTGCTGAA GCGCTGCCGG TCTTCGCCCT GCGCGTCGGC CAGGTAGCAT    4140

TTGACCATGG TGTCATAGTC CAGCCCCTCC GCGGCGTGGC CCTTGGCGCG CAGCTTGCCC    4200

TTGGAGGAGG CGCCGCACGA GGGGCAGTGC AGACTTTTGA GGGCGTAGAG CTTGGGCGCG    4260

AGAAATACCG ATTCCGGGGA GTAGGCATCC GCGCCGCAGG CCCCGCAGAC GGTCTCGCAT    4320

TCCACGAGCC AGGTGAGCTC TGGCCGTTCG GGGTCAAAAA CCAGGTTTCC CCCATGCTTT    4380

TTGATGCGTT TCTTACCTCT GGTTTCCATG AGCCGGTGTC CACGCTCGGT GACGAAAAGG    4440

CTGTCCGTGT CCCCGTATAC AGACTTGAGA GGTCGAGCGA TGCCCTTGAG AGCCTTCAAC    4500

CCAGTCAGCT CCTTCCGGTG GGCGCGGGGC ATGACTATCG TCGCCGCACT TATGACTGTC    4560

TTCTTTATCA TGCAACTCGT AGGACAGGTG CCGGCAGCGC TCTGGGTCAT TTTCGGCGAG    4620

GACCGCTTTC GCTGGAGCGC GACGATGATC GGCCTGTCGC TTGCGGTATT CGGAATCTTG    4680

CACGCCCTCG CTCAAGCCTT CGTCACTGGT CCCGCCACCA AACGTTTCGG CGAGAAGCAG    4740

GCCATTATCG CCGGCATGGC GGCCGACGCG CTGGGCTACG TCTTGCTGGC GTTCGCGACG    4800

CGAGGCTGGA TGGCCTTCCC CATTATGATT CTTCTCGCTT CCGGCGGCAT CGGGATGCCC    4860

GCGTTGCAGG CCATGCTGTC CAGGCAGGTA GATGACGACC ATCAGGGACA GCTTCAAGGA    4920

TCGCTCGCGG GTAAAAAGGC CGCGTTGCTG GCGTTTTTCC ATAGGCTCCG CCCCCCTGAC    4980

GAGCATCACA AAAATCGACG CTCAAGTCAG AGGTGGCGAA ACCCGACAGG ACTATAAAGA    5040

TACCAGGCGT TTCCCCCTGG AAGCTCCCTC GTGCGCTCTC CTGTTCCGAG CCTGCCGCTT    5100

ACCGGATACC TGTCCGCCTT TCTCCCTTCG GGAAGCGTGG CGCTTTCTCA ATGCTCACGC    5160

TGTAGGTATC TCAGTTCGGT GTAGGTCGTT CGCTCCAAGC TGGGCTGTGT GCACGAACCC    5220

CCCGTTCAGC CCGACCGCTG CGCCTTATCC GGTAACTATC GTCTTGAGTC CAACCCGGTA    5280

AGACACGACT TATCGCCACT GGCAGCAGCC ACTGGTAACA GGATTAGCAG AGCGAGGTAT    5340

GTAGGCGGTG CTACAGAGTT CTTGAAGTGG TGGCCTAACT ACGGCTACAC TAGAAGGACA    5400

GTATTTGGTA TCTGCGCTCT GCTGAAGCCA GTTACCTTCG GAAAAGAGT TGGTAGCTCT    5460

TGATCCGGCA ACAAACCAC CGCTGGTAGC GGTGGTTTTT TGTTTGCAA GCAGCAGATT    5520

ACGCGCAGAA AAAAGGATC TCAAGAAGAT CCTTTGATCT TTTCTACGGG GTCTGACGCT    5580

CAGTGGAACG AAAACTCACG TTAAGGGATT TTGGTCATGA GATTATCAAA AAGGATCTTC    5640

ACCTAGATCC TTTTAAATTA AAAATGAAGT TTTAAATCAA TCTAAAGTAT ATATGAGTAA    5700

ACTTGGTCTG ACAGTTACCA ATGCTTAATC AGTGAGGCAC CTATCTCAGC GATCTGTCTA    5760

TTTCGTTCAT CCATAGTTGC CTGACTCCCC GTCGTGTAGA TAACTACGAT ACGGGAGGGC    5820
```

-continued

| | | | | | |
|---|---|---|---|---|---|
| TTACCATCTG | GCCCCAGTGC | TGCAATGATA | CCGCGAGACC | CACGCTCACC | GGCTCCAGAT | 5880 |
| TTATCAGCAA | TAAACCAGCC | AGCCGGAAGG | GCCGAGCGCA | GAAGTGGTCC | TGCAACTTTA | 5940 |
| TCCGCCTCCA | TCCAGTCTAT | TAATTGTTGC | CGGGAAGCTA | GAGTAAGTAG | TTCGCCAGTT | 6000 |
| AATAGTTTGC | GCAACGTTGT | TGCCATTGCT | GCAGGCATCG | TGGTGTCACG | CTCGTCGTTT | 6060 |
| GGTATGGCTT | CATTCAGCTC | CGGTTCCCAA | CGATCAAGGC | GAGTTACATG | ATCCCCCATG | 6120 |
| TTGTGCAAAA | AAGCGGTTAG | CTCCTTCGGT | CCTCCGATCG | TTGTCAGAAG | TAAGTTGGCC | 6180 |
| GCAGTGTTAT | CACTCATGGT | TATGGCAGCA | CTGCATAATT | CTCTTACTGT | CATGCCATCC | 6240 |
| GTAAGATGCT | TTTCTGTGAC | TGGTGAGTAC | TCAACCAAGT | CATTCTGAGA | ATAGTGTATG | 6300 |
| CGGCGACCGA | GTTGCTCTTG | CCCGGCGTCA | ACACGGGATA | ATACCGCGCC | ACATAGCAGA | 6360 |
| ACTTTAAAAG | TGCTCATCAT | TGGAAAACGT | TCTTCGGGGC | GAAAACTCTC | AAGGATCTTA | 6420 |
| CCGCTGTTGA | GATCCAGTTC | GATGTAACCC | ACTCGTGCAC | CCAACTGATC | TTCAGCATCT | 6480 |
| TTTACTTTCA | CCAGCGTTTC | TGGGTGAGCA | AAAACAGGAA | GGCAAAATGC | CGCAAAAAAG | 6540 |
| GGAATAAGGG | CGACACGGAA | ATGTTGAATA | CTCATACTCT | TCCTTTTTCA | ATATTATTGA | 6600 |
| AGCATTTATC | AGGGTTATTG | TCTCATGAGC | GGATACATAT | TTGAATGTAT | TTAGAAAAAT | 6660 |
| AAACAAATAG | GGGTTCCGCG | CACATTTCCC | CGAAAAGTGC | CACCTGACGT | CTAAGAAACC | 6720 |
| ATTATTATCA | TGACATTAAC | CTATTAAAAT | AGGCGTATCA | CGAGGCCCTT | TCGTCTTCAA | 6780 |
| GAA | | | | | | 6783 |

What is claimed:

1. An adenoviral vector for expressing a heterologous gene(s) in a host cell, the adenoviral vector comprising an adenoviral E1 region, wherein said adenoviral E1 region comprises the following in 5' to 3' order: a heterologous promoter; a eukaryotic splice acceptor site; a eukaryotic splice donor site; at least one insertion site for cloning a selected heterologous gene; and a polyadenylation sequence, wherein the heterologous promoter is oriented to drive transcription of the heterologous gene in a direction opposite to the direction of transcription of the adenoviral E1 region.

2. The adenoviral vector according to claim 1, wherein said heterologous promoter is a mouse cytomegalovirus early promoter, or an effective expression promoting fragment thereof.

3. The adenoviral vector according to claim 1, wherein said polyadenylation sequence is the mouse β-globin polyadenylation sequence.

4. The adenoviral vector according to claim 1, wherein said at least one insertion site further comprises a second insertion site for insertion of a second heterologous gene.

5. The adenoviral vector according to claim 1, wherein said adenoviral vector further comprises heterologous DNA inserted in said at least one insertion site.

6. A host cell infected with adenoviral vector of claim 5.

7. A method for producing a selected protein, which method comprises culturing a host cell which has been infected with the adenoviral vector of claim 5, wherein said heterologous DNA encodes a selected protein, whereupon said selected protein is produced.

8. A method of delivering a heterologous gene to an animal in vivo, wherein the method comprises administering to the animal an adenoviral vector comprising an adenoviral E1 region, wherein said adenoviral E1 region comprises the following elements in 5' to 3' order: a heterologous promoter; a eukaryotic splice acceptor site; a eukaryotic splice donor site; heterologous gene; and a polyadenylation sequence, wherein the heterologous promoter is oriented to drive transcription of the heterologous gene in a direction opposite to the direction of transcription of the adenoviral E1 region.

9. A method of delivering a heterologous gene to an animal heart in vivo, wherein the method comprises administering to the animal heart an adenoviral vector comprising an adenoviral E1 region, wherein said adenoviral E1 region comprises the following elements in 5' to 3' order: a heterologous promoter; a eukaryotic splice acceptor site; a eukaryotic splice donor site; heterologous gene, and a polyadenylation sequence, wherein the heterologous promoter is oriented to drive transcription of the heterologous gene in a direction opposite to the direction of transcription of the adenoviral E1 region.

* * * * *